United States Patent
Sazani et al.

(10) Patent No.: US 7,785,834 B2
(45) Date of Patent: Aug. 31, 2010

(54) SOLUBLE TNF RECEPTORS AND THEIR USE IN TREATMENT OF DISEASE

(75) Inventors: Peter L. Sazani, Chapel Hill, NC (US); Maria Graziewicz, Chapel Hill, NC (US); Ryszard Kole, Chapel Hill, NC (US); Henrik Ørum, Vaerlose (DK)

(73) Assignees: Ercole Biotech, Inc., Research Triangle Park, NC (US); University of North Carolina at Chapel Hill, Chapel Hill, NC (US); Santaris Pharma A/S, Horsholm (DK)

( * ) Notice: Subject to any disclaimer, the term of this patent is extended or adjusted under 35 U.S.C. 154(b) by 0 days.

(21) Appl. No.: 11/799,117

(22) Filed: May 1, 2007

(65) Prior Publication Data

US 2007/0249538 A1    Oct. 25, 2007

Related U.S. Application Data

(63) Continuation-in-part of application No. 11/595,485, filed on Nov. 10, 2006.

(60) Provisional application No. 60/862,350, filed on Oct. 20, 2006, provisional application No. 60/735,429, filed on Nov. 10, 2005.

(51) Int. Cl.
    C07H 21/04    (2006.01)
    A61K 38/17    (2006.01)
    C12N 15/12    (2006.01)
    C12N 15/63    (2006.01)
    C12N 15/28    (2006.01)

(52) U.S. Cl. .............. 435/69.1; 536/23.5; 530/350; 435/320.1; 435/361; 435/252.3

(58) Field of Classification Search .............. None
See application file for complete search history.

(56) References Cited

U.S. PATENT DOCUMENTS

| | | |
|---|---|---|
| 5,605,690 A | 2/1997 | Jacobs et al. |
| 5,665,859 A | 9/1997 | Wallach et al. |
| 5,672,347 A | 9/1997 | Aggarwal et al. |
| 5,808,029 A | 9/1998 | Brockhaus et al. |
| 5,863,786 A | 1/1999 | Feldmann et al. |
| 5,945,397 A | 8/1999 | Smith et al. |
| 5,976,879 A | 11/1999 | Kole et al. |
| 6,007,995 A | 12/1999 | Baker et al. |
| RE36,755 E | 6/2000 | Smith et al. |
| 6,201,105 B1 | 3/2001 | Smith et al. |
| 6,210,892 B1 | 4/2001 | Bennett et al. |
| 6,410,324 B1 | 6/2002 | Bennett et al. |
| 6,417,158 B1 | 7/2002 | Hauptmann et al. |
| 6,441,136 B1 | 8/2002 | Pettit |
| 6,537,540 B1 | 3/2003 | Burstein et al. |
| 6,541,620 B1 | 4/2003 | Brewer et al. |
| 6,572,852 B2 | 6/2003 | Smith et al. |
| 7,186,682 B2 | 3/2007 | Wallach et al. |
| 7,282,483 B2 | 10/2007 | Hauptmann et al. |
| 2002/0155112 A1 | 10/2002 | Hauptmann et al. |
| 2002/0169118 A1 | 11/2002 | Hauptmann et al. |
| 2002/0183485 A1 | 12/2002 | Hauptmann et al. |
| 2003/0082736 A1 | 5/2003 | Smith |
| 2003/0220283 A1 | 11/2003 | Glorioso et al. |
| 2003/0235845 A1 | 12/2003 | van Ommen et al. |
| 2004/0013646 A1 | 1/2004 | Wallach et al. |
| 2004/0147471 A1 | 7/2004 | Zhang |
| 2004/0186069 A1 | 9/2004 | Bennett et al. |
| 2005/0202531 A1 | 9/2005 | Toporik |
| 2005/0245731 A1 | 11/2005 | Wallach et al. |
| 2006/0099616 A1 | 5/2006 | van Ommen et al. |
| 2006/0147952 A1 | 7/2006 | van Ommen et al. |
| 2007/0105807 A1 | 5/2007 | Sazani et al. |
| 2007/0249538 A1 | 10/2007 | Sazani et al. |
| 2009/0264353 A1 | 10/2009 | Orum et al. |

FOREIGN PATENT DOCUMENTS

| | | |
|---|---|---|
| WO | WO94/06476 | 3/1994 |
| WO | WO00/53624 | 9/2000 |
| WO | WO00/58512 | 10/2000 |
| WO | WO02/088393 | 11/2002 |
| WO | WO03/070897 | 8/2003 |
| WO | WO2007/058894 | 5/2007 |
| WO | WO2007/028065 | 8/2007 |
| WO | WO2008/051306 | 5/2008 |
| WO | WO2008/131807 | 11/2008 |

OTHER PUBLICATIONS

Genbank Accession No. P20333, printed Dec. 2008, 12 pages.*
Genbank Accession No. NM_001066, printed Dec. 2008, 9 pages.*
Moosmayer et al., Characterization of Different Soluble TNF Receptor (TNFR80) Derivatives: Positive Influence of . . . , J. Interferon and Cytokine Res., 1996, 16:471-477.
Shen et al., Inhibition of p75 Tumor Necrosis Factor Receptor by Antisense Oligonucleotides Increases . . . , The Journal of Biological Chemistry, 1997, 272(6):3550-3553.
Aartsma-Rus et al., Targeted Exon Skipping as a Potential Gene Correction Therapy for Duchenne Muscular Dystrophy, Neuromuscular Disorders, 2002, 12:S71-S77.
Lainez et al., Identification and Characterization of a Novel Spliced Variant that Encodes Human Soluble Tumor Necrosis Factor Receptor 2, International Immunology, 2004, 16:1.
Siwkowski et al., Identification and Functional Validation of PNAs that Inhibit Murine CD40 Expression by Redirection of Splicing, Nucleic Acids Research, 2004, 32:2695-2706.
Sandalon et al., Secretion of a TNFR:Fc Fusion Protein following Pulmonary Administration of Pesudotyped Adeno-Associated Virus Vectors, Journal of Virology, 2004, 78:12355-12365.

\* cited by examiner

*Primary Examiner*—Lorraine Spector
(74) *Attorney, Agent, or Firm*—Fish & Richardson P.C.

(57) ABSTRACT

The present invention relates to tumor necrosis factor (TNF) antagonists and corresponding nucleic acids derived from tumor necrosis factor receptors (TNFRs) and their use in the treatment of inflammatory diseases. These proteins are soluble secreted decoy receptors that bind to TNF and prevent TNF from signaling to cells. In particular, the proteins are mammalian TNFRs that lack exon 7 and which can bind TNF and can act as a TNF antagonist.

6 Claims, 22 Drawing Sheets

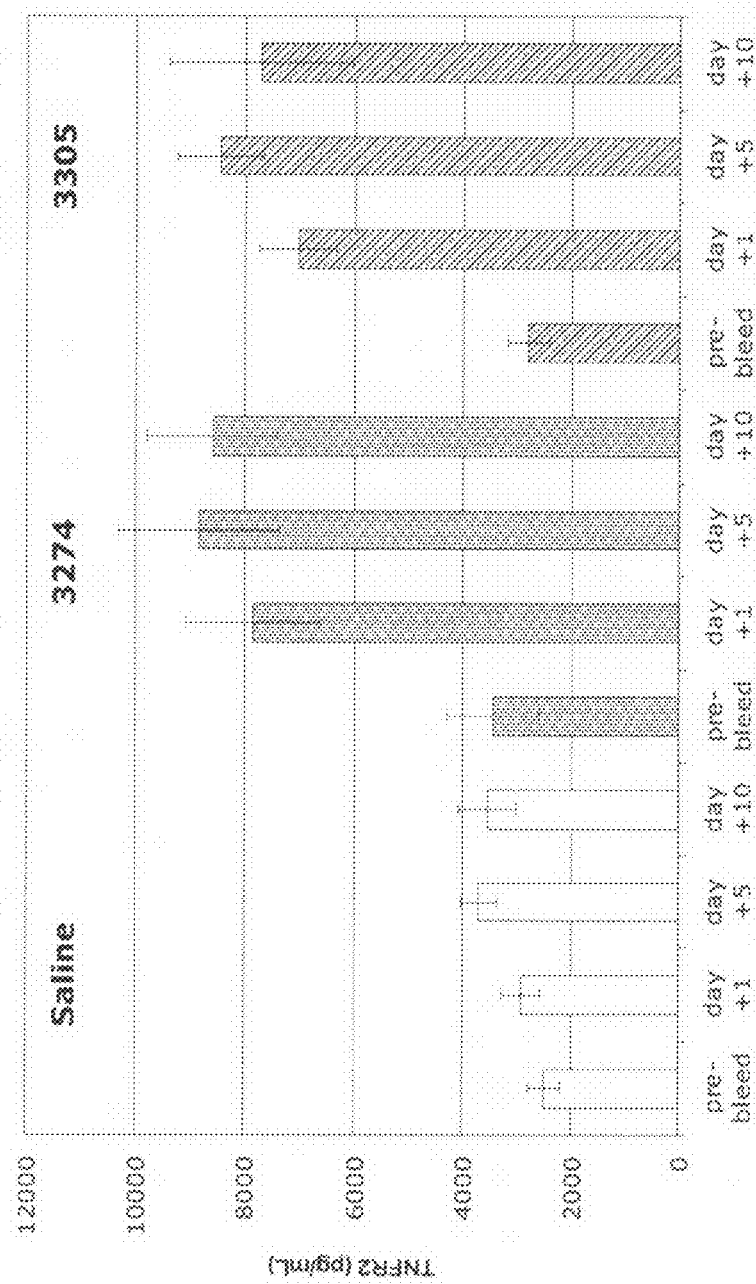
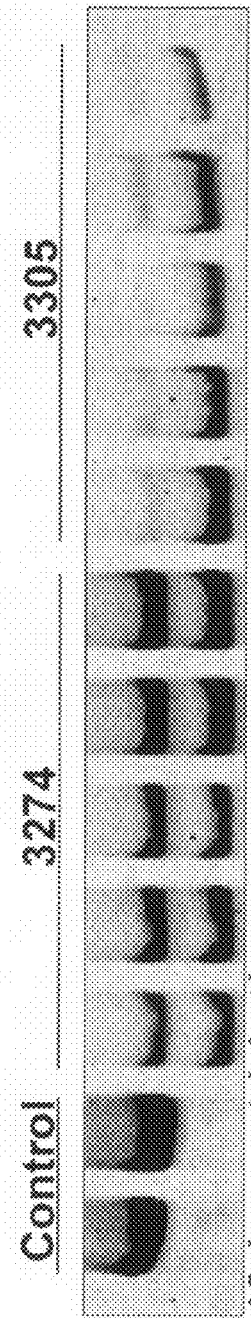
Figure 11A
Figure 11B

SOLUBLE TNF RECEPTORS AND THEIR USE IN TREATMENT OF DISEASE

This application is a continuation-in-part of U.S. application Ser. No. 11/595,485, filed Nov. 10, 2006 which claims priority to U.S. Provisional application Ser. No. 60/862,350, filed Oct. 20, 2006, and U.S. Provisional application Ser. No. 60/735,429, filed Nov. 10, 2005, all of which are incorporated by reference herein in their entirety.

FIELD OF THE INVENTION

The present invention relates to tumor necrosis factor (TNF) antagonists and corresponding nucleic acids derived from TNF receptors and their use in the treatment of inflammatory diseases. These proteins are soluble secreted decoy receptors that bind to TNF-α and prevent TNF-α from signaling to cells.

BACKGROUND OF THE INVENTION

TNF-α is a pro-inflammatory cytokine that exists as a membrane-bound homotrimer and is released as a homotrimer into the circulation by the protease TNF-α converting enzyme (TACE). TNF-α is introduced into the circulation as a mediator of the inflammatory response to injury and infection. TNF-α activity is implicated in the progression of inflammatory diseases such as rheumatoid arthritis, Crohn's disease, ulcerative colitis, psoriasis and psoriatic arthritis (Palladino, M. A., et al., 2003, Nat. Rev. Drug Discov. 2:736-46). Acute exposure to high TNF-α levels, as experienced during a massive infection, results in sepsis. Its symptoms include shock, hypoxia, multiple organ failure, and death. Chronic low-level release of TNF-α is associated with malignancies and leads to cachexia, a disease characterized by weight loss, dehydration and fat loss.

TNF-α activity is mediated primarily through two receptors coded by two different genes, TNF-α receptor type I (hereafter "TNFR1", exemplified by GenBank accession number X55313 for human TNFR1) and TNF-α receptor type II (hereafter "TNFR2", exemplified by GenBank accession number NM_001066 for human TNFR2). TNFR1 is a membrane-bound protein with a molecular weight of approximately 55 kilodaltons (kDal), while TNFR2 is a membrane-bound protein with a molecular weight of approximately 75 kDal. TNFR1 and TNFR2 belong to a family of receptors known as the TNF receptor (TNFR) superfamily. The TNFR superfamily is a group of type I transmembrane proteins, with a carboxy-terminal intracellular domain and an amino-terminal extracellular domain characterized by a common cysteine rich domain (CRD). TNFR1 and TNFR2 have a unique domain in common, called the pre-ligand-binding assembly domain (PLAD) that is required for assembly of multiple receptor subunits and subsequent binding to TNF-α.

TNFR1 and TNFR2 also share a common gene structure, in which the coding sequence of each extends over 10 exons separated by 9 introns (Fuchs, et al., 1992, Genomics 13:219; Santee, et al., 1996, J. Biol. Chem. 35:21151). Most of the transmembrane domain sequence is encoded by the seventh exon ("exon 7") (See FIG. 1).

Experiments in knockout mice lacking both TNFR1 and TNFR2 demonstrated that the injury-induced immune response to brain injury was suppressed, suggesting that drugs that target the TNF signaling pathways may be beneficial in treating stroke or traumatic brain injury (Bruce, et al., 1996, Nat. Med. 2:788). TNFR2 knockout mice, but not TNFR1 knockout mice, were resistant to experimentally-induced cerebral malaria (Lucas, R., et al., 1997, Eur. J. Immunol. 27:1719); whereas TNFR1 knockout mice were resistant to autoimmune encephalomyelitis (Suvannavejh, G. C., et al., 2000, Cell. Immunol., 205:24). These knockout mice are models for human cerebral malaria and multiple sclerosis, respectively.

TNFR2 is present at high density on T cells of patients with interstitial lung disease, suggesting a role for TNFR2 in the immune responses that lead to alveolitis (Agostini, C., et al., 1996, Am. J. Respir. Crit. Care Med., 153:1359). TNFR2 is also implicated in human disorders of lipid metabolism. TNFR2 polymorphism is associated with obesity and insulin resistance (Fernandez-Real, et al., 2000, Diabetes Care, 23:831), familial combined hyperlipidemia (Geurts, et al., 2000, Hum. Mol. Genet 9:2067), hypertension and hypercholesterolemia (Glenn, et al., 2000, Hum. Mol. Genet., 9:1943). In addition, TNFR2 polymorphism is associated with susceptibility to human narcolepsy (Hohjoh, H., et al., 2000, Tissue Antigens, 56:446) and to systemic lupus erythematosus (Komata, T., et al., 1999, Tissue Antigens, 53:527).

To simplify further analysis and comparison, the human TNFR2 461 amino acid sequence provided in SEQ ID No: 4, GenBank accession number NP_001057, is used as a reference unless stated otherwise (FIG. 1). Amino acid 1 is the first amino acid of the full length protein human TNFR2, which includes the signal sequence. Amino acid 23 located in exon 1 is the first amino acid of the mature protein, which is the protein after cleavage of the signal sequence. The transmembrane region spans amino acids 258-287. The exon 6/7 junction is located within the codon that encodes residue 263, while the exon 7/8 junction is located within the codon that encodes residue 289.

Physiological, soluble fragments of both TNFR1 and TNFR2 have been identified. For example, soluble extracellular domains of these receptors are shed to some extent from the cell membrane by the action of metalloproteases (Palladino, M. A., et al., 2003, Nat. Rev. Drug Discov. 2:736-46). Additionally, the pre-mRNA of TNFR2 undergoes alternative splicing, creating either a full length, active membrane-bound receptor, or a secreted receptor that lacks exons 7 and 8 (Lainez et al., 2004, Int. Immunol., 16:169) ("Lainez"). The secreted protein binds TNF-α but does not elicit a physiological response, hence reducing overall TNF-α activity. Although an endogenous, secreted splice variant of TNFR1 has not yet been identified, the similar genomic structure of the two receptors suggests that a TNFR1 splice variant can be produced.

The cDNA for the splice variant identified by Lainez contains the 113 bp deletion of exons 7 and 8. This deletion gives rise to a stop codon 17 bp after the end of exon 6. Consequently, the protein has the sequence encoded by the first six exons of the TNFR2 gene (residues 1-262) followed by a 6 amino acid tail of Ala-Ser-Leu-Ala-Cys-Arg.

Additional soluble fragments of recombinantly-engineered TNF receptors are known. In particular, truncated forms of TNFR1 or TNFR2 have been produced which have (1) all or part of the extracellular domain or (2) a TNFR extracellular domain fused to another protein.

Smith discloses truncated human TNFR2s, including a protein with residues 23-257, which terminates immediately before the transmembrane region, and a protein with residues 23-185 (U.S. Pat. No. 5,945,397). Both TNFR2 fragments are soluble and capable of binding TNF-α.

Craig discloses that an extracellular domain of human TNFR2 with residues 23-257 fused to the Fc region of human IgG$_1$ (TNFR:Fc) is a TNF-α antagonist capable of reducing inflammation in rat and mice arthritis models (U.S. Pat. No.

5,605,690). TNFR:Fc is an FDA-approved treatment for certain forms of arthritis, ankylosing spondylitis, and psoriasis and is sold under the name etanercept (Enbrel®).

Moosmayer demonstrated that soluble human TNFR2 proteins containing the entire intracellular domain are more active TNF antagonists than the extracellular domain alone (Moosmayer et al., 1996, J. Interferon Cytokine Res., 16:471). In those experiments, Moosmayer compared the activities of solubilized full length TNFR2 (1-461), with TNFR2 lacking all but the three C-terminal amino acids of the transmembrane region (ΔTM) (1-258 joined to 283-461), TNFR extracellular domain (1-258), and TNFR:Fc. The inhibition of TNF-mediated cytotoxicity by the ΔTM protein and solubilized full length TNFR2 are comparable. However, their activities are approximately 60-fold higher than the TNFR2 extracellular domain alone, but approximately sevenfold less than TNFR:Fc.

Since excess TNF-α activity is associated with disease pathogenesis, particularly for inflammatory conditions, there is a need for TNF-α antagonists and methods for their use in the treatment of inflammatory diseases. Concerns have been raised regarding the side effects of currently approved protein-based TNF-α antagonists, including TNFR:Fc; these concerns include exacerbation of latent tuberculosis, worsening of congestive heart failure, and increased risk of lymphoma (Palladino, M. A., et al., 2003, Nat. Rev. Drug Discov. 2:736-46). Furthermore, there are patients who do not respond to currently approved TNF-α antagonists. Therefore, there is a continuing need to identify new TNF-α antagonists.

To that end, Sazani et al. have shown, inter alia, that by using splice switching oligonucleotides (SSOs) it is possible to generate alternatively spliced mRNA coding for variant TNFR1 or TNFR2 proteins using the naturally-occurring exon and intron structure (U.S. application Ser. No. 11/595, 485). In particular, the SSOs lead the cell to produce mRNAs that encode novel TNFR proteins that lack only exon 7, which encodes most of the transmembrane region of these proteins. Further characterization of the TNFR2 protein lacking only exon 7 surprisingly showed that it is a particularly stable, soluble decoy receptor that binds to and inactivates extracellular TNF-α. This protein unexpectedly has anti-TNF-α activity that is at least equivalent to TNFR:Fc.

SUMMARY OF THE INVENTION

One embodiment of the invention is a protein, either full length or mature, which can bind TNF, is encoded by a cDNA derived from a mammalian TNFR gene, and in the cDNA exon 6 is followed directly by exon 8 and as a result lacks exon 7 ("TNFR Δ7"). In another embodiment, the invention is a pharmaceutical composition comprising a TNFR Δ7. In a further embodiment, the invention is a method of treating an inflammatory disease or condition by administering a pharmaceutical composition comprising a TNFR Δ7.

In yet another embodiment, the invention is a nucleic acid that encodes a TNFR Δ7. In a further embodiment, the invention is a pharmaceutical composition comprising a nucleic acid that encodes a TNFR Δ7.

In another embodiment, the invention is an expression vector comprising a nucleic acid that encodes a TNFR Δ7. In a further embodiment, the invention is a method of increasing the level of a soluble TNFR in the serum of a mammal by transforming cells of the mammal with an expression vector comprising a nucleic acid that encodes a TNFR Δ7.

In another embodiment, the invention is a cell transformed with an expression vector comprising a nucleic acid that encodes a TNFR Δ7. In a further embodiment, the invention is a method of producing a TNFR Δ7 by culturing, under conditions suitable to express the TNFR Δ7, a cell transformed with an expression vector comprising a nucleic acid that encodes a TNFR Δ7. In yet another embodiment, the invention is a method of treating an inflammatory disease or condition by administering an expression vector comprising a nucleic acid that encodes a TNFR Δ7.

In yet another embodiment, splice-switching oligomers (SSOs) are disclosed that alter the splicing of a mammalian TNFR2 pre-mRNA to produce a mammalian TNFR2 protein, which can bind TNF and where exon 6 is followed directly by exon 8 and as a result lacks exon 7 ("TNFR2 Δ7"). One embodiment of the invention is a method of treating an inflammatory disease or condition by administering SSOs to a patient or a live subject. The SSOs that are administered alter the splicing of a mammalian TNFR2 pre-mRNA to produce a TNFR2 Δ7. In another embodiment, the invention is a method of producing a TNFR2 Δ7 in a cell by administering SSOs to the cell.

The foregoing and other objects and aspects of the present invention are discussed in detail in the drawings herein and the specification set forth below.

Figure 4A:
FIGS. 4A and 4B show the splicing products of mice treated with SSO 10-mers targeted to mouse TNFR2 exon 7. The indicated SSOs were resuspended in saline, and injected i.p. into mice at 25 mg/kg/day for 5 days. Mice were prebled before SSO injection, and 10 days after the final SSO injection and sacrificed. At the time of sacrifice, total RNA from livers was analyzed for TNFR2 splice switching by RT-PCR. FL—full length TNFR2; Δ7—TNFR2 Δ7 (FIG. 4A). The concentration of TNFR2 Δ7 in the serum taken before (Pre)
Figure 4B:
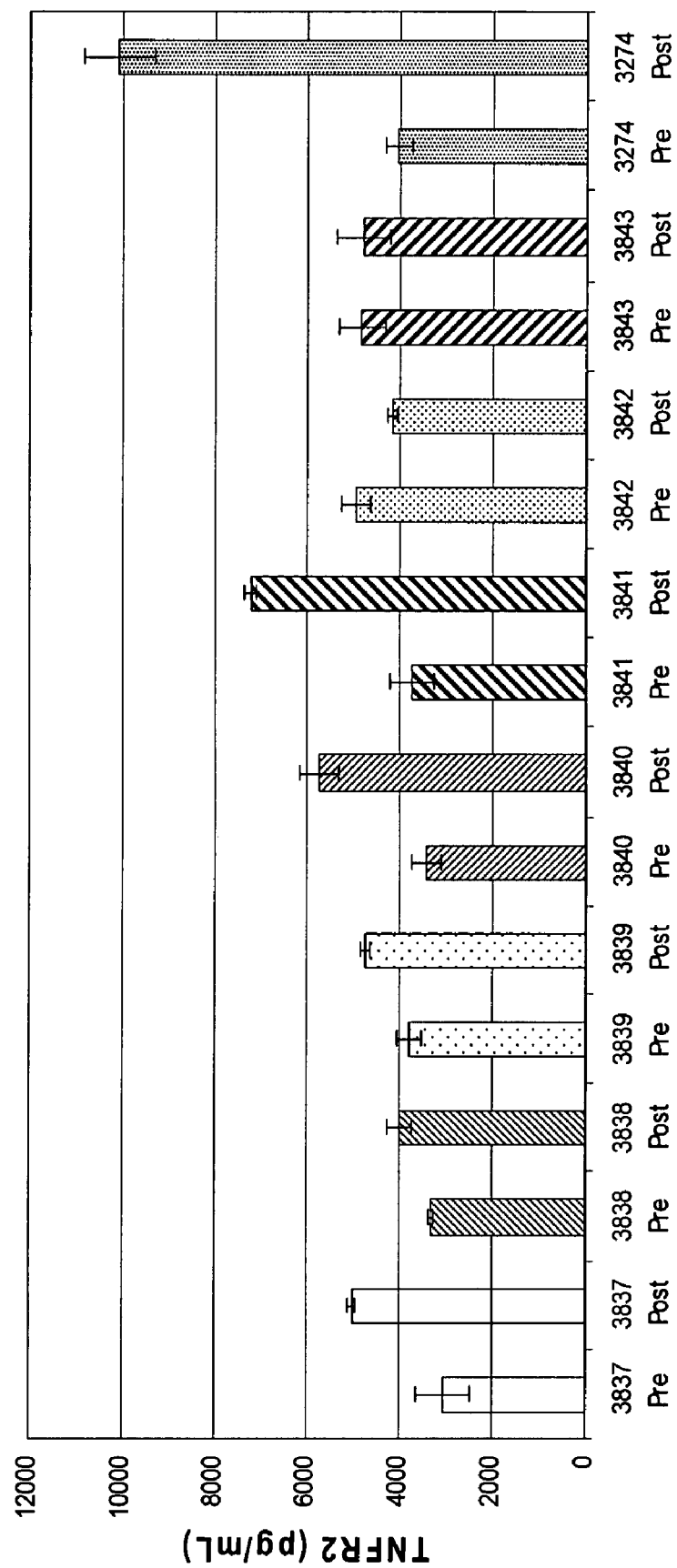

and after (Post) SSO injection was determined by ELISA using the Quantikine® Mouse sTNF RII ELISA kit from R&D Systems (Minneapolis, Minn.) (FIG. 4B). Error bars represent the standard error from 3 independent readings of the same sample.

Figure 5:
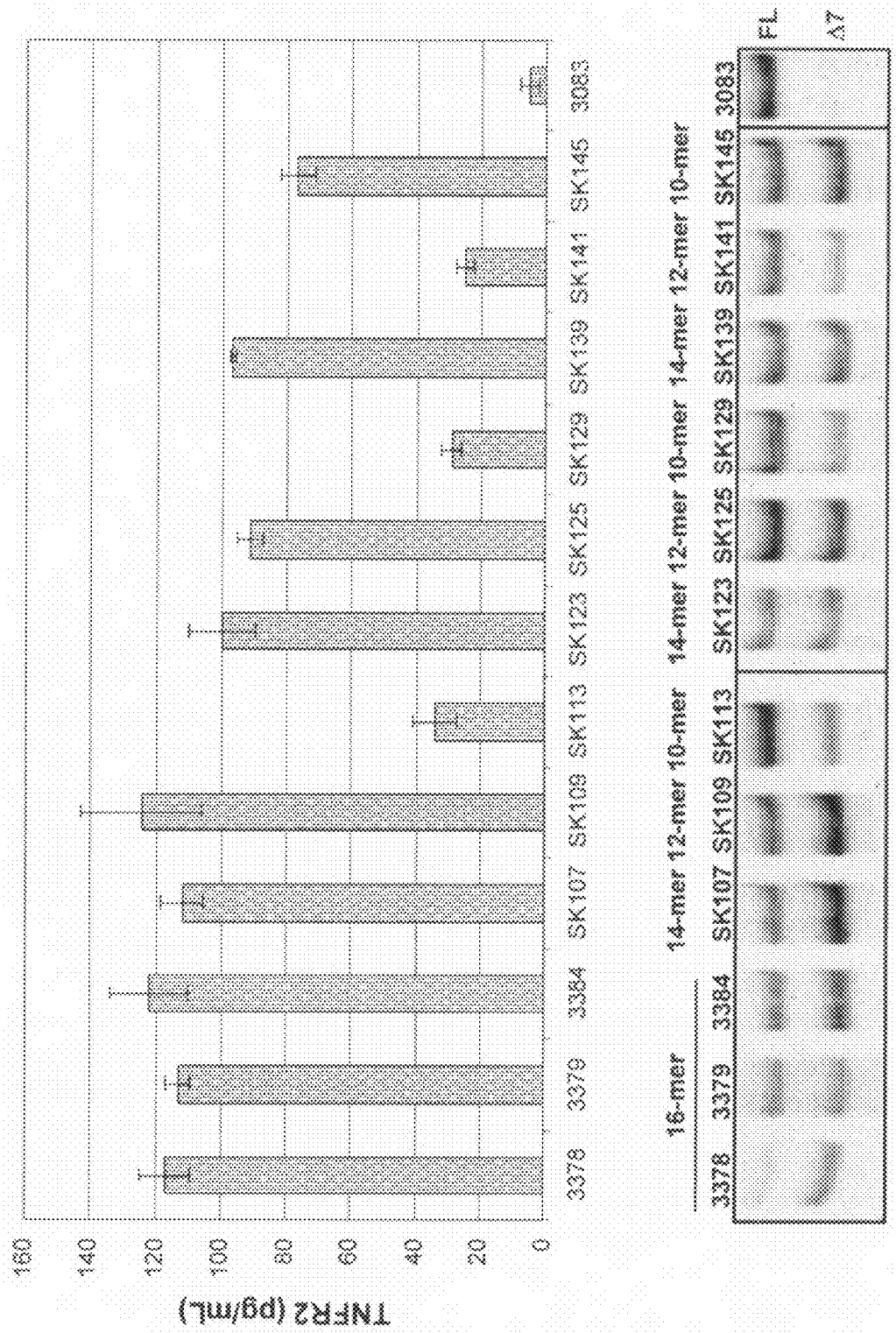

FIG. 5 depicts the splice switching ability of SSOs of different lengths. Primary human hepatocytes were transfected with the indicated SSO and TNFR2 expression analyzed by RT-PCR (top panel) and ELISA (bottom panel) as in FIG. 2. Error bars represent the standard deviation from 2 independent experiments.

Figure 6A:
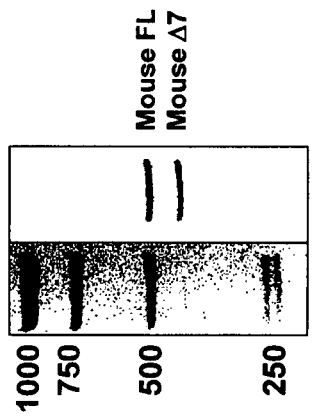
Figure 6B:
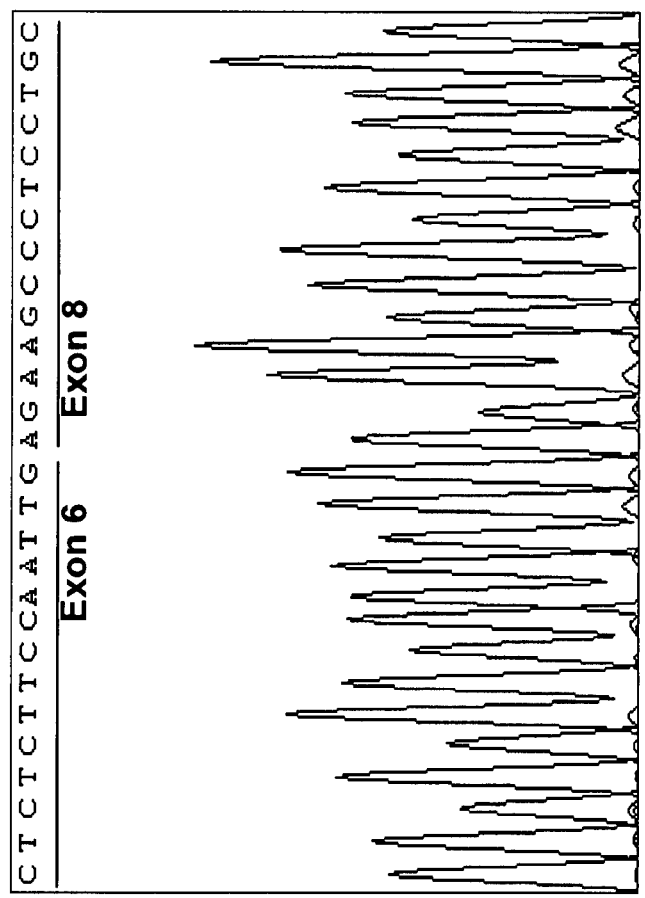

FIGS. 6A and 6B illustrate TNFR2 Δ7 mRNA induction in the livers of SSO treated mice. FIG. 6A: Total RNA from the livers of SSO 3274 treated mice were subjected to RT-PCR, and the products visualized on a 1.5% agarose gel. The sequence of the exon 6-exon 8 junction is shown in FIG. 6B.

Figure 7A:
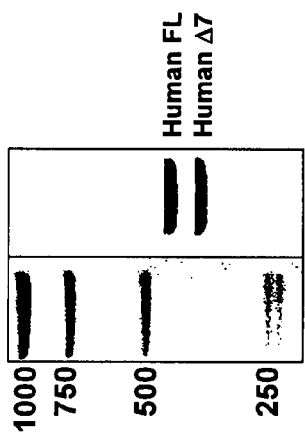
Figure 7B:
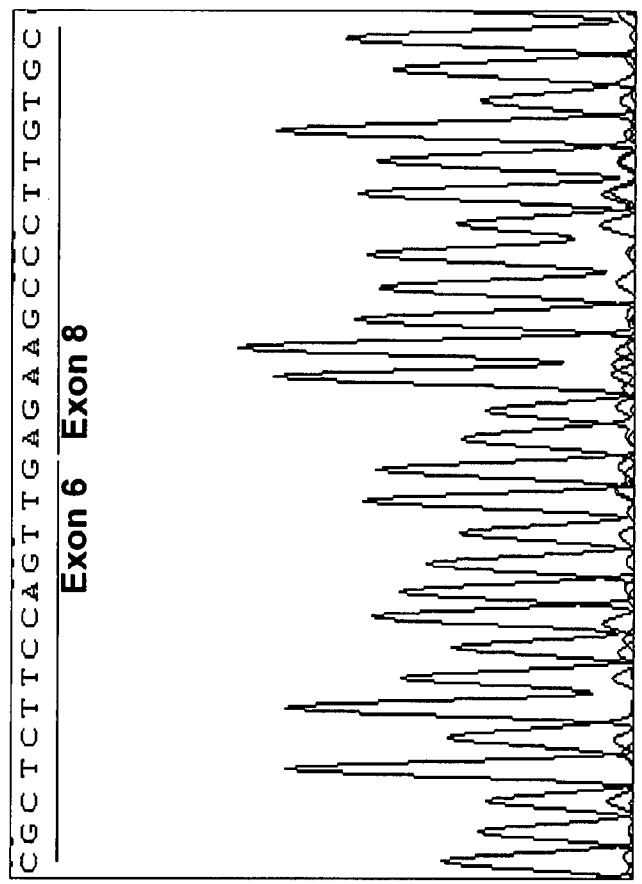

FIGS. 7A and 7B illustrate TNFR2 Δ7 mRNA induction in SSO treated primary human hepatocytes. FIG. 7A: Total RNA from SSO 3379 treated cells were subjected to RT-PCR, and the products visualized on a 1.5% agarose gel. The sequence of the exon 6-exon 8 junction is shown in FIG. 7B.

Figure 8A:
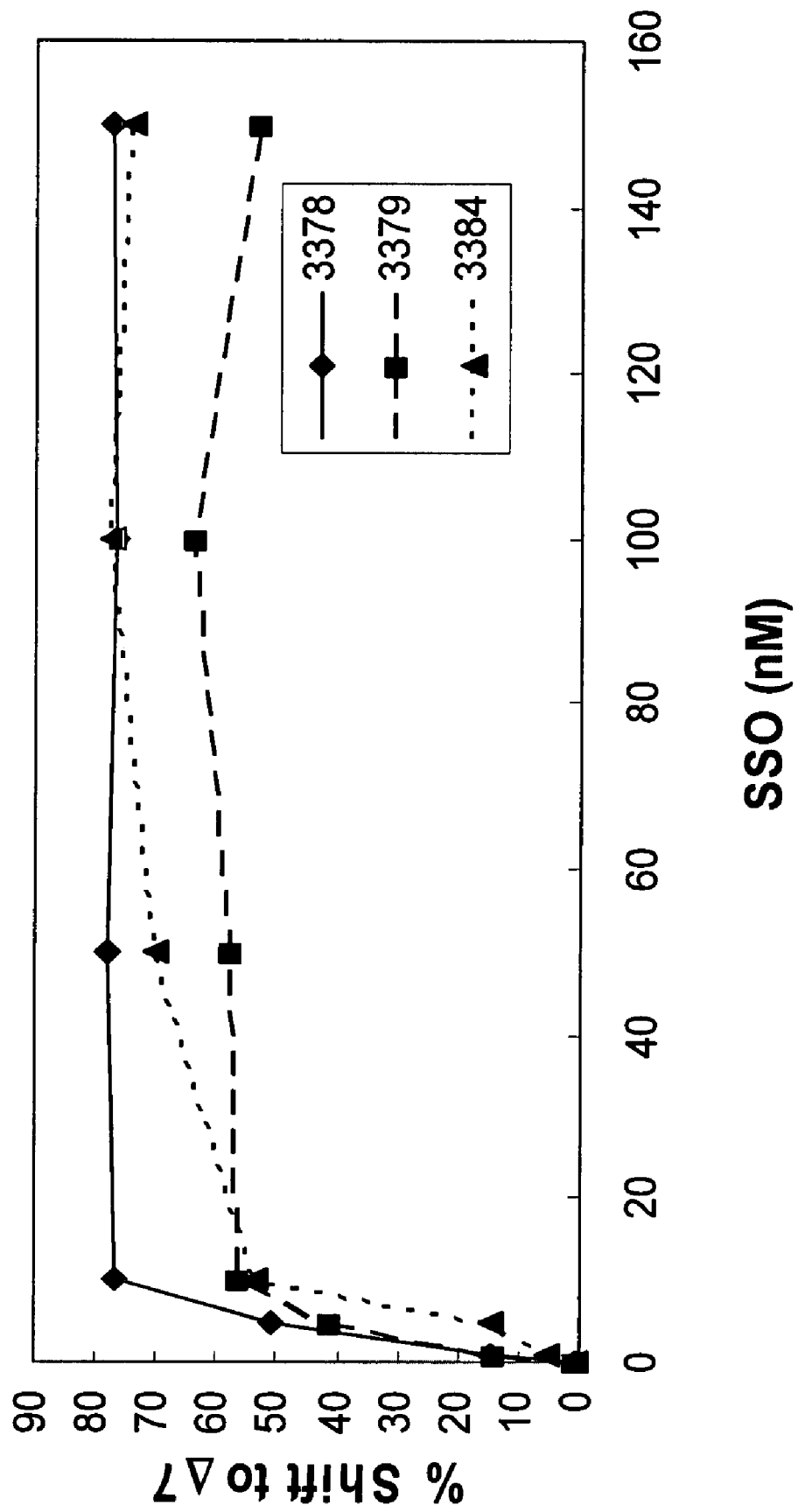
Figure 8B:
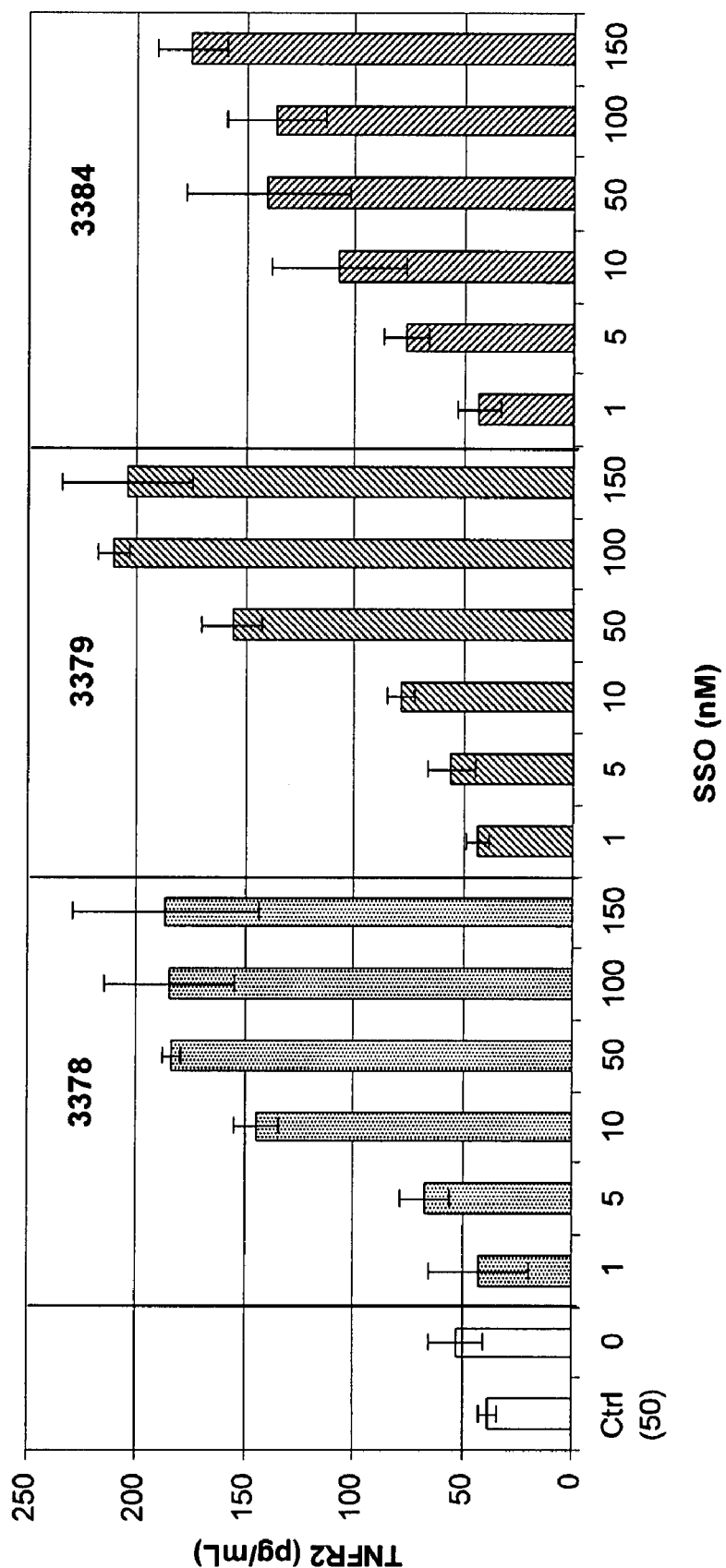

FIGS. 8A and 8B illustrate the dose dependence of TNFR2 pre-mRNA splicing shifting by SSO 3378, 3379 and 3384. Primary human hepatocytes were transfected with 1-150 nM of the indicated SSO. After ~48 hrs, the cells were harvested for total RNA, and the extracellular media was collected. FIG. 8A: Total RNA was analyzed for TNFR2 splice switching by RT-PCR using primers specific for human TNFR2. For each SSO, amount of splice switching is plotted as a function of SSO concentration. FIG. 8B: The concentration of soluble TNFR2 in the extracellular media was determined by ELISA and plotted as a function of SSO. Error bars represent the standard deviation for at least 2 independent experiments.

Figure 9:
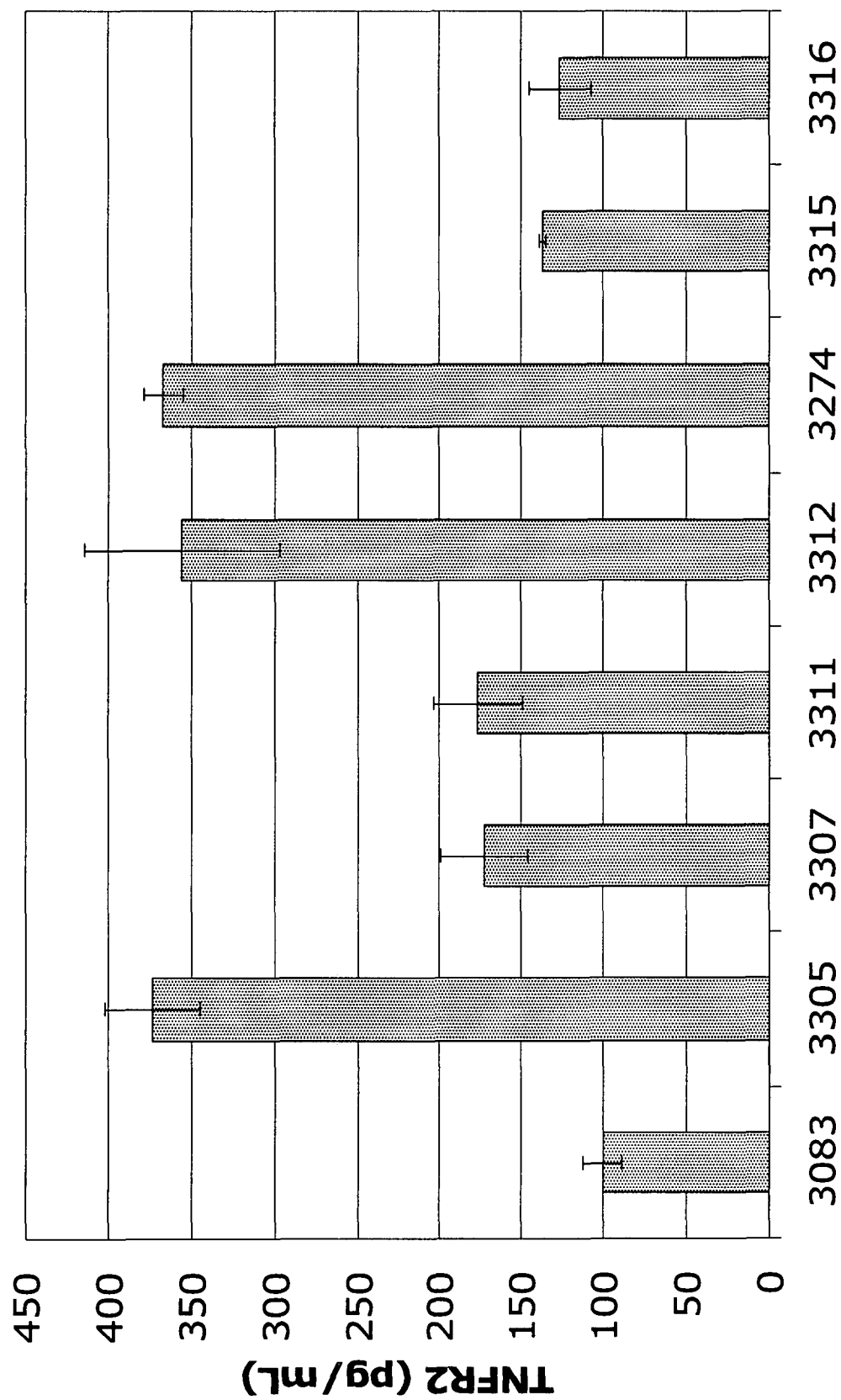

FIG. 9 graphically illustrates detection of secreted TNFR2 splice variants from L929 cells. Cells were transfected with the indicated SSOs. After 72 hrs, the extracellular media was removed and analyzed by ELISA. The data are expressed as pg soluble TNFR2 per mL.

Figure 10:
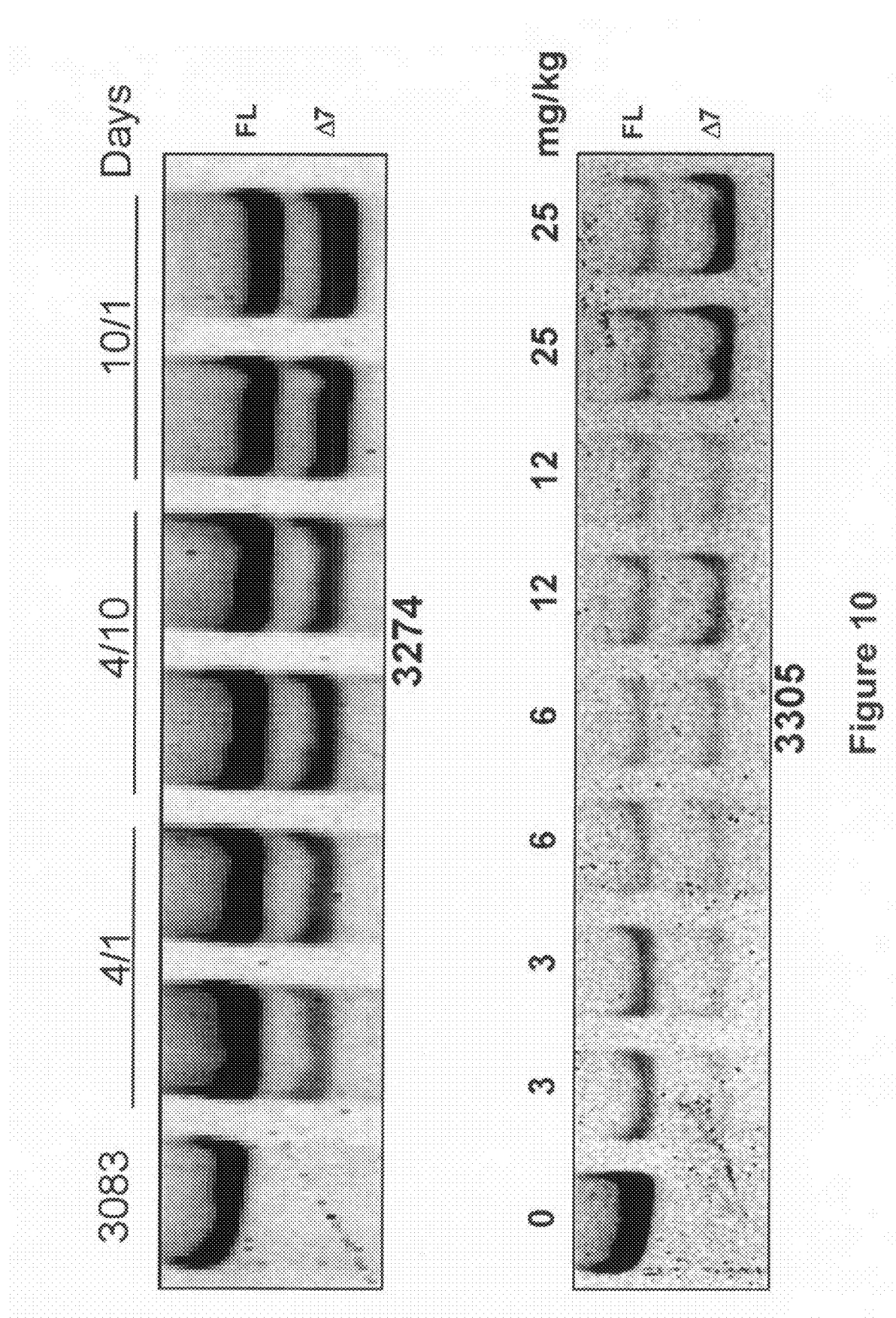

FIG. 10 shows the splicing products for intraperitoneal (i.p.) injection of SSO 3274 (top) and 3305 (bottom) in mice. SSO 3274 was injected i.p. at 25 mg/kg/day for either 4 days (4/1 and 4/10) or 10 days (10/1). Mice were sacrificed either 1 day (4/1 and 10/1) or 10 days (4/10) after the last injection and total RNA from liver was analyzed by RT-PCR for TNFR2 splice switching as described in FIG. 3. SSO 3305 was injected at the indicated dose per day for 4 days. Mice were sacrificed the next day and the livers analyzed as with 3274 treated animals.

FIGS. 11A and 11B illustrate the effect of SSO on mice. FIG. 11A: A graphical depiction of the amount of soluble TNFR2 in mouse serum 10 days after SSO treatment. Mice were injected i.p. with the indicated SSO or saline (n=5 per group) at 25 mg/kg/day for 10 days. Serum was collected 4 days before injections began and on the indicated days after the last injection. Sera was analyzed by ELISA as described in FIG. 2. FIG. 11B: The results of RT-PCR analysis of TNFR2 splice switching in livers of mice treated as described in the legend to FIG. 11A and sacrificed at 10 days.

Figure 12A:
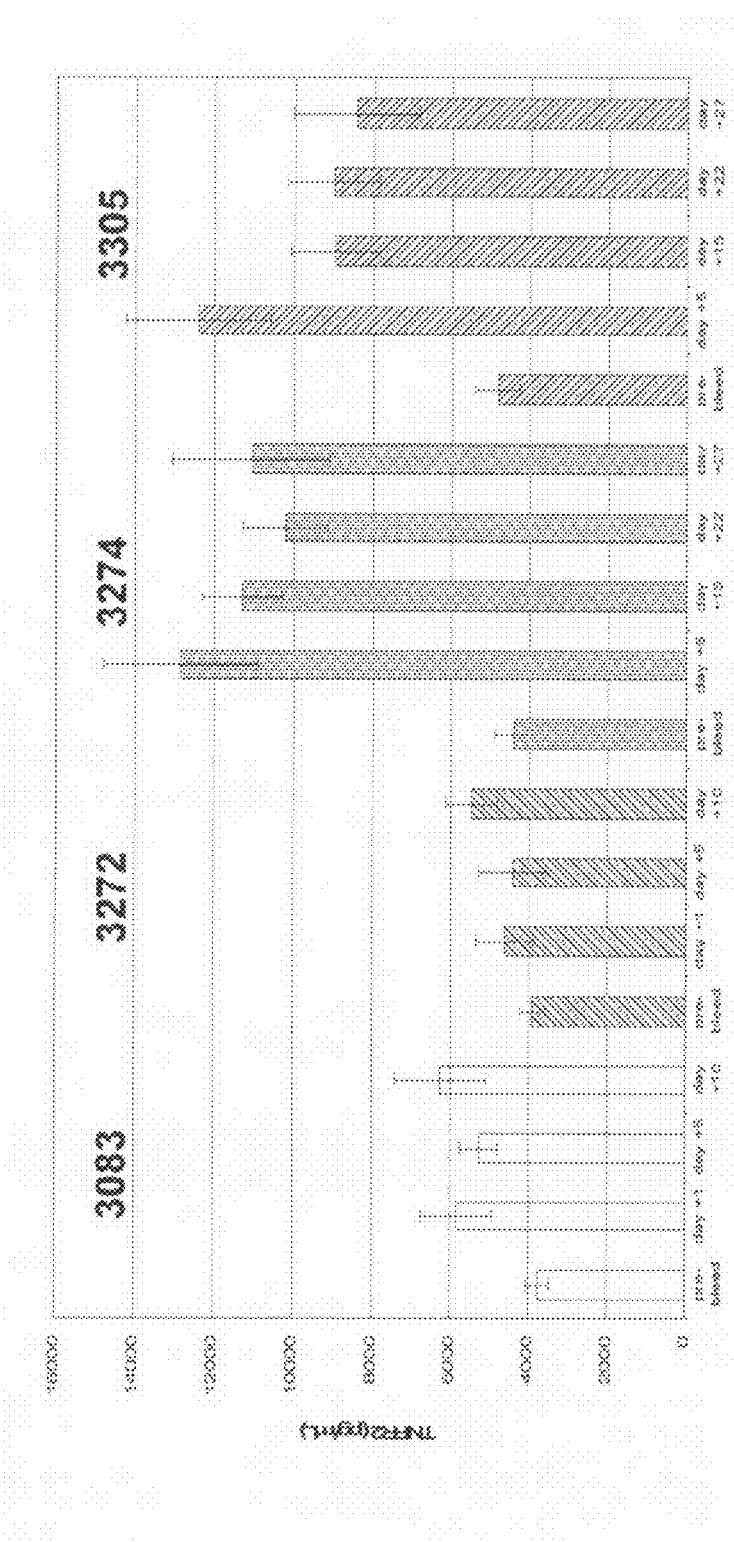
Figure 12B:
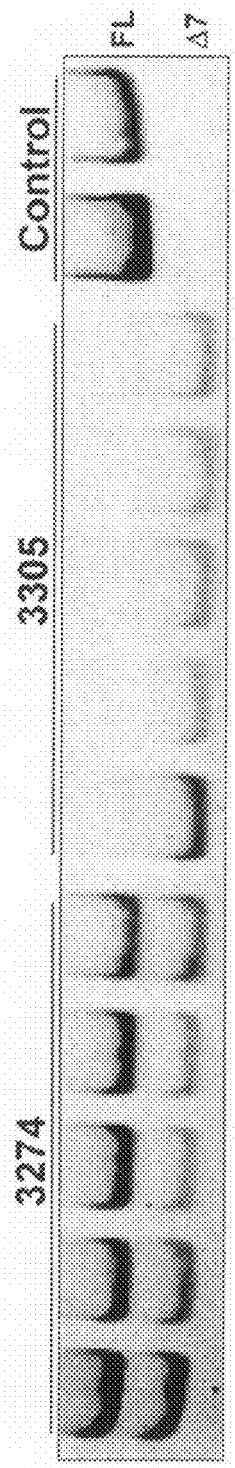

FIGS. 12A and 12B illustrate the effect of SSO on mice. FIG. 12A: A graphical depiction of the amount of soluble TNFR2 in mouse serum 27 days after SSO treatment. Mice were treated as described in FIG. 11, except that serum samples were collected until day 27 after the last injection. SSOs 3083 and 3272 are control SSOs with no TNFR2 splice switching ability. FIG. 12B: The results of RT-PCR analysis of TNFR2 splice switching in livers of mice treated as described in the legend of FIG. 12A and sacrificed at 27 days.

Figure 13A:
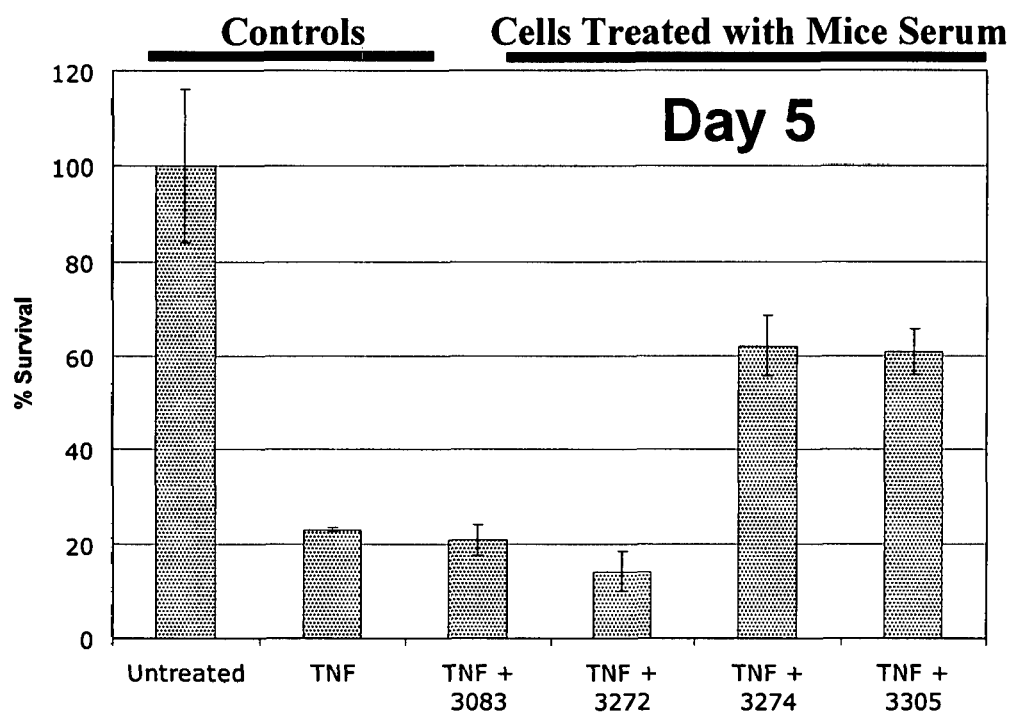
Figure 13B:
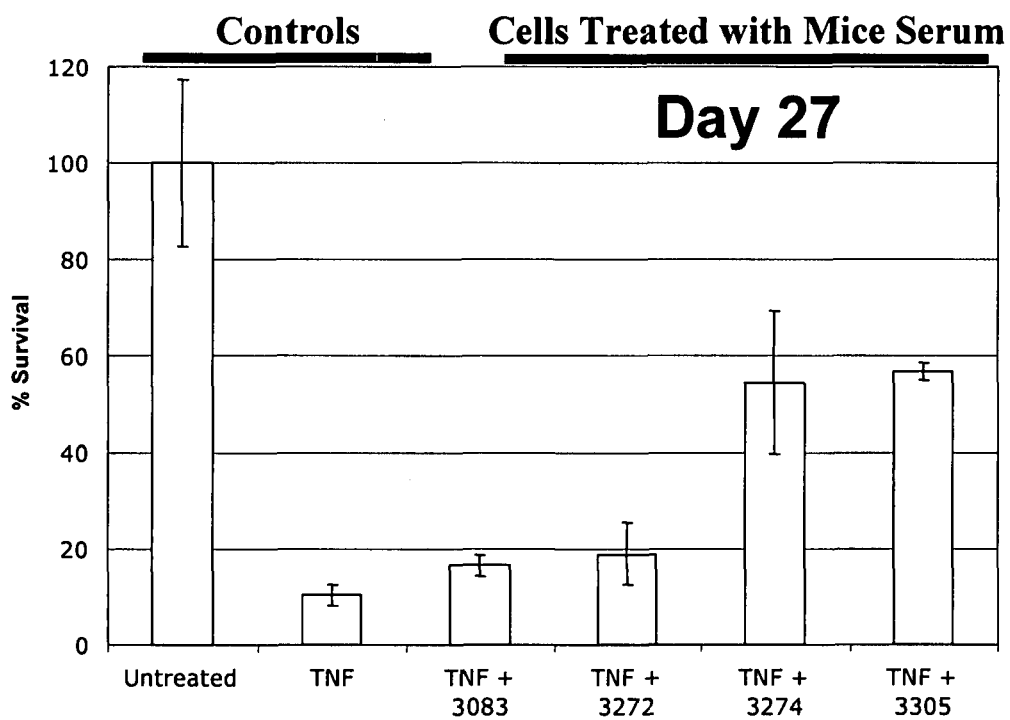

FIGS. 13A and 13B graphically depict the anti-TNF-α activity in a cell-based assay using serum from SSO treated mice, where serum samples were collected 5 days (FIG. 6A) and 27 days (FIG. 6B) after SSO treatment. L929 cells were treated with either 0.1 ng/mL TNF-α, or TNF-α plus 10% serum from mice treated with the indicated SSO. Cell viability was measured 24 hrs later and normalized to untreated cells.

Figure 14:
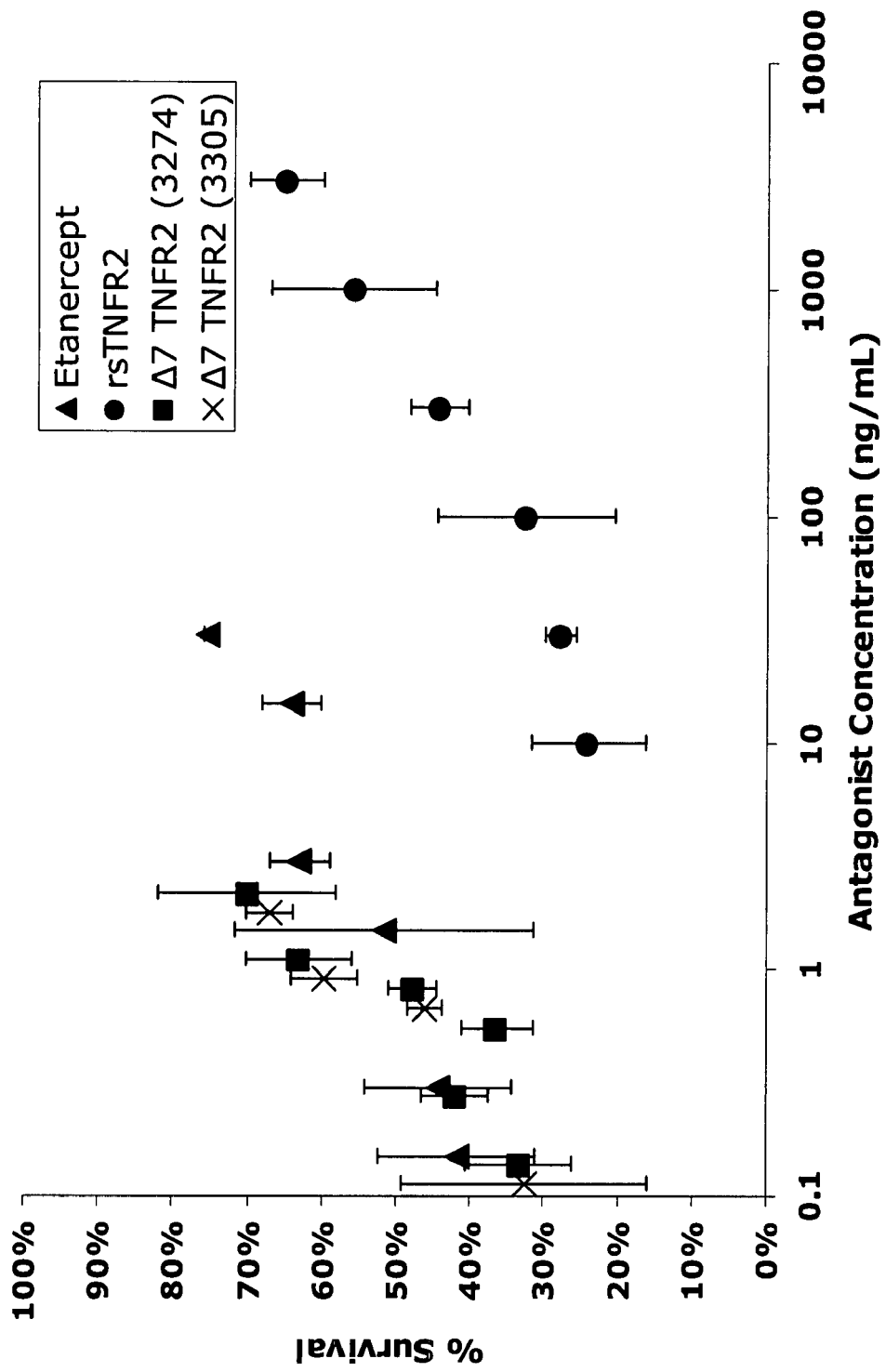

FIG. 14 graphically compares the anti-TNF-α activity of serum from the indicated SSO oligonucleotide-treated mice to recombinant soluble TNFR2 (rsTNFR2) extracellular domain from Sigma® and to Enbrel® using the cell survival assay described in FIG. 13.

Figure 15A:
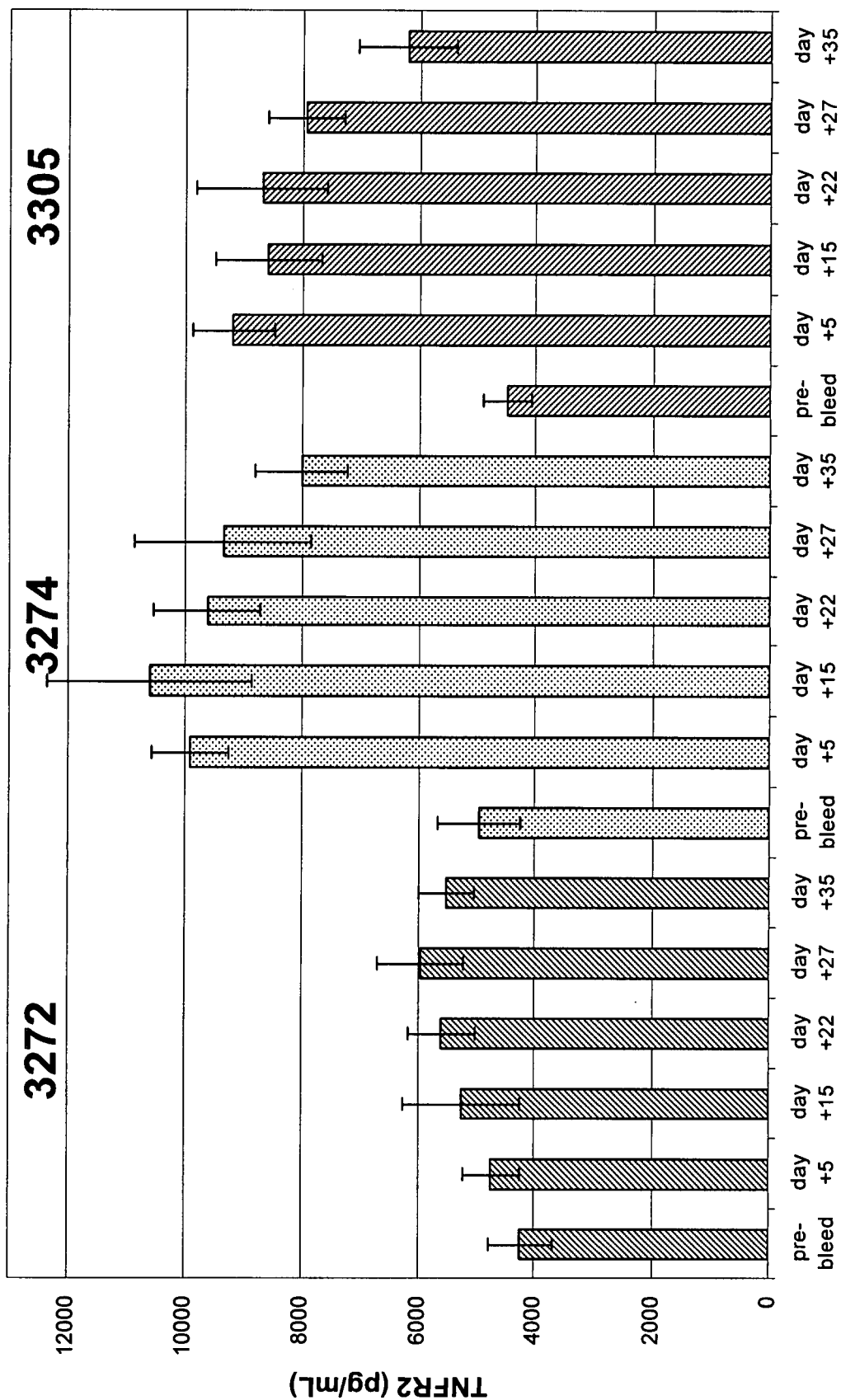
Figure 15B:
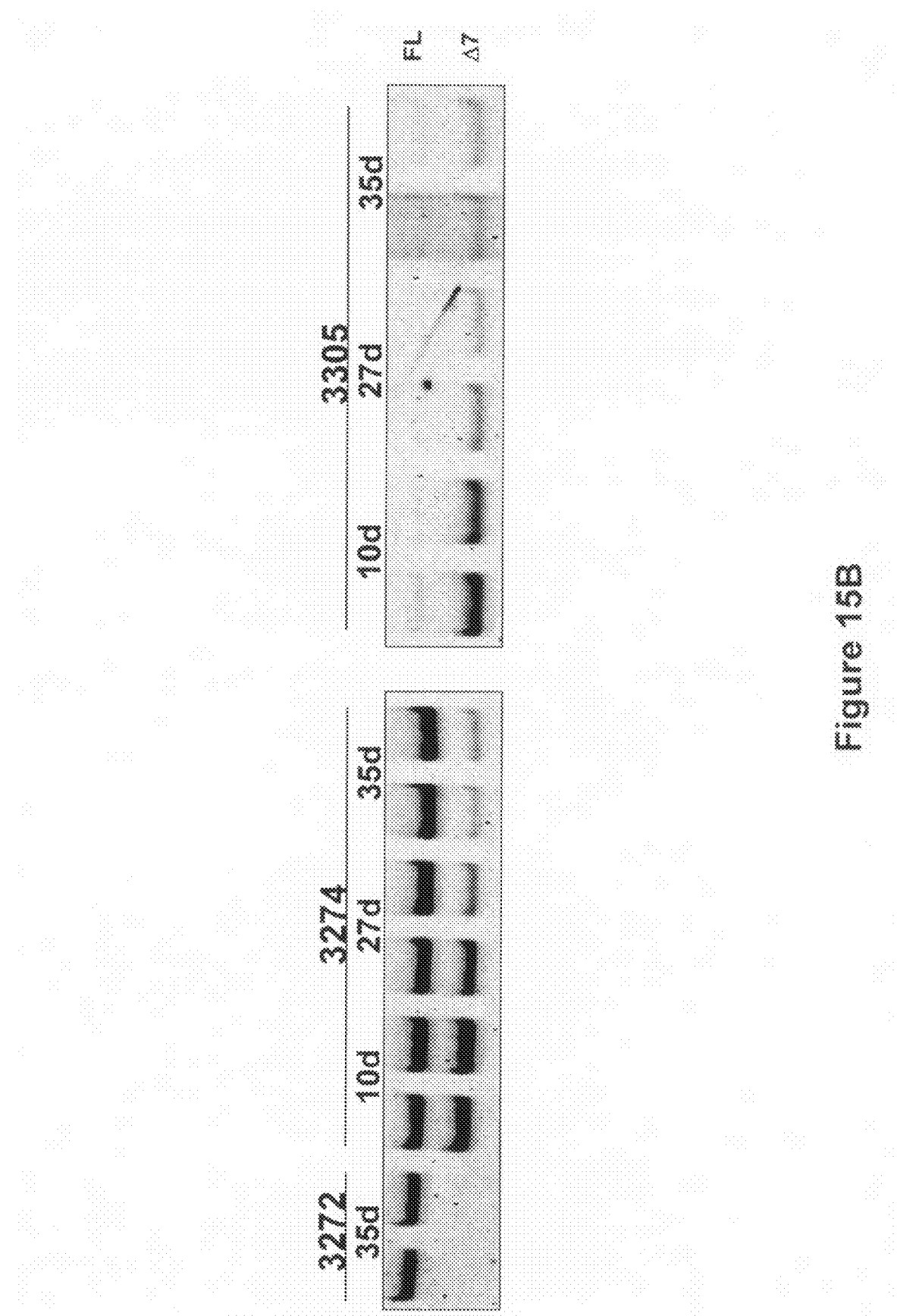

FIGS. 15A and 15B compare the stability of muTNFR2 Δ7 protein (FIG. 15A) and mRNA (FIG. 15B). Mice were injected at 25 mg/kg/day daily with either SSO 3272, SSO 3274 or SSO 3305 (n=5). Mice were bled on the indicated day after the last injection and the serum TNFR2 concentration was measured. Total RNA from mice sacrificed on the indicated day after the last injection of SSO was subjected to RT-PCR as described in FIG. 10.

Figure 16:
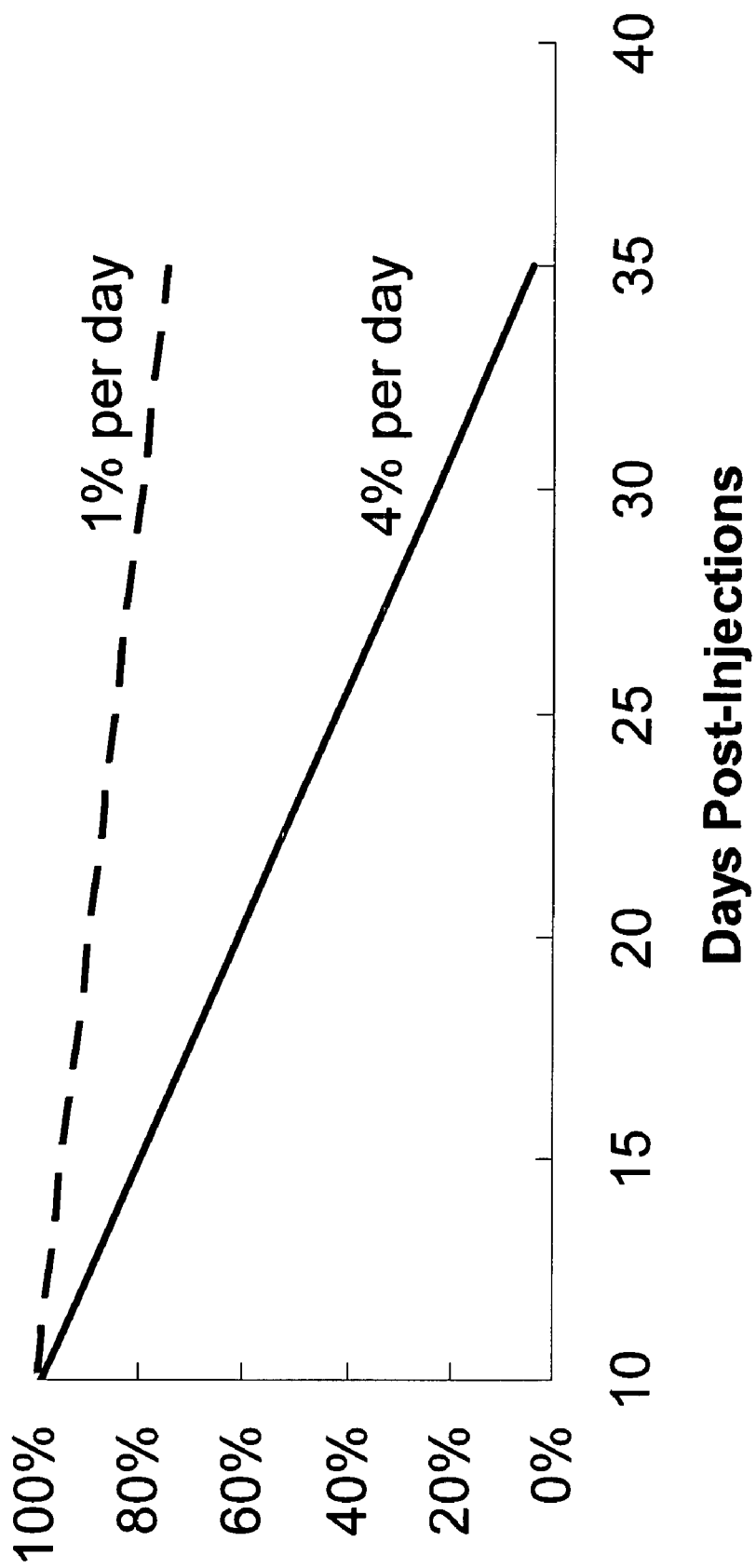

FIG. 16 plots TNFR2 Δ7 protein (dashed line) and mRNA (solid line) levels over time, as a percentage of the amount of protein or mRNA, respectively, 10 days after the last injection.

Figure 17:
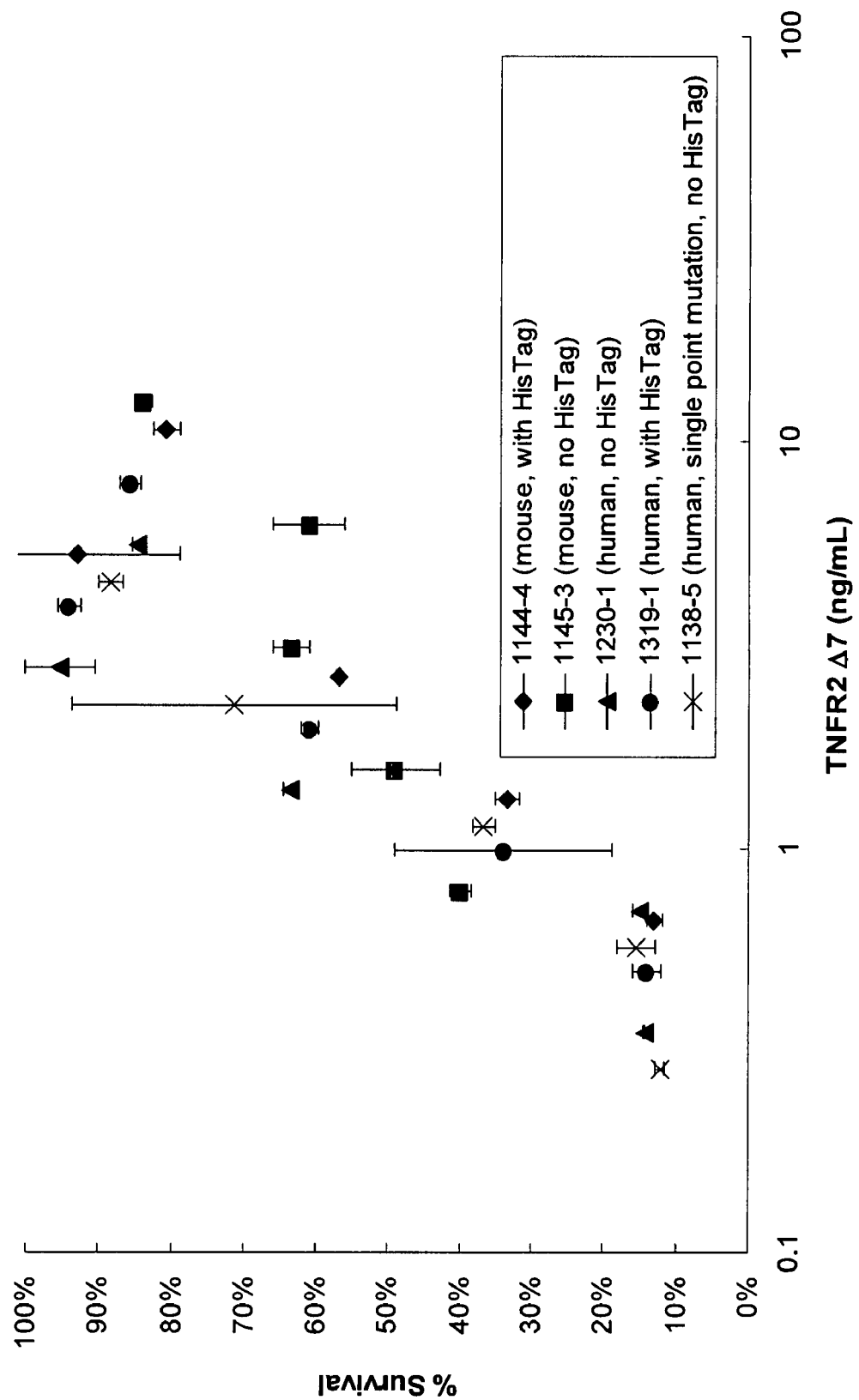

FIG. 17 graphically illustrates the dose dependant anti-TNF-α activity of TNFR2 Δ7 expressed in HeLa cells after transfection with TNFR2 Δ7 mammalian expression plasmids. HeLa cells were transfected with the indicated mouse or human TNFR2 Δ7 plasmid and extracellular media was collected after 48 hrs. The TNFR2 Δ7 concentration in the media was determined by ELISA and serial dilutions were prepared. These dilutions were assayed for anti-TNF-α activity by the L929 cytoxicity assay as in FIG. 14.

Figure 18:
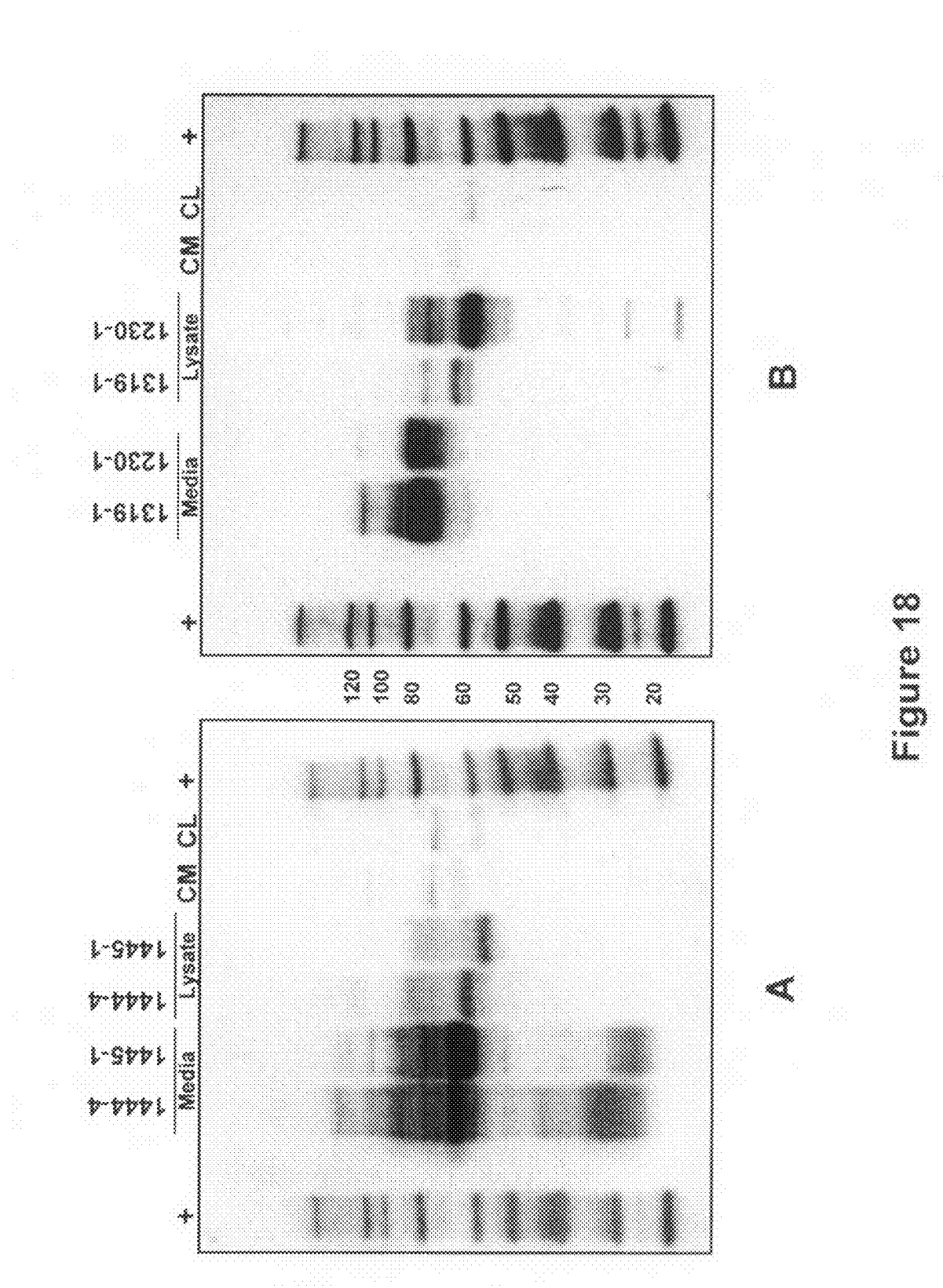

FIG. 18 shows expressed mouse (A) and human (B) TNFR2 Δ7 protein isolated by polyacrylamide gel electrophoresis (PAGE). HeLa cells were transfected with the indicated plasmid. After ~48 hrs, the extracellular media was collected and concentrated, and cells were collected in RIPA lysis buffer. The proteins in the samples were separated by PAGE and a western blot was performed using a C-terminal TNFR2 primary antibody (Abcam) that recognizes both the human and mouse TNFR2 Δ7 proteins. Media, extracellular media samples from HeLa cells transfected with the indicated plasmid; Lysate, cell lysate from Hela cells transfected with the indicated plasmid. CM, control media from untransfected HeLa cells; CL, control cell lysates from untransfected HeLa cells. +, molecular weight markers (kDal).

Figure 19:
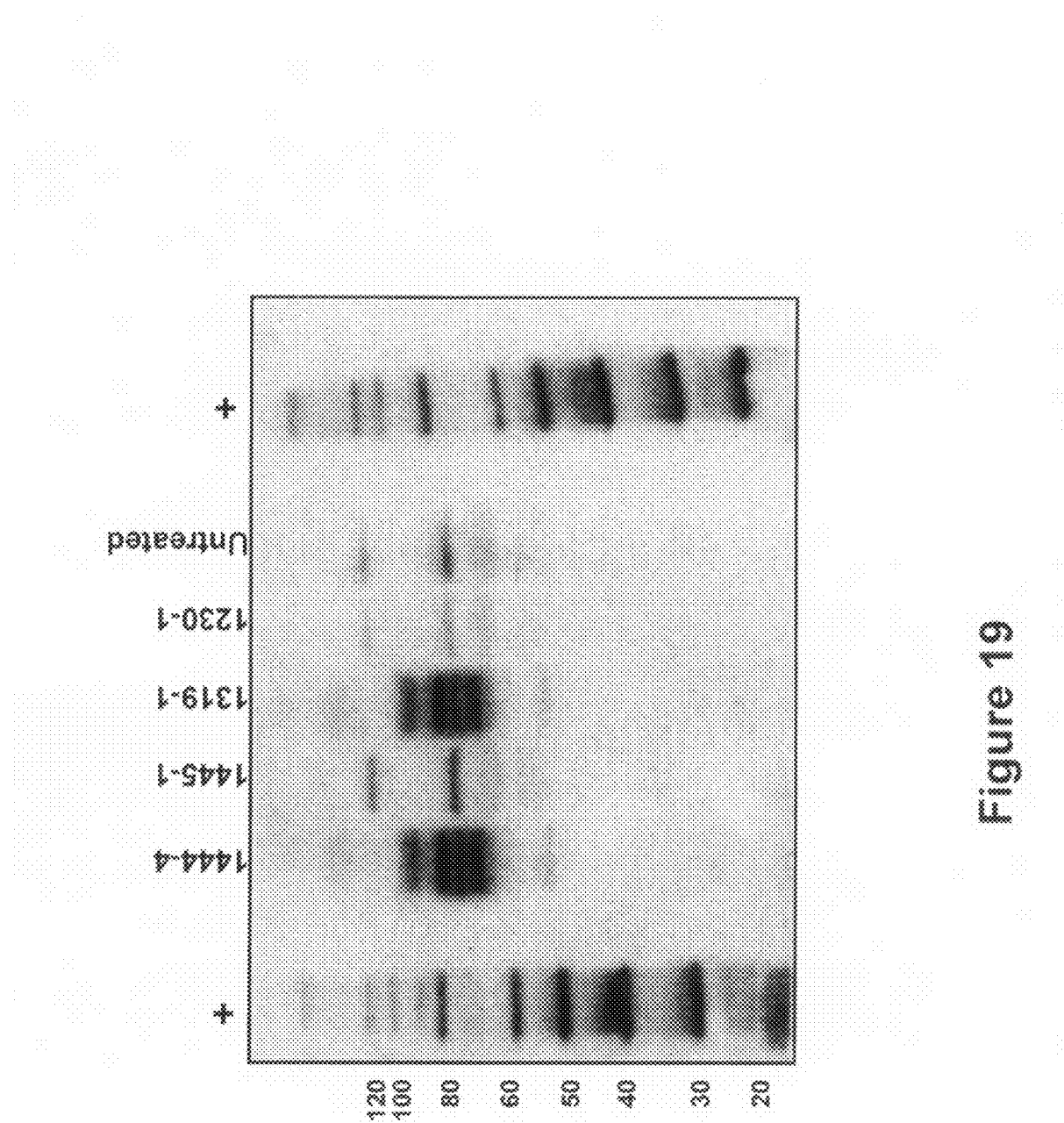

FIG. 19 shows purified His-tagged human and mouse TNFR2 Δ7. Unconcentrated extracellular media containing the indicated TNFR2 Δ7 protein was prepared as in FIG. 18. Approximately 32 mL of the media was applied to a 1 mL HisPur cobalt spin column (Pierce), and bound proteins were eluted in 1 mL buffer containing 150 mM imidazole. Samples of each were analyzed by PAGE and western blot was performed as in FIG. 18. The multiple bands in lanes 1144-4 and 1319-1 represent variably glycosylated forms of TNFR2 Δ7.

DETAILED DESCRIPTION OF THE INVENTION

Definitions:

As used herein, the terms "tumor necrosis factor receptor", "TNF receptor", and "TNFR" refer to proteins having amino acid sequences of or which are substantially similar to native mammalian TNF receptor sequences, and which are capable of binding TNF molecules. In this context, a "native" receptor or gene for such a receptor, means a receptor or gene that occurs in nature, as well as the naturally-occurring allelic variations of such receptors and genes.

The term "mature" as used in connection with a TNFR means a protein expressed in a form lacking a leader or signal sequence as may be present in full-length transcripts of a native gene.

The nomenclature for TNFR proteins as used herein follows the convention of naming the protein (e.g., TNFR2) preceded by a species designation, e.g., hu (for human) or mu (for murine), followed by a Δ (to designate a deletion) and the number of the exon(s) deleted. For example, huTNFR2 Δ7 refers to human TNFR2 lacking exon 7. In the absence of any species designation, TNFR refers generically to mammalian TNFR.

The term "secreted" means that the protein is soluble, i.e., that it is not bound to the cell membrane. In this context, a form will be soluble if using conventional assays known to one of skill in the art most of this form can be detected in fractions that are not associated with the membrane, e.g., in cellular supernatants or serum.

The term "stable" means that the secreted TNFR form is detectable using conventional assays by one of skill in the art, such as, western blots, ELISA assays in harvested cells, cellular supernatants, or serum.

As used herein, the terms "tumor necrosis factor" and "TNF" refer to the naturally-occuring protein ligands that bind to TNF receptors. TNF includes, but is not limited to, TNF-α and TNF-β.

As used herein, the term "an inflammatory disease or condition" refers to a disease, disorder, or other medical condition that at least in part results from or is aggravated by the binding of TNF to its receptor. Such diseases or conditions include, but are not limited to, those associated with increased levels of TNF, increased levels of TNF receptor, or increased sensitization or deregulation of the corresponding signaling pathway. The term also encompasses diseases and conditions for which known TNF antagonists have been shown useful. Examples of inflammatory diseases or conditions include, but are not limited to, rheumatoid arthritis, juvenile rheumatoid arthritis, psoriasis, psoriatic arthritis, ankylosing spondylitis, inflammatory bowel disease (including Crohn's disease and ulcerative colitis), hepatitis, sepsis, alcoholic liver disease, and non-alcoholic steatosis.

As used herein, the term "hepatitis" refers to a gastroenterological disease, condition, or disorder that is characterized, at least in part, by inflammation of the liver. Examples of hepatitis include, but are not limited to, hepatitis associated with hepatitis A virus, hepatitis B virus, hepatitis C virus, or liver inflammation associated with ischemia/reperfusion.

As used herein, the term "TNF antagonist" means that the protein is capable of measurable inhibition of TNF-mediated cytotoxicity using standard assays as are well known in the art. (See, e.g., Example 1 below, L929 cytotoxicity assay).

The term "binds TNF" means that the protein can bind detectable levels of TNF, preferably TNF-α, as measured by standard binding assays as are well known in the art (See, e.g., U.S. Pat. No. 5,945,397 to Smith, cols. 16-17). Preferably, receptors of the present invention are capable of binding greater than 0.1 nmoles TNF-α/nmole receptor, and more preferably, greater than 0.5 nmoles TNF-α/nmole receptor using standard binding assays.

As used herein, the term "regulatory element" refers to a nucleotide sequence involved in an interaction of molecules that contributes to the functional regulation of a nucleic acid, including but not limited to, replication, duplication, transcription, splicing, translation, or degradation of the nucleic acid. The regulation may be enhancing or inhibitory in nature.

Regulatory elements known in the art include, for example, transcriptional regulatory sequences such as promoters and enhancers. A promoter is a DNA region that is capable under certain conditions of aiding the initiation of transcription of a coding region usually located downstream (in the 3' direction) from the promoter.

As used herein, the term "operably linked" refers to a juxtaposition of genetic elements, wherein the elements are in a relationship permitting them to operate in the expected manner. For example, a promoter is operably linked to a coding region if the promoter helps initiate transcription of the coding sequence. As long as this functional relationship is maintained, there can be intervening residues between the promoter and the coding region.

As used herein, the terms "transformation" or "transfection" refer to the insertion of an exogenous nucleic acid into a cell, irrespective of the method used for the insertion, for example, lipofection, transduction, infection or electroporation. The exogenous nucleic acid can be maintained as a non-integrated vector, for example, a plasmid, or alternatively, can be integrated into the cell's genome.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids. or viral vectors (e.g., replication defective retroviruses, adenoviruses and adeno-associated viruses).

As used herein, the term "isolated protein" refers to a protein or polypeptide that is not naturally-occurring and/or is separated from one or more components that are naturally associated with it.

As used herein, the term "isolated nucleic acid" refers to a nucleic acid that is not naturally-occurring and/or is in the form of a separate fragment or as a component of a larger construct, which has been derived from a nucleic acid isolated at least once in substantially pure form, i.e., free of contaminating endogenous materials, and in a quantity or concentration enabling identification and manipulation by standard biochemical methods, for example, using a cloning vector.

As used herein the term "purified protein" refers to a protein that is present in the substantial absence of other protein. However, such purified proteins can contain other proteins added as stabilizers, carriers, excipients, or co-therapeutics. The term "purified" as used herein preferably means at least 80% by dry weight, more preferably in the range of 95-99% by weight, and most preferably at least 99.8% by weight, of protein present, excluding proteins added as stabilizers, carriers, excipients, or co-therapeutics.

As used herein, the term "altering the splicing of a pre-mRNA" refers to altering the splicing of a cellular pre-mRNA target resulting in an altered ratio of splice products. Such an alteration of splicing can be detected by a variety of techniques well known to one of skill in the art. For example, RT-PCR on total cellular RNA can be used to detect the ratio of splice products in the presence and the absence of an SSO.

As used herein, the term "complementary" is used to indicate a sufficient degree of complementarity or precise pairing such that stable and specific binding occurs between an oligonucleotide and a DNA or RNA containing the target sequence. It is understood in the art that the sequence of an oligonucleotide need not be 100% complementary to that of its target. For example, for an SSO there is a sufficient degree of complementarity when, under conditions which permit splicing, binding to the target will occur and non-specific binding will be avoided.

Proteins:

One embodiment of the present invention is a protein, either full length or mature, which is encoded by a cDNA derived from a mammalian TNFR gene, and in the cDNA exon 6 is followed directly by exon 8 and as a result lacks exon 7. Furthermore the protein can bind TNF, preferably TNF-α, and can act as a TNF, preferably TNF-α, antagonist. Preferably, TNFR of the present invention is capable of inhibition of TNF-mediated cytotoxicity to a greater extent than the soluble extracellular domain alone, and more preferably, to an extent comparable to or greater than TNFR:Fc. Mammalian TNFR according to the present disclosure includes, but is not limited to, human, primate, murine, canine, feline, bovine, ovine, equine, and porcine TNFR. Furthermore, mammalian TNFR according to the present disclosure includes, but is not limited to, a protein sequence that results from one or more single nucleotide polymorphisms, such as for example those disclosed in EP Pat. Appl. 1,172,444, as long as the protein retains a comparable biological activity to the reference sequence with which it is being compared.

In one embodiment, the mammalian TNFR is a mammalian TNFR1, preferably a human TNFR1. For human TNFR1 two non-limiting examples of this embodiment are given by huTNFR1 Δ7 which includes the signal sequence as shown in SEQ ID No: 6 and mature huTNFR1 Δ7 (amino acids 30-417 of SEQ ID No: 6) which lacks the signal sequence. The sequences of these huTNFR1 Δ7 proteins are either amino acids 1-208 of wild type human TNFR1 (SEQ ID No: 2) which includes the signal sequence or 30-208 of wild type human TNFR1 for mature huTNFR1 Δ7 which lacks the signal sequence, and in either case is followed immediately by amino acids 247-455 of wild type human TNFR1.

In another preferred embodiment, the mammalian TNFR is a mammalian TNFR2, most preferably a human TNFR2. For human TNFR2 two non-limiting examples of this embodiment are given by huTNFR2 Δ7 which includes the signal sequence as shown in SEQ ID No: 10 or mature huTNFR2 Δ7 (amino acids 23-435 of SEQ ID No: 10) which lacks the signal sequence. The sequences of these huTNFR2 Δ7 proteins are either amino acids 1-262 of wild type human TNFR2 (SEQ ID No: 4) which includes the signal sequence or 23-262 of wild type human TNFR2 for mature huTNFR2 Δ7 which lacks the signal sequence, followed in either case by the amino acid glutamate, because of the creation of a unique codon at the exon 6-8 junction, which is followed by amino acids 290-461 of wild type human TNFR2.

The proteins of the present invention also include those proteins that are chemically modified. Chemical modification of a protein refers to a protein where at least one of its amino acid residues is modified by either natural processes, such as processing or other post-translational modifications, or by chemical modification techniques known in the art. Such modifications include, but are not limited to, acetylation, acylation, amidation, ADP-ribosylation, glycosylation, methylation, pegylation, prenylation, phosphorylation, or cholesterol conjugation.

Nucleic Acids:

One embodiment of the present invention is a nucleic acid that encodes a protein, either full length or mature, which is encoded by a cDNA derived from a mammalian TNFR gene, and in the cDNA exon 6 is followed directly by exon 8 and as a result lacks exon 7.

Such sequences are preferably provided in the form of an open reading frame uninterrupted by internal nontranslated sequences, or introns, which are typically present in eukaryotic genes. Genomic DNA containing the relevant sequences can also be used. In one embodiment, the nucleic acid is either an mRNA or a cDNA. In another embodiment, it is genomic DNA.

In one embodiment, the mammalian TNFR is a mammalian TNFR1. For this embodiment, the mammalian TNFR1 is preferably a human TNFR1. For human TNFR1, two non-limiting examples of this embodiment are nucleic acids which encode the huTNFR1 Δ7 which includes the signal sequence as shown in SEQ ID No: 6 and mature huTNFR1 Δ7 (amino acids 30-417 of SEQ ID No: 6) which lacks the signal sequence. Preferably, the sequences of these huTNFR1 Δ7 nucleic acids are nucleotides 1-1251 of SEQ ID No: 5, which includes the signal sequence and nucleotides 88-1251 of SEQ ID No: 5 which lacks the signal sequence. The sequences of these huTNFR1 Δ7 nucleic acids are either nucleotides 1-625 of wild type human TNFR1 (SEQ ID No: 1) which includes the signal sequence or 88-625 of wild type human TNFR1 for mature huTNFR2 Δ7 which lacks the signal sequence, and in either case is followed immediately by amino acids 740-1368 of wild type human TNFR1.

In another preferred embodiment, the mammalian TNFR is a mammalian TNFR2, most preferably a human TNFR2. For human TNFR2, two non-limiting examples of this embodiment are nucleic acids which encode the huTNFR2 Δ7 which includes the signal sequence as shown in SEQ ID No: 10 or mature huTNFR2 Δ7 (amino acids 23-435 of SEQ ID No: 10) which lacks the signal sequence. Preferably, the sequences of these huTNFR2 Δ7 nucleic acids are nucleotides 1-1305 of SEQ ID No: 9 which includes the signal sequence and nucleotides 67-1305 of SEQ ID No: 9 which lacks the signal sequence. The sequences of these huTNFR2 Δ7 nucleic acids are either nucleotides 1-787 of wild type human TNFR2 (SEQ ID No: 3) which includes the signal sequence or 67-787 of wild type human TNFR2 for mature huTNFR2 Δ7 which lacks the signal sequence, and in either case is followed immediately by amino acids 866-1386 of wild type human TNFR2.

The bases of the nucleic acids of the present invention can be the conventional bases cytosine, guanine, adenine and uracil or thymidine. Alternatively, modified bases can be used. Other suitable bases include, but are not limited to, 5-methylcytosine ($^{Me}C$), isocytosine, pseudoisocytosine, 5-bromouracil, 5-propynyluracil, 5-propyny-6,5-methylthiazoleuracil, 6-aminopurine, 2-aminopurine, inosine, 2,6-diaminopurine, 7-propyne-7-deazaadenine, 7-propyne-7-deazaguanine, 2-chloro-6-aminopurine and 9-(aminoethoxy) phenoxazine.

Suitable nucleic acids of the present invention include numerous alternative chemistries. For example, suitable nucleic acids of the present invention include, but are not limited to, those wherein at least one of the internucleotide bridging phosphate residues is a modified phosphate, such as phosphorothioate, methyl phosphonate, methyl phosphonothioate, phosphoromorpholidate, phosphoropiperazidate, and phosphoroamidate. In another non-limiting example, suitable nucleic acids of the present invention include those wherein at least one of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl).

Nucleic acids of the present invention also include, but are not limited to, those wherein at least one, of the nucleotides is a nucleic acid analogue. Examples of such analogues include, but are not limited to, hexitol (HNA) nucleotides, 2'O-4'C-linked bicyclic ribofuranosyl (LNA) nucleotides, peptide nucleic acid (PNA) analogues, N3'→P5' phosphoramidate analogues, phosphorodiamidate morpholino nucleotide analogues, and combinations thereof.

Nucleic acids of the present invention include, but are not limited to, modifications of the nucleic acids involving chemically linking to the nucleic acids one or more moieties or conjugates. Such moieties include, but are not limited to, lipid moieties such as a cholesterol moiety, cholic acid, a thioether, e.g. hexyl-S-tritylthiol, a thiocholesterol, an aliphatic chain, e.g., dodecandiol or undecyl residues, a phospholipids, e.g., di-hexadecyl-rac-glycerol or triethylammonium 1,2-di-O-hexadecyl-rac-glycero-3-H-phosphonate, a polyamine or a polyethylene glycol chain, an adamantane acetic acid, a palmityl moiety, an octadecylamine or hexylamino-carbonyl-oxycholesterol moiety.

Pharmaceutical Compositions and Preparations:

Other embodiments of the invention are pharmaceutical compositions comprising the foregoing proteins and nucleic acids.

The nucleic acids and proteins of the present invention may be admixed, encapsulated, conjugated, or otherwise associated with other molecules, molecule structures, or mixtures of compounds, as for example liposomes, receptor targeted molecules, oral, rectal, topical or other formulations, for assisting in uptake, distribution, and/or absorption.

Formulations of the present invention comprise nucleic acids and proteins in a physiologically or pharmaceutically acceptable carrier, such as an aqueous carrier. Thus formulations for use in the present invention include, but are not limited to, those suitable for parenteral administration including intra-articular, intraperitoneal, intravenous, intraarterial, subcutaneous, or intramuscular injection or infusion, as well as those suitable for topical, ophthalmic, vaginal, oral, rectal or pulmonary administration (including inhalation or insufflation of powders or aerosols, including by nebulizer, intratracheal, and intranasal delivery). The formulations may conveniently be presented in unit dosage form and may be prepared by any of the methods well known in the art. The most suitable route of administration in any given case may depend upon the subject, the nature and severity of the condition being treated, and the particular active compound which is being used.

Pharmaceutical compositions of the present invention include, but are not limited to, physiologically and pharmaceutically acceptable salts, i.e., salts that retain the desired biological activity of the parent compound and do not impart undesired toxicological properties. Examples of such salts are (a) salts formed with cations such as sodium, potassium, $NH_4^+$, magnesium, calcium, polyamines such as spermine and spermidine, etc.; (b) acid addition salts formed with inorganic acids, for example, hydrochloric acid, hydrobromic acid, sulfuric acid, phosphoric acid, nitric acid and the like; and (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, napthalenesulfonic acid, methanesulfonic acid, p-toluenesulfonic acid, napthalenedisulfonic acid, polygalacturonic acid, and the like.

The present invention provides for the use of proteins and nucleic acids as set forth above for the preparation of a medicament for treating a patient afflicted with an inflammatory disorder involving excessive activity of TNF, as discussed below. In the manufacture of a medicament according to the invention, the nucleic acids and proteins of the present invention are typically admixed with, inter alia, an acceptable carrier. The carrier must, of course, be acceptable in the sense of being compatible with other ingredients in the formulation and must not be deleterious to the patient. The carrier may be a solid or liquid. Nucleic acids and proteins of the present invention are incorporated in formulations, which may be prepared by any of the well known techniques of pharmacy consisting essentially of admixing the components, optionally including one or more accessory therapeutic ingredients.

Formulations of the present invention may comprise sterile aqueous and non-aqueous injection solutions of the active compounds, which preparations are preferably isotonic with the blood of the intended recipient and essentially pyrogen free. These preparations may contain anti-oxidants, buffers, bacteriostats, and solutes which render the formulation isotonic with the blood of the intended recipient. Aqueous and non-aqueous sterile suspensions can include, but are not limited to, suspending agents and thickening agents. The formulations may be presented in unit dose or multi-dose containers, for example, sealed ampoules and vials, and may be stored in freeze-dried (lyophilized) condition requiring only the addition of the sterile liquid carrier, for example, saline or water-for-injection immediately prior to use.

In the formulation the nucleic acids and proteins of the present invention may be contained within a particle or vesicle, such as a liposome or microcrystal, which may be suitable for parenteral administration. The particles may be of any suitable structure, such as unilamellar or plurilameller, so long as the nucleic acids and proteins of the present invention are contained therein. Positively charged lipids such as N-[1-(2,3-dioleoyloxy)propyl]-N,N,N-trimethyl-ammoniummethylsulfate, or "DOTAP," are particularly preferred for such particles and vesicles. The preparation of such lipid particles is well known (See references in U.S. Pat. No. 5,976,879 col. 6).

Expression Vectors and Host Cells:

The present invention provides expression vectors to amplify or express DNA encoding mammalian TNFR of the current invention. The present invention also provides host cells transformed with the foregoing expression vectors. Expression vectors are replicable DNA constructs which have synthetic or cDNA-derived DNA fragments encoding mammalian TNFR or bioequivalent analogues operably linked to suitable transcriptional or translational regulatory elements derived from mammalian, microbial, viral, or insect genes. A transcriptional unit generally comprises an assembly of (a) a genetic element or elements having a regulatory role in gene expression, such as, transcriptional promoters or enhancers, (b) a structural or coding sequence which is transcribed into mRNA and translated into protein, and (c) appropriate transcription and translation initiation and termination sequences. Such regulatory elements can include an operator sequence to control transcription, and a sequence encoding suitable mRNA ribosomal binding sites. The ability to replicate in a host, usually conferred by an origin of replication, and a selection gene to facilitate recognition of transformants, can additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed protein to provide a final product.

Mammalian TNFR DNA is expressed or amplified in a recombinant expression system comprising a substantially homogeneous monoculture of suitable host microorganisms, for example, bacteria such as *E. coli* or yeast such as *S. cerevisiae*, which have stably integrated (by transformation or transfection) a recombinant transcriptional unit into chromosomal DNA or carry the recombinant transcriptional unit as a component of a resident plasmid. Recombinant expression systems as defined herein will express heterologous protein either constitutively or upon induction of the regulatory elements linked to the DNA sequence or synthetic gene to be expressed.

Transformed host cells are cells which have been transformed or transfected with mammalian TNFR vectors constructed using recombinant DNA techniques. Transformed host cells ordinarily express TNFR, but host cells transformed for purposes of cloning or amplifying TNFR DNA do not need to express TNFR. Suitable host cells for expression of mammalian TNFR include prokaryotes, yeast, fungi, or higher eukaryotic cells. Prokaryotes include gram negative or gram positive organisms, for example *E. coli* or bacilli. Higher eukaryotic cells include, but are not limited to, established insect and mammalian cell lines. Cell-free translation systems can also be employed to produce mammalian TNFR using RNAs derived from the DNA constructs of the present invention. Appropriate cloning and expression vectors for use with bacterial, fungal, yeast, and mammalian cellular hosts are well known in the art.

Prokaryotic expression hosts may be used for expression of TNFR that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera *Pseudomonas, Streptomyces*, and *Staphyolococcus*, although others can also be employed as a matter of choice.

Useful expression vectors for bacterial use can comprise a selectable marker and bacterial origin of replication derived from commercially available plasmids comprising genetic elements of the well known cloning vector pBR322 (ATCC 37017). These pBR322 "backbone" sections are combined with an appropriate promoter and the structural sequence to be expressed. pBR322 contains genes for ampicillin and tetracycline resistance and thus provides simple means for identifying transformed cells. Such commercial vectors include, for example, the series of Novagen® pET vectors (EMD Biosciences, Inc., Madison, Wis.).

Promoters commonly used in recombinant microbial expression vectors include the lactose promoter system, and the $\lambda P_L$ promoter, the T7 promoter, and the T7 lac promoter. A particularly useful bacterial expression system, Novagen® pET system (EMD Biosciences, Inc., Madison, Wis.) employs a T7 or T7 lac promoter and *E. coli* strain, such as BL21(DE3) which contain a chromosomal copy of the T7 RNA polymerase gene.

TNFR proteins can also be expressed in yeast and fungal hosts, preferably from the genus *Saccharomyces*, such as *S. cerevisiae*. Yeast of other genera, such as *Pichia* or *Kluyveromyces* can also be employed. Yeast vectors will generally contain an origin of replication from the 2μ yeast plasmid or an autonomously replicating sequence (ARS), promoter, DNA encoding TNFR, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* TRP1 or URA3 gene, which provides a selection marker for a mutant strain of yeast lacking the ability to grow in tryptophan or uracil, respectively, and a promoter derived from a highly expressed yeast gene to induce transcription of a structural sequence downstream. The presence of the TRP1 or URA3 lesion in the yeast host cell genome then provides an effective environment for detecting transformation by growth in the absence of tryptophan or uracil, respectively.

Suitable promoter sequences in yeast vectors include the promoters for metallothionein, 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are well known in the art.

Preferred yeast vectors can be assembled using DNA sequences from pUC18 for selection and replication in *E. coli* (Amp$^r$ gene and origin of replication) and yeast DNA sequences including a glucose-repressible ADH2 promoter and α-factor secretion leader. The yeast α-factor leader, which directs secretion of heterologous proteins, can be inserted between the promoter and the structural gene to be expressed. The leader sequence can be modified to contain, near its 3' end, one or more useful restriction sites to facilitate fusion of the leader sequence to foreign genes. Suitable yeast transformation protocols are known to those of skill in the art.

Host strains transformed by vectors comprising the ADH2 promoter may be grown for expression in a rich medium consisting of 1% yeast extract, 2% peptone, and 1% or 4% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems are also advantageously employed to express TNFR protein. Expression of recombinant proteins in mammalian cells is particularly preferred because such proteins are generally correctly folded, appropriately modified and completely functional. Examples of suitable mammalian host cell lines include the COS-7 lines of monkey kidney cells, and other cell lines capable of expressing an appropriate vector including, for example, L cells, such as L929, C127, 3T3, Chinese hamster ovary (CHO), HeLa and BHK cell lines. Mammalian expression vectors can comprise nontranscribed elements such as an origin of replication, a suitable promoter, for example, the CMVie promoter, the chicken beta-actin promoter, or the composite hEF1-HTLV promoter, and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are known to those of skill in the art.

The transcriptional and translational control sequences in expression vectors to be used in transforming vertebrate cells can be provided by viral sources. For example, commonly used promoters and enhancers are derived from Polyoma, Adenovirus 2, Simian Virus 40 (SV40), human cytomegalovirus, such as the CMVie promoter, HTLV, such as the composite hEF1-HTLV promoter. DNA sequences derived from the SV40 viral genome, for example, SV40 origin, early and late promoter, enhancer, splice, and polyadenylation sites can be used to provide the other genetic elements required for expression of a heterologous DNA sequence.

Further, mammalian genomic TNFR promoter, such as control and/or signal sequences can be utilized, provided such control sequences are compatible with the host cell chosen.

In preferred aspects of the present invention, recombinant expression vectors comprising TNFR cDNAs are stably integrated into a host cell's DNA.

Accordingly one embodiment of the invention is a method of treating an inflammatory disease or condition by administering a stable, secreted, ligand-binding form of a TNF receptor, thereby decreasing the activity of TNF for the receptor. In another embodiment, the invention is a method of treating an inflammatory disease or condition by administering an oligonucleotide that encodes a stable, secreted, ligand-binding form of a TNF receptor, thereby decreasing the activity of TNF for the receptor. In another embodiment, the invention is a method of producing a stable, secreted, ligand-binding form of a TNF receptor.

The following aspects of the present invention discussed below apply to the foregoing embodiments.

The methods, nucleic acids, proteins, and formulations of the present invention are also useful as in vitro or in vivo tools.

Embodiments of the invention can be used to treat any condition in which the medical practitioner intends to limit the effect of TNF or a signalling pathway activated by it. In particular, the invention can be used to treat an inflammatory disease. In one embodiment, the condition is an inflammatory systemic disease, e.g., rheumatoid arthritis or psoriatic arthritis. In another embodiment, the disease is an inflammatory liver disease. Examples of inflammatory liver diseases include, but are not limited to, hepatitis associated with the hepatitis A, B, or C viruses, alcoholic liver disease, and non-alcoholic steatosis. In yet another embodiment, the inflammatory disease is a skin condition such as psoriasis.

The uses of the present invention include, but are not limited to, treatment of diseases for which known TNF antagonists have been shown useful. Three specific TNF antagonists are currently FDA-approved. The drugs are etanercept (Enbrel®), infliximab (Remicade®) and adalimumab (Humira®). One or more of these drugs is approved for the treatment of rheumatoid arthritis, juvenile rheumatoid arthritis, psoriasis, psoriatic arthritis, ankylosing spondylitis, and inflammatory bowel disease (Crohn's disease or ulcerative colitis).

Protein Expression and Purification:

When mammalian or insect cells are used, properly expressed TNFR protein will be secreted into the extracellular media. The protein is recovered from the media, and is concentrated and is purified using standard biochemical techniques. After expression in mammalian cells by lentiviral or AAV transduction, plasmid transfection, or any similar procedure, or in insect cells after baculoviral transduction, the extracellular media of these cells is concentrated using concentration filters with an appropriate molecular weight cutoff, such as Amicon® filtration units. To avoid loss of TNFR protein, the filter should allow proteins to flow through that are at or below 50 kDal.

When TNFR protein is expressed in bacterial culture it can be purified by standard biochemical techniques. Bacteria are lysed, and the cellular extract containing the TNFR is desalted and is concentrated.

In either case, the TNFR protein is preferably purified by affinity chromatography. The use of column chromatography with an affinity matrix comprising TNF-α is preferred. Alternatively, an affinity purification tag can be added to either the N- or the C-terminus of the TNFR protein. For example, a polyhistidine-tag (His-tag), which is an amino acid motif with at least six histidines, can be used for this purpose (Hengen, P., 1995, Trends Biochem. Sci. 20:285-86). The addition of a His-tag can be achieved by the in-frame addition of a nucleotide sequence encoding the His-tag directly to either the 5' or 3' end of the TNFR open reading frame in an expression vector. One such nucleotide sequence for the addition of a C-terminal His-tag is given in SEQ ID No: 126. When a His-tag is incorporated into the protein, a nickel or cobalt affinity column is employed to purify the tagged TNFR, and the His-tag can optionally then be cleaved. Other suitable affinity purification tags and methods of purification of proteins with those tags are well known in the art.

Alternatively, a non-affinity based purification scheme can be used, involving fractionation of the TNFR extracts on a series of columns that separate the protein based on size (size exclusion chromatography), charge (anion and cation exchange chromatography) and hydrophobicity (reverse phase chromatography). High performance liquid chromatography can be used to facilitate these steps.

Other methods for the expression and purification of TNFR proteins are well known (See, e.g., U.S. Pat. No. 5,605,690 to Jacobs).

Use of Proteins for the Treatment of Inflammatory Diseases:

For therapeutic use, purified TNFR proteins of the present invention are administered to a patient, preferably a human, for treating TNF-dependent inflammatory diseases, such as arthritis. In the treatment of humans, the use of huTNFRs is preferred. The TNFR proteins of the present invention can be administered by bolus injection, continuous infusion, sustained release from implants, or other suitable techniques. Typically, TNFR therapeutic proteins will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the TNFR with buffers, antioxidants such as ascorbic acid, polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions, for example, sucrose, as diluents. Preservatives, such as benzyl alcohol may also be added. The amount and frequency of administration will depend of course, on such factors as the nature and the severity of the indication being treated, the desired response, the condition of the patient and so forth.

TNFR proteins of the present invention are administered systemically in therapeutically effective amounts preferably ranging from about 0.1 mg/kg/week to about 100 mg/kg/week. In preferred embodiments, TNFR is administered in amounts ranging from about 0.5 mg/kg/week to about 50 mg/kg/week. For local administration, dosages preferably range from about 0.01 mg/kg to about 1.0 mg/kg per injection.

Use of Expression Vectors to Increase the Levels of a TNF Antagonist in a Mammal:

The present invention provides a process of increasing the levels of a TNF antagonist in a mammal. The process includes the step of transforming cells of the mammal with an expression vector described herein, which drives expression of a TNFR as described herein.

The process is particularly useful in large mammals such as domestic pets, those used for food production, and primates. Exemplary large mammals are dogs, cats, horses cows, sheep, deer, and pigs. Exemplary primates are monkeys, apes, and humans.

The mammalian cells can be transformed either in vivo or ex vivo. When transformed in vivo, the expression vector are administered directly to the mammal, such as by injection. Means for transforming cells in vivo are well known in the art. When transformed ex vivo, cells are removed from the mammal, transformed ex vivo, and the transformed cells are reimplanted into the mammal.

Splice-switching Oligomers (SSOs):

In another aspect, the present invention employs splice switching oligonucleotides or splice switching oligomers (SSOs) to control the alternative splicing of TNFR2 so that the amount of a soluble, ligand-binding form that lacks exon 7 is increased and the amount of the integral membrane form is decreased. The methods and compositions of the present invention can be used in the treatment of diseases associated with excessive TNF activity.

Accordingly, one embodiment of the invention is a method of treating an inflammatory disease or condition by administering SSOs to a patient. The SSOs that are administered alter the splicing of a pre-mRNA to produce a mammalian TNFR2 protein that lacks exon 7. In another embodiment, the invention is a method of producing a mammalian TNFR2 protein that lacks exon 7 in a cell by administering SSOs to the cell.

The length of the SSO (i.e. the number of monomers in the oligomer) is similar to an antisense oligonucleotide (ASON), typically between about 8 and 30 nucleotides. In preferred embodiments, the SSO will be between about 10 to 16 nucleotides. The invention can be practiced with SSOs of several chemistries that hybridize to RNA, but that do not activate the destruction of the RNA by RNase H, as do conventional antisense 2'-deoxy oligonucleotides. The invention can be practiced using 2'O modified nucleic acid oligomers, such as where the 2'O is replaced with —O—$CH_3$, —O—$CH_2$—$CH_2$—O—$CH_3$, —O—$CH_2$—$CH_2$—$CH_2$—$NH_2$, —O—$CH_2$—$CH_2$—$CH_2$—OH or —F, where 2'O-methyl or 2'O-methyloxyethyl is preferred. The nucleobases do not need to be linked to sugars; so-called peptide nucleic acid oligomers or morpholine-based oligomers can be used. A comparison of these different linking chemistries is found in Sazani, P. et al., 2001, Nucleic Acids Res. 29:3695. The term splice-switching oligonucleotide is intended to cover the above forms. Those skilled in the art will appreciate the relationship between antisense oligonucleotide gapmers and SSOs. Gapmers are ASON that contain an RNase H activating region (typically a 2'-deoxyribonucleoside phosphorothioate) which is flanked by non-activating nuclease resistant oligomers. In general, any chemistry suitable for the flanking sequences in a gapmer ASON can be used in an SSO.

The SSOs of this invention may be made through the well-known technique of solid phase synthesis. Any other means for such synthesis known in the art may additionally or alternatively be used. It is well known to use similar techniques to prepare oligonucleotides such as the phosphorothioates and alkylated derivatives.

The bases of the SSO may be the conventional cytosine, guanine, adenine and uracil or thymidine. Alternatively, modified bases can be used. Of particular interest are modified bases that increase binding affinity. One non-limiting example of preferred modified bases are the so-called G-clamp or 9-(aminoethoxy)phenoxazine nucleotides, cytosine analogues that form 4 hydrogen bonds with guanosine. (Flanagan, W. M., et al., 1999, Proc. Natl. Acad. Sci. 96:3513; Holmes, S. C., 2003, Nucleic Acids Res. 31:2759). Specific examples of other bases include, but are not limited to, 5-methylcytosine ($^{Me}C$), isocytosine, pseudoisocytosine, 5-bromouracil, 5-propynyluracil, 5-propyny-6,5-methylthiazoleuracil, 6-aminopurine, 2-aminopurine, inosine, 2,6-di-aminopurine, 7-propyne-7-deazaadenine, 7-propyne-7-deazaguanine and 2-chloro-6-aminopurine.

A particularly preferred chemistry is provided by locked nucleic acids (LNA) (Koshkin, A. A., et al., 1998, Tetrahedron 54:3607; Obika, S., et al., 1998, Tetrahedron Lett. 39:5401). As used herein, the terms "LNA unit", "LNA monomer", "LNA residue", "locked nucleic acid unit", "locked nucleic acid monomer" or "locked nucleic acid residue", refer to a bicyclic nucleoside analogue. LNA units and methods of their synthesis are described in inter alia WO 99/14226, WO 00/56746, WO 00/56748, WO 01/25248, WO 02/28875, WO 03/006475 and WO 03/095467. The LNA unit may also be defined with respect to its chemical formula. Thus, an "LNA unit", as used herein, has the chemical structure shown in Formula 1 below:

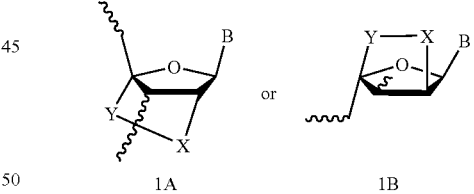

Formula 1

1A    1B wherein,

X is selected from the group consisting of O, S and NRH, where R is H or $C_1$-$C_4$-alkyl;

Y is (—$CH_2$)$_r$, where r is an integer of 1-4; and

B is a base of natural or non-natural origin as described above.

In a preferred embodiment, r is 1 or 2, and in a more preferred embodiment r is 1.

When LNA nucleotides are employed in an SSO it is preferred that non-LNA nucleotides also be present. LNA nucleotides have such high affinities of hybridization that there can be significant non-specific binding, which may reduce the effective concentration of the free-SSO. When LNA nucleotides are used they may be alternated conveniently with 2'-deoxynucleotides. The pattern of alternation is not critical.

Alternating nucleotides, alternating dinucleotides or mixed patterns, e.g., LDLDLD or LLDLLD or LDDLDD can be used. For example in one embodiment, contains a sequence of nucleotides selected from the group consisting of: LdLddLL-ddLdLdLL, LdLdLLLddLLLdLL, LMLMMLLMMLM-LMLL, LMLMLLLMMLLLMLL, LFLFFLLFFLFLFLL, LFLFLLLFFLLLFLL, LddLddLddL, dLddLddLdd, ddLd-dLddLd, LMMLMMLMML, MLMMLMMLMM, MMLM-MLMMLM, LFFLFFLFFL, FLFFLFFLFF, FFLFFLFFLF, dLdLdLdLdL, LdLdLdLdL, MLMLMLMLML, LMLM-LMLML, FLFLFLFLFL, LFLFLFLFL, where L is a LNA unit, d is a DNA unit, M is 2'MOE, F is 2'Fluoro.

When 2'-deoxynucleotides or 2'-deoxynucleoside phosphorothioates are mixed with LNA nucleotides it is important to avoid RNase H activation. It is expected that between about one third and two thirds of the LNA nucleotides of an SSO will be suitable. When affinity-enhancing modifications are used, including but not limited to LNA or G-clamp nucleotides, the skilled person recognizes it can be necessary to increase the proportion of such affinity-enhancing modifications.

Numerous alternative chemistries which do not activate RNase H are available. For example, suitable SSOs can be oligonucleotides wherein at least one of the internucleotide bridging phosphate residues is a modified phosphate, such as methyl phosphonate, methyl phosphonothioate, phosphoromorpholidate, phosphoropiperazidate, and phosphoroamidate. For example, every other one of the internucleotide bridging phosphate residues may be modified as described. In another non-limiting example, such SSO are oligonucleotides wherein at least one of the nucleotides contains a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described. (See references in U.S. Pat. No. 5,976,879 col. 4). For in vivo use, phosphorothioate linkages are preferred.

The length of the SSO will be from about 8 to about 30 bases in length. Those skilled in the art appreciate that when affinity-increasing chemical modifications are used, the SSO can be shorter and still retain specificity. Those skilled in the art will further appreciate that an upper limit on the size of the SSO is imposed by the need to maintain specific recognition of the target sequence, and to avoid secondary-structure forming self hybridization of the SSO and by the limitations of gaining cell entry. These limitations imply that an SSO of increasing length (above and beyond a certain length which will depend on the affinity of the SSO) will be more frequently found to be less specific, inactive or poorly active.

SSOs of the invention include, but are not limited to, modifications of the SSO involving chemically linking to the SSO one or more moieties or conjugates which enhance the activity, cellular distribution or cellular uptake of the SSO. Such moieties include, but are not limited to, lipid moieties such as a cholesterol moiety, cholic acid, a thioether, e.g. hexyl-S-tritylthiol, a thiocholesterol, an aliphatic chain, e.g., dodecandiol or undecyl residues, a phospholipids, e.g., di-hexadecyl-rac-glycerol or triethylammonium 1,2-di-O-hexadecyl-rac-glycero-3-H-phosphonate, a polyamine or a polyethylene glycol chain, an adamantane acetic acid, a palmityl moiety, an octadecylamine or hexylamino-carbonyl-oxycholesterol moiety.

It is not necessary for all positions in a given SSO to be uniformly modified, and in fact more than one of the aforementioned modifications may be incorporated in a single compound or even at a single nucleoside within an SSO.

The SSOs may be admixed, encapsulated, conjugated, or otherwise associated with other molecules, molecule structures, or mixtures of compounds, as for example liposomes, receptor targeted molecules, oral, rectal, topical or other formulation, for assisting in uptake, distribution, and/or absorption.

Those skilled in the art appreciate that cellular differentiation includes, but is not limited to, differentiation of the spliceosome. Accordingly, the activity of any particular SSO can depend upon the cell type into which they are introduced. For example, SSOs which are effective in one cell type may be ineffective in another cell type.

The methods, oligonucleotides, and formulations of the present invention are also useful as in vitro or in vivo tools to examine splicing in human or animal genes. Such methods can be carried out by the procedures described herein, or modifications thereof which will be apparent to skilled persons.

The SSOs disclosed herein can be used to treat any condition in which the medical practitioner intends to limit the effect of TNF or the signalling pathway activated by TNF. In particular, the invention can be used to treat an inflammatory disease. In one embodiment, the condition is an inflammatory systemic disease, e.g., rheumatoid arthritis or psoriatic arthritis. In another embodiment, the disease is an inflammatory liver disease. Examples of inflammatory liver diseases include, but are not limited to, hepatitis associated with the hepatitis A, B, or C viruses, alcoholic liver disease, and non-alcoholic steatosis. In yet another embodiment, the inflammatory disease is a skin condition such as psoriasis.

The uses of the present invention include, but are not limited to, treatment of diseases for which known TNF antagonists have been shown useful. Three specific TNF antagonists are currently FDA-approved. The drugs are etanercept (Enbrel®), infliximab (Remicade®) and adalimumab (Humira®). One or more of these drugs is approved for the treatment of rheumatoid arthritis, juvenile rheumatoid arthritis, psoriasis, psoriatic arthritis, ankylosing spondylitis, and inflammatory bowel disease (Crohn's disease or ulcerative colitis).

The administration of the SSO to subjects can be accomplished using procedures developed for ASON. ASON have been successfully administered to experimental animals and human subjects by intravenous administration in saline in doses as high as 6 mg/kg three times a week (Yacysyhn, B. R., et al., 2002, Gut 51:30 (anti-ICAM-1 ASON for treatment of Crohn's disease); Stevenson, J., et al., 1999, J. Clinical Oncology 17:2227 (anti-RAF-1 ASON targeted to PBMC)). The pharmacokinetics of 2'O-MOE phosphorothioate ASON, directed towards TNF-α has been reported (Geary, R. S., et al., 2003, Drug Metabolism and Disposition 31:1419). The systemic efficacy of mixed LNA/DNA molecules has also been reported (Fluiter, K., et al., 2003, Nucleic Acids Res. 31:953).

The systemic activity of SSO in a mouse model system was investigated using 2'O-MOE phosphorothioates and PNA chemistries. Significant activity was observed in all tissues investigated except brain, stomach and dermis (Sazani, P., et al., 2002, Nature Biotechnology 20, 1228).

In general any method of administration that is useful in conventional antisense treatments can be used to administer the SSO of the invention. For testing of the SSO in cultured cells, any of the techniques that have been developed to test ASON or SSO may be used.

Formulations of the present invention comprise SSOs in a physiologically or pharmaceutically acceptable carrier, such as an aqueous carrier. Thus formulations for use in the present invention include, but are not limited to, those suitable for parenteral administration including intraperitoneal, intraarticular, intravenous, intraarterial, subcutaneous, or intramuscular injection or infusion, as well as those suitable for topical, ophthalmic, vaginal, oral, rectal or pulmonary (including inhalation or insufflation of powders or aerosols, including by nebulizer, intratracheal, intranasal delivery) administration. The formulations may conveniently be presented in unit dosage form and may be prepared by any of the methods well known in the art. The most suitable route of administration in any given case may depend upon the subject, the nature and severity of the condition being treated, and the particular active compound which is being used.

Pharmaceutical compositions of the present invention include, but are not limited to, physiologically and pharmaceutically acceptable salts ,i.e, salts that retain the desired biological activity of the parent compound and do not impart undesired toxicological properties. Examples of such salts are (a) salts formed with cations such as sodium, potassium, $NH_4^+$, magnesium, calcium, polyamines such as spermine and spermidine, etc.; (b) acid addition salts formed with inorganic acids, for example, hydrochloric acid, hydrobromic acid, sulfuric acid, phosphoric acid, nitric acid and the like; and (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, napthalenesulfonic acid, methanesulfonic acid, p-toluenesulfonic acid, napthalenedisulfonic acid, polygalacturonic acid, and the like.

The present invention provides for the use of SSOs having the characteristics set forth above for the preparation of a medicament for increasing the ratio of a mammalian TNFR2 protein that lacks exon 7 to its corresponding membrane bound form, in a patient afflicted with an inflammatory disorder involving TNF-α, as discussed above. In the manufacture of a medicament according to the invention, the SSOs are typically admixed with, inter alia, an acceptable carrier. The carrier must, of course, be acceptable in the sense of being compatible with any other ingredients in the formulation and must not be deleterious to the patient. The carrier may be a solid or liquid. SSOs are incorporated in the formulations of the invention, which may be prepared by any of the well known techniques of pharmacy consisting essentially of admixing the components, optionally including one or more accessory therapeutic ingredients.

Formulations of the present invention may comprise sterile aqueous and non-aqueous injection solutions of the active compounds, which preparations are preferably isotonic with the blood of the intended recipient and essentially pyrogen free. These preparations may contain anti-oxidants, buffers, bacteriostats, and solutes which render the formulation isotonic with the blood of the intended recipient. Aqueous and non-aqueous sterile suspensions can include, but are not limited to, suspending agents and thickening agents. The formulations may be presented in unit dose or multi-dose containers, for example, sealed ampoules and vials, and may be stored in freeze-dried (lyophilized) condition requiring only the addition of the sterile liquid carrier, for example, saline or water-for-injection immediately prior to use.

In the formulation the SSOs may be contained within a particle or vesicle, such as a liposome, or microcrystal, which may be suitable for parenteral administration. The particles may be of any suitable structure, such as unilamellar or plurilameller, so long as the SSOs are contained therein. Positively charged lipids such as N-[1-(2,3-dioleoyloxy)propyl]-N,N,N-trimethyl-ammoniummethylsulfate, or "DOTAP," are particularly preferred for such particles and vesicles. The preparation of such lipid particles is well known. [See references in U.S. Pat. No. 5,976,879 col. 6]

The SSO can be targeted to any element or combination of elements that regulate splicing, including the 3' splice site, the 5' splice site, the branch point, the polypyrimidine tract, exonic splicing ehanders, exonic splicing silencers, intronic splicing enhancers, and intronic splicing silencers.

Those skilled in the art can appreciate that the invention as directed toward human TNFR2 can be practiced using SSO having a sequence that is complementary to at least 8, to at least 9, to at least 10, to at least 11, to at least 12, to at least 13, to at least 14, to at least 15, preferably between 10 and 16 nucleotides of the portions of the TNFR2 gene comprising exons 7 and its adjacent introns. SEQ ID No: 13 contains the sequence of exon 7 of TNFR2 and 50 adjacent nucleotides of the flanking introns. For example, SSO targeted to human TNFR2 can have a sequence selected from the sequences listed in Table 1. When affinity-enhancing modifications are used, including but not limited to LNA or G-clamp nucleotides, the skilled person recognizes the length of the SSO can be correspondingly reduced. The pattern of alternation of LNA and conventional nucleotides is not important.

TABLE 1

SSOs Targeted to Human TNFR2

| SEQ ID. | Name | Sequence 5' to 3' |
|---|---|---|
| 14 | 3378 | CCA CAA TCA GTC CTA G |
| 15 | SK101 | A CAA TCA GTC CTA G |
| 16 | SK102 | AA TCA GTC CTA G |
| 17 | SK103 | TCA GTC CTA G |
| 18 | SK104 | CCA CAA TCA GTC CT |
| 19 | SK105 | CCA CAA TCA GTC |
| 20 | SK106 | CCA CAA TCA G |
| 21 | SK107 | CA CAA TCA GTC CTA |
| 22 | SK108 | CA CAA TCA GTC C |
| 23 | SK109 | A CAA TCA GTC CT |
| 24 | SK110 | CAA TCA GTC CTA |
| 25 | SK111 | CA CAA TCA GT |
| 26 | SK112 | A CAA TCA GTC |
| 27 | SK113 | CAA TCA GTC C |
| 28 | SK114 | AA TCA GTC CT |
| 29 | SK115 | A TCA GTC CTA |
| 30 | 3379 | CAG TCC TAG AAA GAA A |
| 31 | SK117 | G TCC TAG AAA GAA A |
| 32 | SK118 | CC TAG AAA GAA A |
| 33 | SK119 | TAG AAA GAA A |
| 34 | SK120 | CAG TCC TAG AAA GA |
| 35 | SK121 | CAG TCC TAG AAA |
| 36 | SK122 | CAG TCC TAG A |

TABLE 1-continued

SSOs Targeted to Human TNFR2

| SEQ ID. | Name | Sequence 5' to 3' |
|---|---|---|
| 37 | SK123 | AG TCC TAG AAA GAA |
| 38 | SK124 | AG TCC TAG AAA G |
| 39 | SK125 | G TCC TAG AAA GA |
| 40 | SK126 | TCC TAG AAA GAA |
| 41 | SK127 | AG TCC TAG AA |
| 42 | SK128 | G TCC TAG AAA |
| 43 | SK129 | TCC TAG AAA G |
| 44 | SK130 | CC TAG AAA GA |
| 45 | SK131 | C TAG AAA GAA |
| 46 | 3384 | ACT TTT CAC CTG GGT C |
| 47 | SK133 | T TTT CAC CTG GGT C |
| 48 | SK134 | TT CAC CTG GGT C |
| 49 | SK135 | CAC CTG GGT C |
| 50 | SK136 | ACT TTT CAC CTG GG |
| 51 | SK137 | ACT TTT CAC CTG |
| 52 | SK138 | ACT TTT CAC C |
| 53 | SK139 | CT TTT CAC CTG GGT |
| 54 | SK140 | CT TTT CAC CTG G |
| 55 | SK141 | T TTT CAC CTG GG |
| 56 | SK142 | TTT CAC CTG GGT |
| 57 | SK143 | CT TTT CAC CT |
| 58 | SK144 | T TTT CAC CTG |
| 59 | SK145 | TTT CAC CTG G |
| 60 | SK146 | TT CAC CTG GG |
| 61 | SK147 | T CAC CTG GGT |

Those skilled in the art will also recognize that the selection of SSO sequences must be made with care to avoid a self-complementary SSO, which may lead to the formation of partial "hairpin" duplex structures. In addition, high GC content should be avoided to minimize the possibility of non-specific base pairing. Furthermore, SSOs matching off-target genes, as revealed for example by BLAST, should also be avoided.

In some situations, it may be preferred to select an SSO sequence that can target a human and at least one other species. These SSOs can be used to test and to optimize the invention in said other species before being used in humans, thereby being useful for regulatory approval and drug development purposes. For example, SSOs with sequences selected from SEQ ID Nos: 14, 30, 46, 70 and 71 which target human TNFR2 are also 100% complementary to the corresponding Macaca Mullata sequences. As a result these sequences can be used to test treatments in monkeys, before being used in humans.

It will be appreciated by those skilled in the art that various omissions, additions and modifications may be made to the invention described above without departing from the scope of the invention, and all such modifications and changes are intended to fall within the scope of the invention, as defined by the appended claims. All sequence citations, references, patents, patent applications or other documents cited referred to herein are incorporated by reference.

EXAMPLE 1

Materials and Methods

Oligonucleotides. Table 3 lists chimeric locked nucleic acid (LNA) SSOs with alternating 2'deoxy- and 2'O-4'-(methylene)-bicyclic-ribonucleoside phosphorothioates and having sequences as described in U.S. application Ser. No. 11/595,485. These were synthesized by Santaris Pharma, Denmark. For each SSO, the 5'-terminal nucleoside was a 2'O-4'-methylene-ribonucleoside and the 3'-terminal nucleoside was a 2'deoxy-ribonucleoside. Table 4 shows the sequences of chimeric LNA SSOs with alternating 2'-O-methyl-ribonucleoside-phosphorothioates (2'-OMe) and 2'O-4'-(methylene)-bicyclic-ribonucleoside phosphorothioates. These were synthesized by Santaris Pharma, Denmark. The LNA is shown in capital letters and the 2'-OME is shown in lower case letters.

Cell culture and transfections. L929 cells were maintained in minimal essential media supplemented with 10% fetal bovine serum and antibiotic (37° C., 5% $CO_2$). For transfection, L929 cells were seeded in 24-well plates at $10^5$ cells per well and transfected 24 hrs later. Oligonucleotides were complexed, at the indicated concentrations, with 2 μL of Lipofectamine™ 2000 transfection reagent (Invitrogen) as per the manufacturer's directions. The nucleotide/lipid complexes were then applied to the cells and incubated for 24 hrs. The media was then aspirated and cells harvested with TRI-Reagent™ (MRC, Cincinnati, Ohio).

RT-PCR. Total RNA was isolated with TRI-Reagent (MRC, Cincinnati, Ohio) and TNFR1 or TNFR2 mRNA was amplified by GeneAmp® RT-PCR using rTth polymerase (Applied Biosystems) following supplier directions. Approximately 200 ng of RNA was used per reaction. Primers used in the examples described herein are included in Table 2. Cycles of PCR proceeded: 95° C., 60 sec; 56° C., 30 sec; 72° C., 60 sec for 22-30 cycles total.

In some instances a Cy5-labeled dCTP (GE Healthcare) was included in the PCR step for visualization (0.1 μL per 50 μL PCR reaction). The PCR products were separated on a 10% non-denaturing polyacrylamide gel, and Cy5-labeled bands were visualized with a Typhoon™ 9400 Scanner (GE Healthcare). Scans were quantified with ImageQuant™ (GE Healthcare) software. Alternatively, in the absence of the inclusion of Cy5-labeled dCTP, the PCR products were separated on a 1.5% agarose gel containing trace amounts of ethidium bromide for visualization.

PCR. PCR was performed with Platinum® Taq DNA Polymerase (Invitrogen) according to the manufacturer's directions. For each 50 μL reaction, approximately 30 pmol of both forward and reverse primers were used. Primers used in the examples described herein are included in Table 2. The thermocycling reaction proceeded, unless otherwise stated, as follows: 94° C., 3 minutes; then 30-40 cycles of 94° C., 30 sec; 55° C., 30 sec; and 72° C., 105 sec; followed by 72° C., 3 minutes. The PCR products were analyzed on 1.5% agarose gels and visualized with ethidium bromide.

TABLE 2

RT-PCR and PCR Primers

| SEQ ID. | Name | Sequence 5' to 3' |
|---|---|---|
| | | Human TNFR2 |
| 74 | TR001 | ACT GGG CTT CAT CCC AGC ATC |
| 75 | TR002 | CAC CAT GGC GCC CGT CGC CGT CTG G |
| 76 | TR003 | CGA CTT CGC TCT TCC ACT TGA GAA GCC CTT GTG CCT GCA G |
| 77 | TR004 | TTA ACT GGG CTT CAT CCC AGC ATC |
| 78 | TR005 | CTG CAG GCA CAA GGG CTT CTC AAC TGG AAG AGC GAA GTC G |
| 79 | TR026 | TTA ACT GGG CTT CAT CCC AGC |
| 80 | TR027 | CGA TAG AAT TCA TGG CGC CCG TCG CCG TCT GG |
| 81 | TR028 | CCT AAC TCG AGT TAA CTG GGC TTC ATC CCA GC |
| 82 | TR029 | GAC TGA GCG GCC GCC ACC ATG GCG CCC GTC GCC GTC TGG |
| 83 | TR030 | CTA AGC GCG CCC GCT TAA CTG GGC TTC ATC CCA GCA TC |
| 84 | TR047 | CCT TCT CCA ACA CGA CTT CA |
| 85 | TR048 | CTT ATC GGC AGG CAA GTG AGG |
| 86 | TR049 | ACT GAA ACA TCA GAC GTC GTG TCC |
| 87 | TR050 | CCT TAT CCC CAG GCA ACT GAG |
| | | Human TNFR1 |
| 88 | TR006 | CCT CAT CTC ACA AGA CTC CCC C |
| 89 | TR007 | GCC ACC ATG CCC CTC TCC ACC GTG C |
| 90 | TR008 | CCC CAC TGA GGA CTC AGT TTG TGG GAA ATC GAC ACC TG |
| 91 | TR009 | CAG GTC TCG ATT TCC CAC AAA CTG AGT CCT CAC TCC CC |
| 92 | TR010 | CAC CAT GGG CCT CTC ACC GT GC |
| 93 | TR011 | TCT GAG AAG ACT GGG CG |
| 94 | TR031 | CGA TAG GAT CCA TGG GCC TCT CCA CCG TGC |
| 95 | TR032 | CCT AAC TCG AGT CAT CTG AGA AGA CTG GGC G |
| 96 | TR033 | GAC TGA GCG GCC GCC ACC ATG GGC CTC TCC ACC GTG C |
| 97 | TR034 | CTA AGC GCG CCG CT CAT CTG AGA AGA CTG GGC G |
| | | Mouse TNFR2 |
| 98 | TR012 | GGT CAG GCC ACT TTG ACT GC |
| 99 | TR013 | CAC CGC TGC CCC TAT GGC G |
| 100 | TR014 | CAC CGC TGC CAC TAT GGC G |
| 101 | TR015 | GGT CAG GCC ACT TTG ACT GCA ATC |
| 102 | TR016 | GCC ACC ATG GCG CCC GCC GCC CTC TGG |
| 103 | TR017 | GGC ATC TCT CTT CCA ATT GAG AAG CCC TCC TGC CTA CAA AG |
| 104 | TR018 | CTT TGT AGG CAG GAG GGC TTC TCA ATT GGA AGA GAG ATG CC |
| 105 | TR019 | GGC CAC TTT GAC TGC AAT CTG |
| 106 | TR035 | CAC CAT GGC GCC CGC GCC CCT CTG G |
| 107 | TR036 | TCA GGC CAC TTT GAC TGC AAT C |
| 108 | TR037 | CGA TAG AAT TCA TGG CGC CCG CCG CCC TCT GG |
| 109 | TR038 | CCT AAC TCG AGT CAG GCC ACT TTG ACT GCA ATC |
| 110 | TR039 | GAC TGA GCG GCC GCC ACC ATG GCG CCC GCC GCC CTC TGG |
| 111 | TR040 | CTA AGC GCG CCG CT CAG GCC ACT TTG ACT GCA ATC |
| 112 | TR045 | GAG CCC AAA TGG AAA TGT GC |
| 113 | TR046 | GCT CAA GGC CTA CTG CAT CC |
| | | Mouse TNFR1 |
| 114 | TR020 | GGT TAT CGC GGG AGG CGG GTC G |
| 115 | TR021 | GCC ACC ATG GGT CTC CCC ACC GTG CC |
| 116 | TR022 | CAC AAA CCC CCA GGA CTC AGT TTG TAG GAA TCC CGT GCC T |
| 117 | TR023 | AGG CAC GGG ATC CCT ACA AAC TGA GTC CTG GGG GTT TGT G |
| 118 | TR024 | CAC CAT GGG TCT CCC CAC CGT GCC |
| 119 | TR025 | TCG CGG GAG GCG GGT CGT GG |
| 120 | TR041 | CGA TAG TCG ACA TGG GTC TCC CCA CCG TGC C |
| 121 | TR042 | CCT AAG AAT TCT TAT CGC GGG AGG CGG GTC G |
| 122 | TR043 | GAC TGA GCG GCC GCC ACC ATG GGT CTC CCC ACC GTG CC |
| 123 | TR044 | CTA AGC GCG CCG CT TAT CGC GGG AGG CGG GTC G |

Human hepatocyte cultures. Human hepatocytes were obtained in suspension either from ADMET technologies, or from The UNC Cellular Metabolism and Transport Core at UNC-Chapel Hill. Cells were washed and suspended in RPMI 1640 supplemented with 10% FBS, 1 μg/mL human insulin, and 13 nM Dexamethasone. Hepatocytes were plated in 6-well plates at $0.5 \times 10^6$ cells per plate in 3 mL media. After 1-1.5 hrs, non-adherent cells were removed, and the media was replaced with RPMI 1640 without FBS, supplemented with 1 μg/mL human insulin, and 130 nM Dexamethasone.

For delivery of SSOs to hepatocytes in 6-well plates, 10 μL of a 5 μM SSO stock was diluted into 100 μL of OPTI-MEM™, and 4 μL of Lipofectamine™ 2000 was diluted into 100 μL of OPTI-MEM™. The 200 μL complex solution was then applied to the cells in the 6-well plate containing 2800 μL of media, for a total of 3000 μL. The final SSO concentration was 17 nM. After 24 hrs, cells were harvested in TRI-Reagent™. Total RNA was isolated per the manufacturer's directions. Approximately 200 ng of total RNA was subjected to reverse transcription-PCR (RT-PCR).

ELISA. To determine the levels of soluble TNFR2 in cell culture media or sera, the Quantikine® Mouse sTNF RII ELISA kit from R&D Systems (Minneapolis, Minn.) or Quantikine® Human sTNF RII ELISA kit from R&D Systems (Minneapolis, Minn.) were used. The antibodies used for detection also detect the protease cleavage forms of the receptor. ELISA plates were read using a microplate reader set at 450 nm, with wavelength correction set at 570 nm.

For mouse in vivo studies, blood from the animals was clotted for 1 hour at 37° C. and centrifuged for 10 min at 14,000 rpm (Jouan BRA4i centrifuge) at 4° C. Sera was collected and assayed according to the manufacturer's guide, using 50 μL of mouse sera diluted 1:10.

L929 cytotoxicity assay. L929 cells plated in 96-well plates at $10^4$ cells per well were treated with 0.1 ng/mL TNF-α and 1 μg/mL actinomycin D in the presence of 10% serum from mice treated with the indicated oligonucleotide in 100 μL total of complete MEM media (containing 10% regular FBS) and allowed to grow for ~24 hrs at 37° C. Control lanes were plated in 10% serum from untreated mice. Cell viability was measured 24 hrs later by adding 20 μL CellTiter 96® AQ$_{ueous}$ One Solution Reagent (Promega) and measuring absorbance at 490 nm with a microplate reader. Cell viability was normalized to untreated cells.

Western blots. Twenty μL of media or 20 μg of lysate were loaded in each well of a 4-12% NuPAGE® polyacrylamide gel (Invitrogen). The gel was run 40 min at 200V. The protein was transferred, for 1 hr at 30V, to an Invitrolon™ PVDF membrane (Invitrogen), which was then blocked with StartingBlock® Blocking Buffer (Pierce) for 1 hr at room temperature. The membrane was incubated for 3 hrs at room temperature with a rabbit polyclonal antibody that recognizes the C-terminus of human and mouse TNFR2 (Abcam), Following three washes in PBS-T buffer (1× PBS, 0.1% Tween-20), the membrane was incubated for one hour at room temperature with secondary goat anti-rabbit antibody (Abcam) and again washed three times with PBS-T buffer. The protein was then detected with ECL Plus™ (GE Healthcare), according to the manufacturer's recommendations and then photographed.

EXAMPLE 2

SSO Splice Switching Activity with TNFR mRNA

Figure 1:
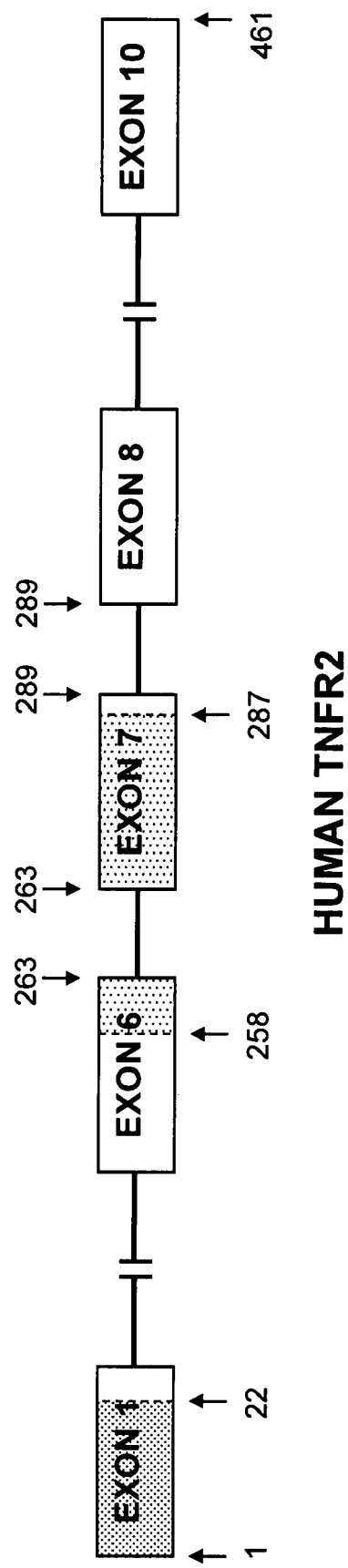
FIG. 1 schematically depicts the human TNFR2 structure. Relevant exons and introns are represented by boxes and lines, respectively. The signal sequence and the transmembrane region are shaded. Residues that form the boundaries of the signal sequence, the transmembrane region, and the final residue are indicated below the diagram. Exon boundaries are indicated above the diagram; if the 3' end of an exon and the 5' end of the following exon have the same residue number, then the splice junction is located within the codon encoding that residue.
Figures 2A, 2B:
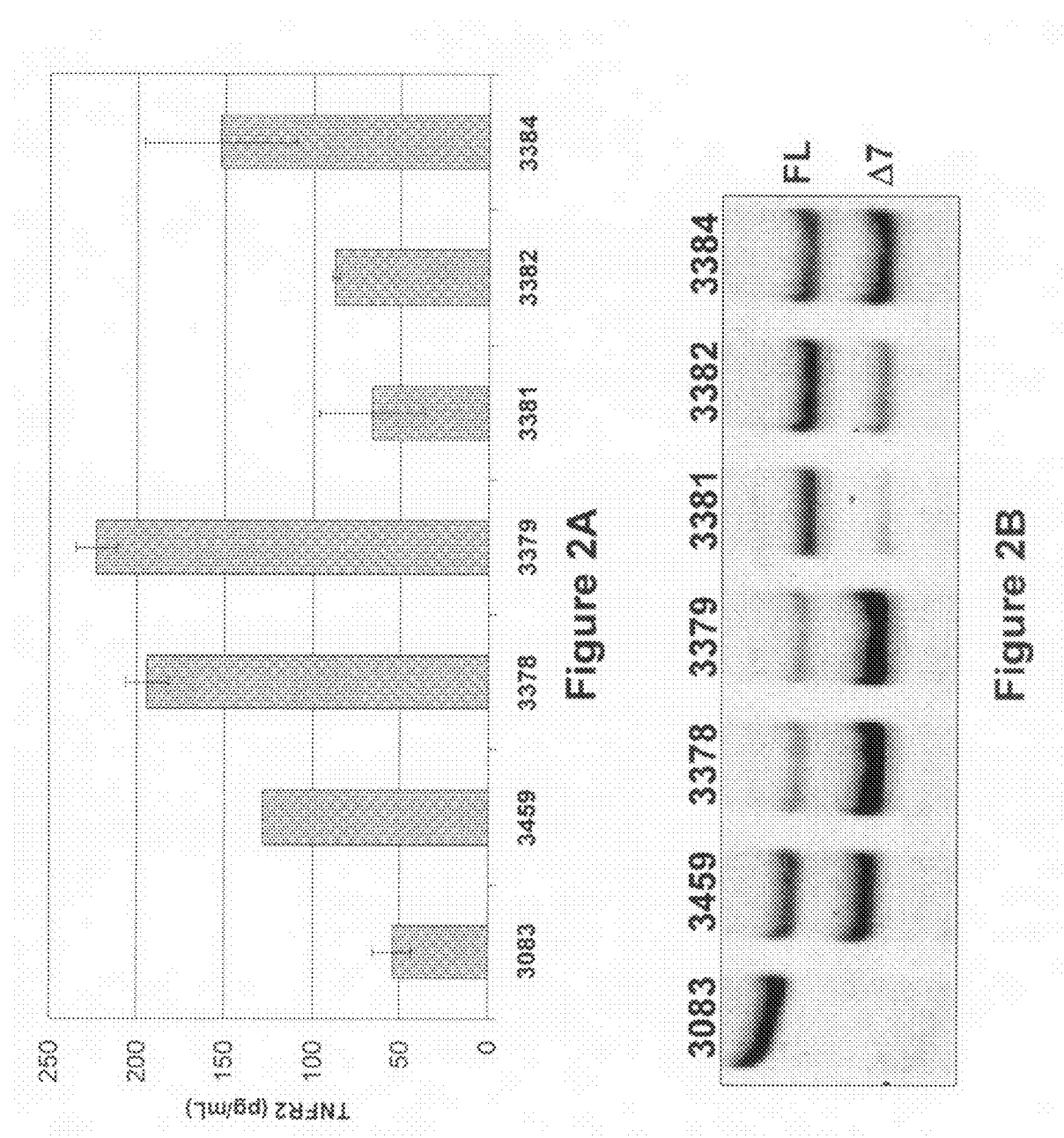
FIG. 2A graphically illustrates the amount of soluble TNFR2 from SSO treated primary human hepatocytes. The indicated SSO was transfected into primary human hepatocytes at 50 nM. After ~48 hrs, the extracellular media was analyzed by enzyme linked immunosorbant assay (ELISA) for soluble TNFR2 using the Quantikine® Human sTNF RII ELISA kit from R&D Systems (Minneapolis, Minn.). Error bars represent the standard deviation for 3 independent experiments.
FIG. 2B: Total RNA was analyzed for TNFR2 splice switching by RT-PCR using primers specific for human TNFR2. SSOs targeted to exon seven led to shifting from full length TNFR2 mRNA (FL) to TNFR2 Δ7 mRNA (Δ7). SSO 3083 is a control SSO with no TNFR2 splice switching ability.

Table 3 shows the splice switching activities of SSOs having sequences as described in U.S. application Ser. No. 11/595,485 and targeted to mouse and human TNFRs. Of SSOs targeted to mouse TNFR2 exon 7, at least 8 generated some muTNFR2 Δ7 mRNA. In particular, SSO 3312, 3274 and 3305 induced at least 50% skipping of exon 7; SSO 3305 treatment resulted in almost complete skipping. Of SSOs transfected into primary human hepatocytes, and targeted to human TNFR2 exon 7, at least 7 SSOs generated some huTNFR2 Δ7 mRNA. In particular, SSOs 3378, 3379, 3384 and 3459 induced at least 75% skipping of exon 7 (FIG. 2B), and significant induction of huTNFR2 Δ7 into the extracellular media (FIG. 2A).

TABLE 3

SSO Splice Switching Activity

| SEQ ID. | Name | Activity |
|---|---|---|
| | Mouse TNFR2 | |
| | 3272 | − |
| | 3304 | − |
| | 3305 | + |
| | 3306 | + |
| | 3307 | + |
| | 3308 | + |
| | 3309 | + |
| | 3310 | − |
| | 3311 | + |
| 62 | 3274 | + |
| | 3312 | + |
| | 3273 | − |
| | Mouse TNFR1 | |
| | 3333 | + |
| | Human TNFR2 | |
| 14 | 3378 | + |
| 30 | 3379 | + |
| | 3380 | − |
| 70 | 3381 | + |
| 71 | 3382 | + |
| | 3383 | − |
| 46 | 3384 | + |
| 72 | 3459 | + |
| | 3460 | − |
| 73 | 3461 | + |
| | Control | |
| | 3083 | − |

Table 4 contains the sequences of 10 nucleotide chimeric SSOs with alternating 2'-O-methyl-ribonucleoside-phosphorothioates (2'-OMe) and 2'O-4'-(methylene)-bicyclic-ribonucleoside phosphorothioates. These SSOs are targeted to exon 7 of mouse TNFR2.

TABLE 4

LNA/2'-OMe-ribonucleosidephosphorothioate chimeric mouse targeted SSO

| SEQ ID. | Name | Sequence 5' to 3'* |
|---|---|---|
| 62 | 3274 | AgAgCaGaAcCtTaCt |
| 63 | 3837 | gAaCcTuAcT |
| 64 | 3838 | aGaGcAgAaC |
| 65 | 3839 | gAgCaGaAcC |
| 66 | 3840 | aGcAgAaCcT |
| 67 | 3841 | gCaCaAcCuT |
| 68 | 3842 | cAgAaCcTuA |
| 69 | 3843 | aGaAcCuTaC |

*Capital letters are 2'O-4'-(methylene)-bicyclic-ribonucleosides; lowercase letters are 2'-OMe To analyze the in vitro splice-switching activity of the SSOs listed in Table 4, L929 cells were cultured and selected as described in Example 1. For delivery of each of the SSOs in Table 4 to the L929 cells, SSOs were diluted into 50 μL of OPTI-MEM™, and then 50 μL Lipofectamine™ 2000 mix (1 part Lipofectamine™ 2000 to 25 parts OPTI-MEM™) was added and incubated for 20 minutes. Then 400 μL of serum free media was added to the SSOs and applied to the cells in the 24-well plates. The final SSO concentration was either 50 or 100 nM. After 24 hrs, cells were harvested in 800 μL TRI-Reagent™. Total RNA was isolated per the manufacturer's directions and analyzed by RT-PCR (FIG. 3) using the forward primer TR045 (SEQ ID No: 112) and the reverse primer TR046 (SEQ ID No: 113).

To analyze the in vivo splice-switching activity of the SSOs listed in Table 4, mice were injected with the SSOs listed in Table 4 intraperitoneal (i.p.) at 25 mg/kg/day for 5 days. Mice were bled before injection and again 1, 5 and 10 days after the last injection. The concentration of soluble TNFR2 Δ7 in the sera taken before the first injection and 10 days after the last injection were measured by ELISA (FIG. 4B). The mice were sacrificed on day 10 and total RNA from 5-10 mg of the liver was analyzed by RT-PCR (FIG. 4A) using the forward primer TR045 (SEQ ID No: 112) and the reverse primer TR046 (SEQ ID No: 113).

Figure 3:
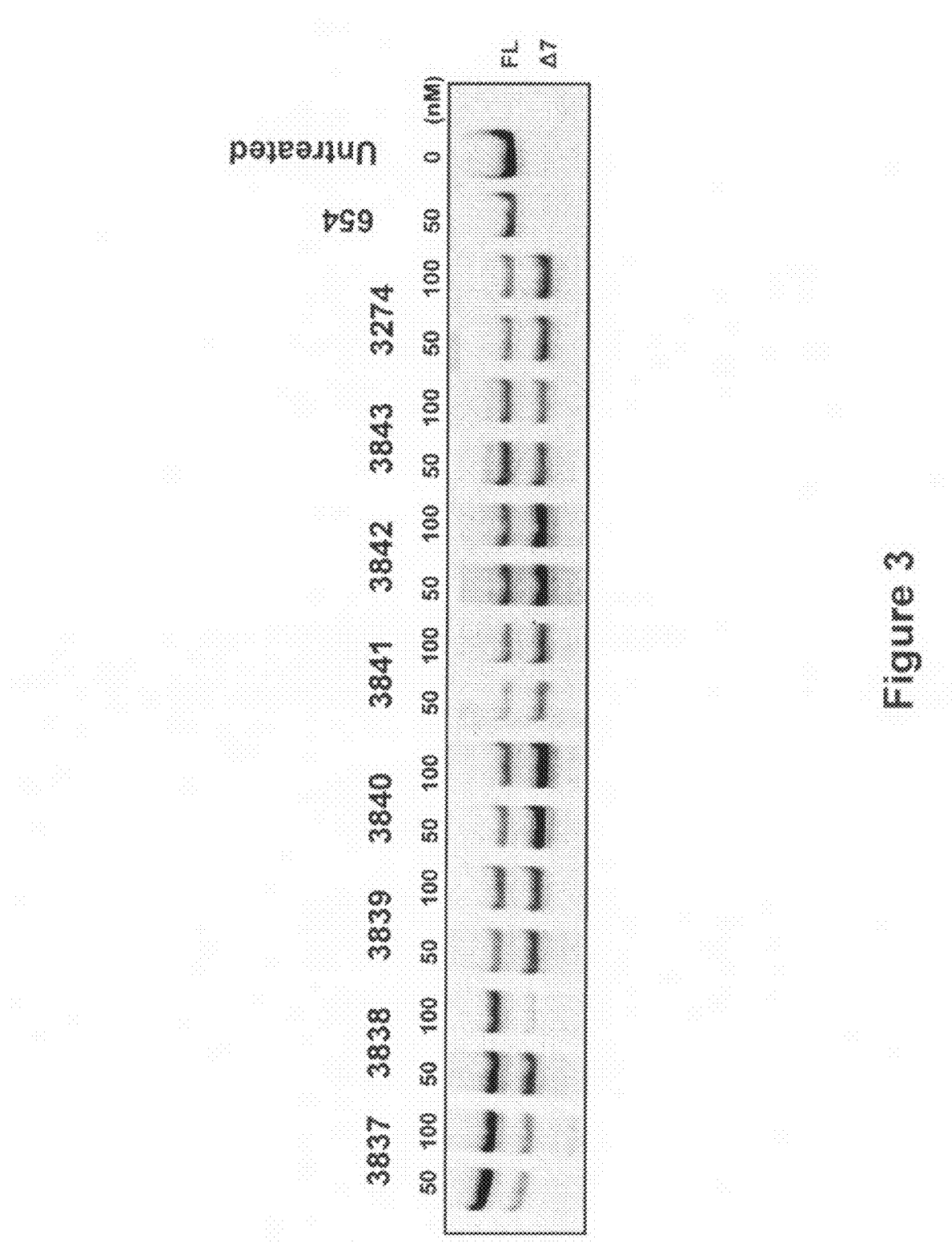
FIG. 3 shows the splicing products of L929 cells treated with SSO 10-mers targeted to mouse TNFR2 exon 7. L929 cells were transfected with the indicated SSO concentration (50 or 100 nM), and evaluated for splice switching of TNFR2 by RT-PCR 24 hrs later. PCR primers were used to amplify from Exon 5 to Exon 9, so that "Full Length" (FL) TNFR2 is represented by a 486 bp band. Transcripts lacking exon 7 (Δ7) is represented by a 408 bp band.

Of the 10 nucleotide SSOs subsequences of SSO 3274 tested in vitro, all of them generated at least some muTNFR2 Δ7 mRNA (FIG. 3). In particular, SSO 3839, 3840 and 3841 displayed greater splice-switching activity than the longer 16 nucleotide SSO 3274 from which they are derived. The three 10 nucleotide SSOs, 3839, 3840, 3841, that demonstrated the greatest activity in vitro also were able to generate significant amounts of muTNFR2 Δ7 mRNA (FIG. 4A) and soluble muTNFR2 Δ7 protein (FIG. 4B) in mice in vivo.

To assess the effect of SSO length on splice switching activity in human TNFR2, cells were treated with SSOs of different lengths. Primary human hepatocytes were transfected with the indicated SSOs selected from Table 1. These SSOs were synthesized by Santaris Pharma, Denmark with alternating 2'deoxy- and 2'O-4'-(methylene)-bicyclic-ribonucleoside phosphorothioates. For each SSO, the 5'-terminal nucleoside was a 2'O-4'-methylene-ribonucleoside and the 3'-terminal nucleoside was a 2'deoxy-ribonucleoside. These SSOs were either 10-, 12-, 14- or 16-mers. The concentration of soluble TNFR2 Δ7 was measured by ELISA (FIG. 5, top panel). Total RNA was analyzed by RT-PCR for splice switching activity (FIG. 5, bottom panel).

EXAMPLE 3

Analysis of the Splice Junction of SSO-induced TNFR2 Splice Variants

To confirm that the SSO splice switching, both in mice and in human cells, leads to the expected TNFR2 Δ7 mRNA, SSO-induced TNFR2 Δ7 mRNA was analyzed by RT-PCR and was sequenced.

Mice. Mice were injected with SSO 3274 intraperitoneal (i.p.) at 25 mg/kg/day for 10 days. The mice were then sacrificed and total RNA from the liver was analyzed by RT-PCR using the forward primer TR045 (SEQ ID No: 112) and the reverse primer TR046 (SEQ ID No: 113). The products were analyzed on a 1.5% agarose gel (FIG. 6A) and the product for the TNFR2 Δ7 was isolated using standard molecular biology techniques. The isolated TNFR2 Δ7 product was amplified by PCR using the same primers and then sequenced (FIG. 6B). The sequence data contained the sequence CTCTCTTC-CAATTGAGAAGCCCTCCTGC (nucleotides 777-804 of SEQ ID No: 11), which confirms that the SSO-induced TNFR2 Δ7 mRNA lacks exon 7 and that exon 6 is joined directly to exon 8.

Human hepatocytes. Primary human hepatocytes were transfected with SSO 3379 as described in Example 1. Total RNA was isolated 48 hrs after transfection. The RNA was converted to cDNA with the Superscript™ II Reverse Transcriptase (Invitrogen) using random hexamer primers according to the manufacturer's directions. PCR was performed on the cDNA using the forward primer TR049 (SEQ ID No: 86) and the reverse primer TR050 (SEQ ID No: 87). The products were analyzed on a 1.5% agarose gel (FIG. 7A). The band corresponding to TNFR2 Δ7 was isolated using standard molecular biology techniques and then sequenced (FIG. 7B). The sequence data contained the sequence CGCTCTTC-CAGTTGAGAAGCCCTTGTGC (nucleotides 774-801 of SEQ ID No: 9), which confirms that the SSO-induced TNFR2 Δ7 mRNA lacks exon 7 and that exon 6 is joined directly to exon 8.

EXAMPLE 4

SSO Dose-Dependent Production of TNFR2 Δ7 Protein in Primary Human Hepatocytes

The dose response of splice-switching activity of SSOs in primary human hepatocytes was tested. Human hepatocytes were obtained in suspension from ADMET technologies. Cells were washed three times and suspended in seeding media (RPMI 1640 supplemented with L-Glut, with 10% FBS, penicillin, streptomycin, and 12 nM Dexamethasone). Hepatocytes were evaluated for viability and plated in 24-well, collagen-coated plates at $1.0 \times 10^5$ cells per well. Typically, cell viability was 85-93%. After approximately 24 hrs, the media was replaced with maintenance media (seeding media without FBS).

For delivery of each of the SSOs to the hepatocytes, SSOs were diluted into 50 μL of OPTI-MEM™, and then 50 μL Lipofectamine™ 2000 mix (1 part Lipofectamine™ 2000 to 25 parts OPTI-MEM™) was added and incubated for 20 minutes. The SSOs were then applied to the cells in the 24-well plates. The final SSO concentration ranged from 1 to 150 nM. After 48 hrs, cells were harvested in 800 μL TRI-Reagent™.

Total RNA from the cells was analyzed by RT-PCR using the forward primer TR047 (SEQ ID No: 84) and the reverse primer TR048 (SEQ ID No: 85) (FIG. 8A). The concentration of soluble TNFR2 Δ7 in the serum was measured by ELISA (FIG. 8B). Both huTNFR2 Δ7 mRNA (FIG. 8A) and secreted huTNFR2 Δ7 protein (FIG. 8B) displayed dose dependent increases.

EXAMPLE 5

Secretion of TNFR2 Splice Variants from Murine Cells

The ability of SSOs to induce soluble TNFR2 protein production and secretion into the extracellular media was tested. L929 cells were treated with SSOs as described in Example 1, and extracellular media samples were collected ~48 hrs after transfection. The concentration of soluble TNFR2 in the samples was measured by ELISA (FIG. 9). SSOs that best induced shifts in RNA splicing, also secreted the most protein into the extracellular media. In particular, SSOs 3305, 3312, and 3274 increased soluble TNFR2 at least 3.5-fold over background. Consequently, induction of the splice variant mRNA correlated with production and secretion of the soluble TNFR2.

EXAMPLE 6

In Vivo Injection of SSOs Generated muTNFR2 Δ7 mRNA in Mice

SSO 3305 in saline was injected intraperitoneal (i.p.) daily for 4 days into mice at doses from 3 mg/kg to 25 mg/kg. The mice were sacrificed on day 5 and total RNA from the liver was analyzed by RT-PCR. The data show splice switching efficacy similar to that found in cell culture. At the maximum dose of 25 mg/kg, SSO 3305 treatment induced almost full conversion to Δ7 mRNA (FIG. 10, bottom panel).

A similar experiment with SSO 3274 induced about 20% conversion to Δ7 mRNA. To optimize SSO 3274 induction of Δ7 mRNA, both the dose regimen and the time from the last injection to the sacrifice of the animal were varied. SSO 3274 was injected (i.p.) into mice daily for 4 days. SSO treatment induced about 30% conversion to Δ7 mRNA in mice analyzed on day 15, whereas a 20% shift was observed in mice analyzed on day five (FIG. 10, top panel). Furthermore, mice given injections for 10 days, and sacrificed on day 11 showed a 50% induction of Δ7 mRNA (FIG. 10, top). These in vivo data suggest that TNFR2 SSOs can produce muTNFR2 Δ7 mRNA for at least 10 days after administration.

EXAMPLE 7

Circulatory TNFR2 Δ7

Mice were injected with SSO 3274, 3305, or the control 3083 intraperitoneal (i.p.) at 25 mg/kg/day for 10 days. Mice were bled before injection and again 1, 5 and 10 days after the last injection. The concentration of soluble TNFR2 Δ7 in the serum was measured. SSO treatment induced soluble TNFR2 Δ7 protein levels over background for at least 10 days (FIG. 11).

To test the effects at longer time points, the experiment was repeated, except that serum samples were collected until day 27 after the last injection. The results show only a slight decrease in soluble TNFR2 Δ7 levels 27 days after the last SSO injection (FIG. 12).

EXAMPLE 8

Anti-TNF-α Activity in Mice Serum

The anti-TNF-α activity of serum from SSO 3274 treated mice was tested in an L929 cytotoxicity assay. In this assay, serum is assessed for its ability to protect cultured L929 cells from the cytotoxic effects of a fixed concentration of TNF-α as described in Example 1. Serum from mice treated with SSO 3274 but not control SSOs (3083 or 3272) increased viability of the L929 cells exposed to 0.1 ng/mL TNF-α (FIG. 13). Hence, the SSO 3274 serum contained TNF-α antagonist sufficient to bind and to inactivate TNF-α, and thereby protect the cells from the cytotoxic effects of TNF-α. This anti-TNF-α activity was present in the serum of animals 5 and 27 days after the last injection of SSO 3274.

EXAMPLE 9

Comparison of SSO Generated TNFR2 Δ7 to Other Anti-TNF-α Antagonists

L929 cells were seeded as in Example 8. Samples were prepared containing 90 μL of serum-free MEM, 0.1 ng/ml TNF-α and 1 μg/ml of actinomycin D, with either (i) recombinant soluble protein (0.01-3 μg/mL)) from Sigma® having the 236 amino acid residue extracellular domain of mouse TNFR2, (ii) serum from SSO 3274 or SSO 3305 treated mice (1.25-10%, diluted in serum from untreated mice; the concentration of TNFR2 Δ7 was determined by ELISA) or (iii) Enbrel® (0.45-150 pg/ml) to a final volume of 100 μl with a final mouse serum concentration of 10%. The samples were incubated at room temperature for 30 minutes. Subsequently, the samples were applied to the plated cells and incubated for ~24 hrs at 37° C. in a 5% $CO_2$ humidified atmosphere. Cell viability was measured by adding 20 μL CellTiter 96® $AQ_{ueous}$ One Solution Reagent (Promega) and measuring absorbance at 490 nm with a microplate reader. Cell viability was normalized to untreated cells and plotted as a function of TNF antagonist concentration (FIG. 14).

EXAMPLE 10

Stability of TNFR2 Δ7 mRNA and Protein

Mice were treated with either SSO 3274 or 3272 (control) (n=5) by i.p. injection at a dose of 25 mg/kg/day daily for five days. Mice were bled before injection and again 5, 15, 22, 27, and 35 days after the last injection. The concentration of soluble TNFR2 Δ7 in the serum was measured (FIG. 15A). Splice shifting of TNFR2 in the liver was also determined at the time of sacrifice by RT-PCR of total RNA from the liver (FIG. 15B). Combined with data from Example 7, a time course of TNFR2 mRNA levels after SSO treatment was constructed, and compared with the time course of TNFR2 Δ7 protein in serum (FIG. 16). The data show that TNFR2 Δ7 mRNA in vivo decays at a rate approximately 4 times faster than that of TNFR2 Δ7 protein in serum. On day 35, TNFR2 Δ7 mRNA was only detectable in trace amounts, whereas TNFR2 Δ7 protein had only decreased by 20% from its peak concentration.

EXAMPLE 11

Generation of Human TNFR2 Δ7 cDNA

A plasmid containing the full length human TNFR2 cDNA was obtained commercially from OriGene (Cat. No: TC119459, NM_001066.2). The cDNA was obtained by performing PCR on the plasmid using reverse primer TR001 (SEQ ID No: 74) and forward primer TR002 (SEQ ID No: 75). The PCR product was isolated and was purified using standard molecular biology techniques, and contains the 1383 bp TNFR2 open reading frame without a stop codon.

Alternatively, full length human TNFR2 cDNA is obtained by performing RT-PCR on total RNA from human mononuclear cells using the TR001 reverse primer and the TR002 forward primer. The PCR product is isolated and is purified using standard molecular biology techniques.

To generate human TNFR2 Δ7 cDNA, two separate PCR reactions were performed on the full length human TNFR2 cDNA, thereby creating overlapping segments of the TNFR2 Δ7 cDNA. In one reaction, PCR was performed on full length TNFR2 cDNA using the forward primer TR003 (SEQ ID No: 76) and the reverse primer TR004 (SEQ ID No: 77). In the other reaction, PCR was performed on full length TNFR2 cDNA using the reverse primer TR005 (SEQ ID No: 78) and the TR002 forward primer. Finally, the 2 overlapping segments were combined, and PCR was performed using the TR002 forward primer and the TR004 reverse primer. The PCR product was isolated and was purified using standard molecular biology techniques, and was expected to contain the 1308 bp TNFR2 Δ7 open reading frame with a stop codon (SEQ ID No: 9).

Similarly, by using the TR001 reverse primer instead of the TR004 reverse primer in these PCR reactions the 1305 bp human TNFR2 Δ7 open reading frame without a stop codon was generated. This allows for the addition of in-frame C-terminal affinity purification tags, such as His-tag, when the final PCR product is inserted into an appropriate vector.

EXAMPLE 12

Generation of Human TNFR1 Δ7 cDNA

A plasmid containing the full length human TNFR2 cDNA is obtained commercially from OriGene (Cat. No: TC127913, NM_001065.2). The cDNA is obtained by performing PCR on the plasmid using the TR006 reverse primer (SEQ ID No: 88) and the TR007 forward primer (SEQ ID No: 89). The full length human TNFR1 cDNA PCR product is isolated and is purified using standard molecular biology techniques.

Alternatively, full length human TNFR1 cDNA is obtained by performing RT-PCR on total RNA from human mononuclear cells using the TR0006 reverse primer and the TR007 forward primer. The full length human TNFR1 cDNA PCR product is isolated and is purified using standard molecular biology techniques.

To generate human TNFR1 Δ7 cDNA, two separate PCR reactions are performed on the full length human TNFR1 cDNA, thereby creating overlapping segments of the TNFR1 Δ7 cDNA. In one reaction, PCR is performed on full length TNFR1 cDNA using the TR008 forward primer (SEQ ID No: 90) and the TR006 reverse primer. In the other reaction, PCR is performed on full length TNFR1 cDNA using the TR009 reverse primer (SEQ ID No: 91) and the TR010 forward primer (SEQ ID No: 92). Finally, the 2 overlapping segments are combined, and PCR is performed using the TR010 forward primer and the TR006 reverse primer. The PCR product is isolated and is purified using standard molecular biology techniques, and contains the 1254 bp human TNFR1 Δ7 open reading frame with a stop codon (SEQ ID No: 5).

Alternatively, by using the TR011 reverse primer (SEQ ID No: 93) instead of the TR006 reverse primer in these PCR reactions the 1251 bp human TNFR1 Δ7 open reading frame without a stop codon is generated. This allows for the addition of in-frame C-terminal affinity purification tags, such as His-tag, when the final PCR product is inserted into an appropriate vector.

EXAMPLE 13

Generation of Murine TNFR2 Δ7 cDNA

To generate full length murine TNFR2 cDNA, PCR was performed on the commercially available FirstChoice™ PCR-Ready Mouse Liver cDNA (Ambion, Cat. No: AM3300) using the TR012 reverse primer (SEQ ID No: 98) and the TR013 forward primer (SEQ ID No: 99). The full length murine TNFR2 cDNA PCR product is isolated and is purified using standard molecular biology techniques. Then by performing PCR on the resulting product using the TR014 forward primer (SEQ ID No: 100) and the TR012 reverse primer the proper Kozak sequence was introduced.

Alternatively, full length murine TNFR2 cDNA is obtained by performing RT-PCR on total RNA from mouse mononuclear cells or mouse hepatocytes using the TR015 reverse primer (SEQ ID No: 101) and the TR016 forward primer (SEQ ID No: 102). The full length murine TNFR2 cDNA PCR product is isolated and is purified using standard molecular biology techniques.

To generate murine TNFR2 Δ7 cDNA, two separate PCR reactions were performed on the full length murine TNFR2 cDNA, thereby creating overlapping segments of the TNFR2 Δ7 cDNA. In one reaction, PCR was performed on full length TNFR2 cDNA using the TR017 forward primer (SEQ ID No: 103) and the TR015 reverse primer. In the other reaction, PCR was performed on full length TNFR2 cDNA using the TR018 reverse primer (SEQ ID No: 104) and the TR016 forward primer. Finally, the 2 overlapping segments were combined, and PCR was performed using the TR016 forward primer and the TR015 reverse primer. The PCR product was isolated and was purified using standard molecular biology techniques, and was expected to contain the 1348 bp murine TNFR2 Δ7 open reading frame with a stop codon (SEQ ID No: 11).

Alternatively, by using the TR019 reverse primer (SEQ ID No: 105) instead of the TR015 reverse primer in these PCR reactions the 1345 bp murine TNFR2 Δ7 open reading frame without a stop codon was generated. This allows for the addition of in-frame C-terminal affinity purification tags, such as His-tag, when the final PCR product is inserted into an appropriate vector.

EXAMPLE 14

Generation of Murine TNFR1 Δ7 cDNA

To generate full length murine TNFR1 cDNA, PCR is performed on the commercially available FirstChoice™ PCR-Ready Mouse Liver cDNA (Ambion, Cat. No: AM3300) using the TR020 reverse primer (SEQ ID No: 114) and the TR021 forward primer (SEQ ID No: 115). The full length murine TNFR1 cDNA PCR product is isolated and is purified using standard molecular biology techniques.

Alternatively, full length murine TNFR1 cDNA is obtained by performing RT-PCR on total RNA from mouse mononuclear cells using the TR020 reverse primer and the TR021 forward primer. The full length murine TNFR1 cDNA PCR product is isolated and is purified using standard molecular biology techniques.

To generate murine TNFR1 Δ7 cDNA, two separate PCR reactions are performed on the full length human TNFR1 cDNA, thereby creating overlapping segments of the TNFR1 Δ7 cDNA. In one reaction, PCR is performed on full length TNFR1 cDNA using the TR022 forward primer (SEQ ID No: 116) and the TR020 reverse primer. In the other reaction, PCR is performed on full length TNFR1 cDNA using the TR023 reverse primer (SEQ ID No: 117) and the TR024 forward primer (SEQ ID No: 118). Finally, the 2 overlapping segments are combined, and PCR is performed using TR024 forward primer and the TR020 reverse primer. The 1259 bp PCR product is isolated and is purified using standard molecular biology techniques, and contains the 1251 bp murine TNFR1 Δ7 open reading frame with a stop codon (SEQ ID No: 7).

Alternatively, by using the TR025 reverse primer (SEQ ID No: 119) instead of the TR020 reverse primer in these PCR reactions the 1248 bp murine TNFR1 Δ7 open reading frame without a stop codon is generated. This allows for the addition of in-frame C-terminal affinity purification tags, such as His-tag, when the final PCR product is inserted into an appropriate vector.

EXAMPLE 15

Construction of Vectors for the Expression of Human TNFR2 Δ7 in Mammalian Cells

For expression of the human TNFR2 Δ7 protein in mammalian cells, a human TNFR2 Δ7 cDNA PCR product from Example 11 was incorporated into an appropriate mammalian expression vector. The TNFR2 Δ7 cDNA PCR product from Example 11, both with and without a stop codon, and the pcDNA™ 3.1D/V5-His TOPO® expression vector (Invitrogen) were blunt-end ligated and isolated according to the manufacturer's directions. Plasmids containing inserts encoding human TNFR2 Δ7 were transformed into One-Shot® Top10 competent cells (Invitrogen), according to the supplier's directions. Fifty μL of the transformation mix were plated on LB media with 100 μg/mL of ampicillin and incubated overnight at 37° C. Single colonies were used to inoculate 5 mL cultures of LB media with 100 μg/mL ampicillin and incubated overnight at 37° C. The cultures were then used to inoculate 200 mL of LB media with 100 μg/mL of ampicillin and grown overnight at 37° C. The plasmids were isolated using GenElute™ Plasmid Maxiprep kit (Sigma) according to manufacturer's directions. Purification efficiency ranged from 0.5 to 1.5 mg of plasmid per preparation.

Three human TNFR2 Δ7 clones (1319-1, 1138-5 and 1230-1) were generated and sequenced. Clone 1319-1 contains the human TNFR2 Δ7 open reading frame without a stop codon followed directly by an in-frame His-tag from the plasmid; while clones 1138-5 and 1230-1 contain the TNFR2 Δ7 open reading frame followed immediately by a stop codon. The sequence of the His-tag from the plasmid is given in SEQ ID No: 126. The sequences of the TNFR2 Δ7 open reading frames of clones 1230-1 and 1319-1 were identical to SEQ ID No: 9 with and without the stop codon, respectively. However relative to SEQ ID No: 9, the sequence (SEQ ID No: 125) of the TNFR2 Δ7 open reading frames of clone 1138-5 differed by a single nucleotide at position 1055 in exon 10, with an A in the former and a G in the later. This single nucleotide change causes the amino acid 352 to change from a glutamine to an arginine.

EXAMPLE 16

Expression of Human TNFR2 Δ7 in *E. coli*

For expression of the human TNFR2 Δ7 protein in bacteria, a human TNFR2 Δ7 cDNA from Example 11 is incorporated into an appropriate expression vector, such as a pET Directional TOPO® expression vector (Invitrogen). PCR is performed on the PCR fragment from Example 11 using forward (TR002) (SEQ ID No: 75) and reverse (TR026) (SEQ ID No: 79) primers to incorporate a homologous recombination site for the vector. The resulting PCR fragment is incubated with the pET101/D-TOPO® vector (Invitrogen) according to the manufacturer's directions, to create the human TNFR2 Δ7 bacterial expression vector. The resulting vector is transformed into the *E. coli* strain BL21(DE3). The human TNFR2 Δ7 is then expressed from the bacterial cells according to the manufacturer's instructions.

EXAMPLE 17

Expression of Human TNFR2 Δ7 in Insect Cells

For expression of the human TNFR2 Δ7 protein in insect cells, a human TNFR2 Δ7 cDNA from Example 11 is incorporated into a baculoviral vector. PCR is performed on a human TNFR2 Δ7 cDNA from Example 11 using forward (TR027) (SEQ ID No: 80) and reverse (TR028) (SEQ ID No: 81) primers. The resulting PCR product is digested with the restriction enzymes EcoRI and XhoI. The digested PCR product is ligated with a EcoRI and XhoI digested pENTR™ Vector (Invitrogen), such as any one of the pENTR™ 1A, pENTR™ 2B, pENTR™ 3C, pENTR™ 4, or pENTR™ 11 Vectors, to yield an entry vector. The product is then isolated, amplified, and purified using standard molecular biology techniques.

A baculoviral vector containing the human TNFR2 Δ7 cDNA is generated by homologous recombination of the entry vector with BaculoDirect™ Linear DNA (Invitrogen) using LR Clonase™ (Invitrogen) according to the manufacturer's directions. The reaction mixture is then used to infect Sf9 cells to generate recombinant baculovirus. After harvesting the recombinant baculovirus, expression of human TNFR2 Δ7 is confirmed. Amplification of the recombinant baculovirus yields a high-titer viral stock. The high-titer viral stock is used to infect Sf9 cells, thereby expressing human TNFR2 Δ7 protein.

EXAMPLE 18

Generation of Adeno-Associated Viral Vectors for the Expression of Human TNFR2 Δ7

For in vitro or in vivo delivery to mammalian cells of the human TNFR2 Δ7 gene for expression in those mammalian cells, a recombinant adeno-associated virus (rAAV) vector is generated using a three plasmid transfection system as described in Grieger, J., et al., 2006, Nature Protocols 1:1412. PCR is performed on a purified human TNFR2 Δ7 PCR product of Example 11, using forward (TR029) (SEQ ID No: 82) and reverse (TR030) (SEQ ID No: 83) primers to introduce unique flanking NotI restriction sites. The resulting PCR product is digested with the NotI restriction enzyme, and isolated by standard molecular biology techniques. The NotI-digested fragment is then ligated to NotI-digested pTR-UF2 (University of North Carolina (UNC) Vector Core Facility), to create a plasmid that contains the human TNFR2 Δ7 open reading frame, operably linked to the CMVie promoter, flanked by inverted terminal repeats. The resulting plasmid is then transfected with the plasmids pXX680 and pHelper (UNC Vector Core Facility) into HEK-293 cells, as described in Grieger, J., et al., to produce rAAV particles containing the human TNFR2 Δ7 gene where expression is driven by the strong constitutive CMVie promoter. The virus particles are harvested and purified, as described in Grieger, J., et al., to provide an rAAV stock suitable for transducing mammalian cells.

EXAMPLE 19

Expression of Human TNFR1 Δ7 in E. coli

For expression of the human TNFR1 Δ7 protein in bacteria, the cDNA from Example 12 is incorporated into an appropriate expression vector, such as a pET Directional TOPO® expression vector (Invitrogen). PCR is performed on the cDNA from Example 12 using forward (TR010) (SEQ ID No: 92) and reverse (TR006) (SEQ ID No: 88) primers to incorporate a homologous recombination site for the vector. The resulting PCR fragment is incubated with the pET101/D-TOPO® vector (Invitrogen) according to the manufacturer's directions, to create the human TNFR1 Δ7 bacterial expression vector. The resulting vector is transformed into the E. coli strain BL21 (DE3). The human TNFR1 Δ7 is then expressed from the bacterial cells according to the manufacturer's instructions.

EXAMPLE 20

Expression of Human TNFR1 Δ7 in Mammalian Cells

For expression of the human TNFR1 Δ7 protein in mammalian cells, a human TNFR1 Δ7 cDNA PCR product from Example 12 is incorporated into an appropriate mammalian expression vector. human TNFR1 Δ7 cDNA PCR product from Example 12 and the pcDNA™ 3.1D/V5-His TOPO® expression vector (Invitrogen) are blunt-end ligated according to the manufacturer's directions. The product is then isolated, amplified, and purified using standard molecular biology techniques to yield the mammalian expression vector. The vector is then transfected into a mammalian cell, where expression of the human TNFR1 Δ7 protein is driven by the strong constitutive CMVie promoter.

EXAMPLE 21

Expression of Human TNFR1 Δ7 in Insect Cells

For expression of the human TNFR1 Δ7 protein in insect cells, the cDNA from Example 12 is incorporated into a baculoviral vector. PCR is performed on the cDNA from Example 12 using forward (TR031) (SEQ ID No: 94) and reverse (TR032) (SEQ ID No: 95) primers. The resulting PCR product is digested with the restriction enzymes EcoRI and XhoI. The digested PCR product is ligated with a EcoRI and XhoI digested pENTR™ Vector (Invitrogen), such as any one of the pENTR™ 1A, pENTR™ 2B, pENTR™ 3C, pENTR™ 4, or pENTR™ 11 Vectors, to yield an entry vector. The product is then isolated, amplified, and purified using standard molecular biology techniques.

A baculoviral vector containing the human TNFR1 Δ7 cDNA is generated by homologous recombination of the entry vector with BaculoDirect™ Linear DNA (Invitrogen) using LR Clonase™ (Invitrogen) according to the manufacturer's directions. The reaction mixture is then used to infect Sf9 cells to generate recombinant baculovirus. After harvesting the recombinant baculovirus, expression of human TNFR1 Δ7 is confirmed. Amplification of the recombinant baculovirus yields a high-titer viral stock. The high-titer viral stock is used to infect Sf9 cells, thereby expressing human TNFR1 Δ7 protein.

EXAMPLE 22

Generation of Adeno-Associated Viral Vectors for the Expression of Human TNFR1 Δ7

For in vitro or in vivo delivery to mammalian cells of the human TNFR1 Δ7 gene for expression in those mammalian cells, a recombinant adeno-associated virus (rAAV) vector is generated using a three plasmid transfection system as described in Grieger, J., et al., 2006, Nature Protocols 1:1412. PCR is performed on the purified human TNFR1 Δ7 PCR product of Example 12, using forward (TR033) (SEQ ID No: 96) and reverse (TR034) (SEQ ID No: 97) primers to introduce unique flanking NotI restriction sites. The resulting PCR product is digested with the NotI restriction enzyme, and isolated by standard molecular biology techniques. The NotI-digested fragment is then ligated to NotI-digested pTR-UF2 (University of North Carolina (UNC) Vector Core Facility), to create a plasmid that contains the human TNFR1 Δ7 open reading frame, operably linked to the CMVie promoter, flanked by inverted terminal repeats. The resulting plasmid is then transfected with the plasmids pXX680 and pHelper (UNC Vector Core Facility) into HEK-293 cells, as described in Grieger, J., et al., to produce rAAV particles containing the human TNFR1 Δ7 gene where expression is driven by the strong constitutive CMVie promoter. The virus particles are harvested and purified, as described in Grieger, J., et al., to provide an rAAV stock suitable for transducing mammalian cells.

EXAMPLE 23

Construction of Vectors for the Expression of Mouse TNFR2 Δ7 in Mammalian Cells

For expression of the murine TNFR2 Δ7 protein in mammalian cells, a murine TNFR2 Δ7 cDNA PCR product from Example 13 was incorporated into an appropriate mammalian expression vector. The TNFR2 Δ7 cDNA PCR product from Example 13, both with and without a stop codon, and the pcDNA™ 3.1D/V5-His TOPO® expression vector (Invitrogen) was blunt-end ligated and isolated according to the manufacturer's directions. Plasmids containing inserts encoding murine Δ7 TNFR2 were transformed into One-Shot® Top10 competent cells (Invitrogen), according to the supplier's directions. Fifty µL of the transformation mix were plated on LB media with 100 µg/mL of ampicillin and incubated overnight at 37° C. Single colonies were used to inoculate 5 mL cultures of LB media with 100 µg/mL ampicillin and incubated overnight at 37° C. The cultures were then used to inoculate 200 mL of LB media with 100 µg/mL of ampicillin and grown overnight at 37° C. The plasmids were isolated using GenElute™ Plasmid Maxiprep kit (Sigma) according to manufacturer's directions. Purification efficiency ranged from 0.5 to 1.5 mg of plasmid per preparation.

Two murine TNFR2 Δ7 clones (1144-4 and 1145-3) were generated and sequenced. Clone 1144-4 contains the murine TNFR2 Δ7 open reading frame without a stop codon followed directly by an in-frame His-tag from the plasmid; while clone 1145-3 contains the TNFR2 Δ7 open reading frame followed immediately by a stop codon. The sequence of the His-tag from the plasmid is given in SEQ ID No: 126. Relative to SEQ ID No: 11, the sequence (SEQ ID No: 124) of the TNFR2 Δ7 open reading frames of the two clones, 1144-4 and 1145-3, differed by a single nucleotide at eleven positions. As a result of these single nucleotide changes there are four amino acid differences relative to SEQ ID No: 12.

EXAMPLE 24

Expression of Murine TNFR2 Δ7 in *E. coli*

For expression of the mouse TNFR2 Δ7 protein in bacteria, a murine TNFR2 Δ7 cDNA from Example 13 is incorporated into an appropriate expression vector, such as a pET Directional TOPO® expression vector (Invitrogen). PCR is performed on the PCR fragment from Example 13 using forward (TR035) (SEQ ID No: 106) and reverse (TR036) (SEQ ID No: 107) primers to incorporate a homologous recombination site for the vector. The resulting PCR fragment is incubated with the pET101/D-TOPO® vector (Invitrogen) according to the manufacturer's directions, to create the murine TNFR2 Δ7 bacterial expression vector. The resulting vector is transformed into the *E. coli* strain BL21 (DE3). The murine TNFR2 Δ7 is then expressed from the bacterial cells according to the manufacturer's instructions.

EXAMPLE 25

Expression of Mouse TNFR2 Δ7 in Insect Cells

For expression of the murine TNFR2 Δ7 protein in insect cells, the cDNA from Example 13 is incorporated into a baculoviral vector. PCR is performed on the cDNA from Example 13 using forward (TR037) (SEQ ID No: 108) and reverse (TR038) (SEQ ID No: 109) primers. The resulting PCR product is digested with the restriction enzymes EcoRI and XhoI. The digested PCR product is ligated with a EcoRI and XhoI digested pENTR™ Vector (Invitrogen), such as any one of the pENTR™ 1A, pENTR™ 2B, pENTR™ 3C, pENTR™ 4, or pENTR™ 11 Vectors, to yield an entry vector. The product is then isolated, amplified, and purified using standard molecular biology techniques.

A baculoviral vector containing the murine TNFR2 Δ7 cDNA is generated by homologous recombination of the entry vector with BaculoDirect™ Linear DNA (Invitrogen) using LR Clonase™ (Invitrogen) according to the manufacturer's directions. The reaction mixture is then used to infect Sf9 cells to generate recombinant baculovirus. After harvesting the recombinant baculovirus, expression of murine TNFR2 Δ7 is confirmed. Amplification of the recombinant baculovirus yields a high-titer viral stock. The high-titer viral stock is used to infect Sf9 cells, thereby expressing murine TNFR2 Δ7 protein.

EXAMPLE 26

Generation of Adeno-Associated Viral Vectors for the Expression of Murine TNFR2 Δ7

For in vitro or in vivo delivery to mammalian cells of the murine TNFR2 Δ7 gene for expression in those mammalian cells, a recombinant adeno-associated virus (rAAV) vector is generated using a three plasmid transfection system as described in Grieger, J., et al., 2006, Nature Protocols 1:1412. PCR is performed on the purified murine TNFR2 Δ7 PCR product of Example 13, using forward (TR039)(SEQ ID No: 110) and reverse (TR040) (SEQ ID No: 111) primers to introduce unique flanking NotI restriction sites. The resulting PCR product is digested with the NotI restriction enzyme, and isolated by standard molecular biology techniques. The NotI-digested fragment is then ligated to NotI-digested pTR-UF2 (University of North Carolina (UNC) Vector Core Facility), to create a plasmid that contains the murine TNFR2 Δ7 open reading frame, operably linked to the CMVie promoter, flanked by inverted terminal repeats. The resulting plasmid is then transfected with the plasmids pXX680 and pHelper (UNC Vector Core Facility) into HEK-293 cells, as described in Grieger, J., et al., to produce rAAV particles containing the murine TNFR2 Δ7 gene where expression is driven by the strong constitutive CMVie promoter. The virus particles are harvested and purified, as described in Grieger, J., et al., to provide an rAAV stock suitable for transducing mammalian cells.

EXAMPLE 27

Expression of Murine TNFR1 Δ7 in *E. coli*

For expression of the mouse TNFR1 Δ7 protein in bacteria, the cDNA from Example 14 is incorporated into an appropriate expression vector, such as a pET Directional TOPO® expression vector (Invitrogen). PCR is performed on the cDNA from Example 14 using forward (TR024) (SEQ ID No: 118) and reverse (TR020) (SEQ ID No: 114) primers to incorporate a homologous recombination site for the vector. The resulting PCR fragment is incubated with the pET 101/D-TOPO® vector (Invitrogen) according to the manufacturer's directions, to create the murine TNFR1 Δ7 bacterial expression vector. The resulting vector is transformed into the *E. coli* strain BL21(DE3). The murine TNFR1 Δ7 is then expressed from the bacterial cells according to the manufacturer's instructions.

EXAMPLE 28

Expression of Mouse TNFR1 Δ7 in Mammalian Cells

For expression of the murine TNFR1 Δ7 protein in mammalian cells, a murine TNFR1 Δ7 cDNA PCR product from Example 14 is incorporated into an appropriate mammalian expression vector. The murine TNFR1 Δ7 cDNA PCR product from Example 14 and the pcDNA™ 3.1D/V5-His TOPO® expression vector (Invitrogen) are blunt-end ligated according to the manufacturer's directions. The product is then isolated, amplified, and purified using standard molecular biology techniques to yield the mammalian expression vector. The vector is then transfected into a mammalian cell, where expression of the murine TNFR1 Δ7 protein is driven by the strong constitutive CMVie promoter.

EXAMPLE 29

Expression of Mouse TNFR1 Δ7 in Insect Cells

For expression of the murine TNFR1 Δ7 protein in insect cells, the cDNA from Example 14 is incorporated into a baculoviral vector. PCR is performed on the cDNA from Example 14 using forward (TR041) (SEQ ID No: 120) and reverse (TR042) (SEQ ID No: 121) primers. The resulting PCR product is digested with the restriction enzymes EcoRI and XhoI. The digested PCR product is ligated with a EcoRI and XhoI digested pENTR™ Vector (Invitrogen), such as any one of the pENTR™ 1A, pENTR™ 2B, pENTR™ 3C, pENTR™ 4, or pENTR™ 11 Vectors, to yield an entry vector. The product is then isolated, amplified, and purified using standard molecular biology techniques.

A baculoviral vector containing the murine TNFR1 Δ7 cDNA is generated by homologous recombination of the entry vector with BaculoDirect™ Linear DNA (Invitrogen) using LR Clonase™ (Invitrogen) according to the manufacturer's directions. The reaction mixture is then used to infect Sf9 cells to generate recombinant baculovirus. After harvesting the recombinant baculovirus, expression of murine TNFR1 Δ7 is confirmed. Amplification of the recombinant baculovirus yields a high-titer viral stock. The high-titer viral stock is used to infect Sf9 cells, thereby expressing murine TNFR1 Δ7 protein.

EXAMPLE 30

Generation of Adeno-Associated Viral Vectors for the Expression of Murine TNFR1 Δ7

For in vitro or in vivo delivery to mammalian cells of the murine TNFR1 Δ7 gene for expression in those mammalian cells, a recombinant adeno-associated virus (rAAV) vector is generated using a three plasmid transfection system as described in Grieger, J., et al., 2006, Nature Protocols 1:1412. PCR is performed on the purified murine TNFR1 Δ7 PCR product of Example 13, using forward (TR043) (SEQ ID No: 122) and reverse (TR044) (SEQ ID No: 123) primers to introduce unique flanking NotI restriction sites. The resulting PCR product is digested with the NotI restriction enzyme, and isolated by standard molecular biology techniques. The NotI-digested fragment is then ligated to NotI-digested pTR-UF2 (University of North Carolina (UNC) Vector Core Facility), to create a plasmid that contains the murine TNFR1 Δ7 open reading frame, operably linked to the CMVie promoter, flanked by inverted terminal repeats. The resulting plasmid is then transfected with the plasmids pXX680 and pHelper (UNC Vector Core Facility) into HEK-293 cells, as described in Grieger, J., et al., to produce rAAV particles containing the murine TNFR1 Δ7 gene where expression is driven by the strong constitutive CMVie promoter. The virus particles are harvested and purified, as described in Grieger, J., et al., to provide an rAAV stock suitable for transducing mammalian cells.

EXAMPLE 31

Generation of Lentiviral Vectors for the Expression of TNFR Δ7

For in vitro or in vivo delivery to mammalian cells of a TNFR Δ7 gene for expression in those mammalian cells, a replication-incompetent lentivirus vector is generated. A PCR product from Example 16, Example 19, Example 24 or Example 27 and the pLenti6/V5-D-TOPO® vector (Invitrogen) are blunt-end ligated according to the manufacturer's directions. The resulting plasmid is transformed into E. coli, amplified, and purified using standard molecular biology techniques. This plasmid is transfected into 293FT cells (Invitrogen) according to the manufacturer's directions to produce lentivirus particles containing the TNFR Δ7 gene where expression is driven by the strong constitutive CMVie promoter. The virus particles are harvested and purified, as described in Tiscornia, G., et al., 2006, Nature Protocols 1:241, to provide a lentiviral stock suitable for transducing mammalian cells.

EXAMPLE 32

Expression of TNFR2 Δ7 in Mammalian Cells

The plasmids generated in Example 15 and Example 23 were used to express active protein in mammalian HeLa cells, and the resulting proteins were tested for anti-TNF-α activity.

HeLa cells were seeded in at $1.0 \times 10^5$ cells per well in 24-well plates in SMEM media containing L-glutamine, gentamicin, kanamycin, 5% FBS and 5% HS. Cells were grown overnight at 37° C. in a 5% $CO_2$ humidified atmosphere. Approximately 250 ng of plasmid DNA was added to 50 μL of OPTI-MEM™, and then 50 μL Lipofectamine™ 2000 mix (1 part Lipofectamine™ 2000 to 25 parts OPTI-MEM™) was added and incubated for 20 minutes. Then 400 μL of serum free media was added and then applied to the cells in the 24-well plates. After incubation for ~48 hrs at 37° C. in a 5% $CO_2$ humidified atmosphere, the media was collected and the cells were harvested in 800 μL TRI-Reagent™. Total RNA was isolated from the cells per the manufacturer's directions and analyzed by RT-PCR using the forward primer TR047 (SEQ ID No: 84) and the reverse primer TR048 (SEQ ID No: 85) for human TNFR2 Δ7, or the forward primer TR045 (SEQ ID No: 112) and the reverse primer TR046 (SEQ ID No: 113) for mouse TNFR2 Δ7. The concentration of soluble TNFR2 in the media was measured by ELISA.

The anti-TNF-α activity of the above media was tested in an L929 cytotoxicity assay. L929 cells were plated in 96-well plates at $2 \times 10^4$ cells per well in MEM media containing 10% regular FBS, penicillin and streptomycin and grown overnight at 37° C. in a 5% $CO_2$ humidified atmosphere. The media samples were diluted 1, 2, 4, 8 and 16 fold with media from non-transfected HeLa cells. Ninety μL of each of these samples was added to 10 μL of serum-free media, containing 1.0 ng/ml TNF-α and 1 μg/ml of actinomycin D. The media from the cells were removed and replaced with these 100 μL samples. The cells were then grown overnight at 37° C. in a 5% $CO_2$ humidified atmosphere. Twenty μL CellTiter 96® $AQ_{ueous}$ One Solution Reagent (Promega) was then added to each well. Cell viability was measured 4 hrs later by measuring absorbance at 490 nm with a microplate reader. Cell viability was normalized to untreated cells nd plotted as a function of TNF antagonist concentration (FIG. 17).

The data from this example and from Example 9 were analyzed using the GraphPad Prism® software to determine the $EC_{50}$ value for each antagonist. For each antagonist from these examples a sigmoidal dose-response curve was fit by non-linear regression with the maximum and minimum responses held fixed to 100% and 0%, respectively. The $EC_{50}$ values shown in Table 5 correspond to a 95% confidence level, and each curve had an $r^2$ value ranging from 0.7 to 0.9.

TABLE 5

Activity of TNF-α antagonists

| TNF-α Antagonist | $EC_{50}$ (ng/mL) |
|---|---|
| Etanercept | 1.1 ± 0.5 |
| Recombinant soluble TNFR2 (rsTNFR2) | 698 ± 180 |
| SSO 3305 treated mice serum (mouse TNFR2 Δ7) | 0.6 ± 0.2 |
| SSO 3274 treated mice serum (mouse TNFR2 Δ7) | 0.8 ± 0.3 |
| Extracellular media from 1144-4 transfected HeLa cells (mouse TNFR2 Δ7) | 2.4 ± 1.4 |
| Extracellular media from 1145-3 transfected HeLa cells (mouse TNFR2 Δ7) | 2.4 ± 0.8 |
| Extracellular media from 1230-1 transfected HeLa cells (human TNFR2 Δ7) | 1.4 ± 1.1 |
| Extracellular media from 1319-1 transfected HeLa cells (human TNFR2 Δ7) | 1.7 ± 1.0 |
| Extracellular media from 1138-5 transfected HeLa cells (human TNFR2 Δ7) | 1.8 ± 1.1 |

EXAMPLE 33

Expression and Purification of TNFR2 Δ7 in Mammalian Cells

The plasmids generated in Example 15 and Example 23 were used to express and purify TNFR2 Δ7 from mammalian HeLa cells. HeLa cells were plated in 6-well plates at $5 \times 10^5$ cells per well, and grown overnight at 37° C., 5% $CO_2$, in humidified atmosphere. Each well was then transfected with 1.5 μg of plasmid DNA using either 1144-4 (mouse TNFR2 Δ7 with His-tag), 1145-1 (mouse TNFR2 Δ7, no His-tag), 1230-1 (human TNFR2 Δ7, no His-tag) or 1319-1 (human TNFR2 Δ7 with His-tag) plasmids. Media was collected ~48 hrs after transfection and concentrated approximately 40-fold using Amicon MWCO 30,000 filters. The cells were lysed in 120 μL of RIPA lysis buffer (Invitrogen) with protease inhibitors (Sigma-aldrich) for 5 minutes on ice. Protein concentration was determined by the Bradford assay. Proteins were then isolated from aliquots of the cell lysates and the extracellular media and analyzed by western blot for TNFR2 as described in Example 1 (FIG. 18).

Human and mouse TNFR2 Δ7 with a His-tag (clones 1319-1 and 1144-4, respectively) were purified from the above media by affinity chromatography. HisPur™ cobalt spin columns (Pierce) were used to purify mouse and human TNFR2 Δ7 containing a His-tag from the above media. Approximately 32 mL of media were applied to a 1 mL HisPur™ column equilibrated with 50 mM sodium phosphate, 300 mM sodium chloride, 10 mM imidazole buffer (pH 7.4) as recommended by the manufacturer. The column was then washed with two column volumes of the same buffer and protein was eluted with 1 mL of 50 mM sodium phosphate, 300 mM sodium chloride, 150 mM imidazole buffer (pH 7.4). Five μL of each eluate were analyzed by Western blot as described above (FIG. 19). TNFR2 Δ7 appears in the eluate and the multiple bands represent variably glycosylated forms of TNFR2 Δ7. As negative controls, the TNFR2 Δ7 proteins expressed from plasmids 1230-1 or 1145-1 which do not contain a His-tag where subjected to the above purification procedure. These proteins do not bind the affinity column and do not appear in the eluate (FIG. 19).

The invention claimed is:

1. An isolated nucleic acid molecule that encodes a polypeptide that consists of an amino acid sequence selected from the group consisting of: the amino acid sequence of SEQ ID NO: 10 and the amino acid sequence of amino acids 23-245 of SEQ ID NO: 10.

2. An isolated polypeptide consisting of an amino acid sequence selected from the group consisting of: SEQ ID NO:10 and the amino acid sequence of amino acids 23-435 of SEQ ID NO:10.

3. An expression vector comprising the nucleic acid molecule of claim 1, operably linked to a regulatory sequence.

4. A cell transformed with the expression vector of claim 3.

5. The cell of claim 4, wherein said cell is a mammalian cell, an insect cell, or a microbial cell.

6. A process for producing a polypeptide consisting of SEQ ID NO: 10 or the amino acid sequence of amino acids 23-245 of SEQ ID NO: 10, which process comprises culturing the cell of claim 5 under conditions suitable to express said polypeptide, and recovering said polyptide.

* * * * *

UNITED STATES PATENT AND TRADEMARK OFFICE
CERTIFICATE OF CORRECTION

PATENT NO. : 7,785,834 B2  Page 1 of 1
APPLICATION NO. : 11/799117
DATED : August 31, 2010
INVENTOR(S) : Peter L. Sazani et al.

It is certified that error appears in the above-identified patent and that said Letters Patent is hereby corrected as shown below:

Title page; item (56);

On the First Page, Column 2 (Other Publications), line 19, delete "Pesudotyped" and insert -- Pseudotyped --

On Column 106, line 35, delete "polyptide" and insert -- polypeptide. --

Signed and Sealed this

Twenty-third Day of November, 2010

David J. Kappos
*Director of the United States Patent and Trademark Office*

SEQUENCE LISTING

```
<160> NUMBER OF SEQ ID NOS: 126

<210> SEQ ID NO 1
<211> LENGTH: 1368
<212> TYPE: DNA
<213> ORGANISM: Homo sapiens

<400> SEQUENCE: 1
atgggcctct ccaccgtgcc tgacctgctg ctgccactgg tgctcctgga gctgttggtg      60
ggaatatacc cctcaggggt tattggactg gtccctcacc taggggacag ggagaagaga     120
gatagtgtgt gtccccaagg aaaatatatc caccctcaaa ataattcgat ttgctgtacc     180
aagtgccaca aaggaaccta cttgtacaat gactgtccag gcccggggca ggatacggac     240
tgcagggagt gtgagagcgg ctccttcacc gcttcagaaa accacctcag acactgcctc     300
agctgctcca aatgccgaaa ggaaatgggt caggtggaga tctcttcttg cacagtggac     360
cgggacaccg tgtgtggctg caggaagaac cagtaccggc attattggag tgaaaacctt     420
ttccagtgct tcaattgcag cctctgcctc aatgggaccg tgcacctctc ctgccaggag     480
aaacagaaca ccgtgtgcac ctgccatgca ggtttctttc taagagaaaa cgagtgtgtc     540
tcctgtagta actgtaagaa aagcctggag tgcacgaagt tgtgcctacc ccagattgag     600
aatgttaagg gcactgagga ctcaggcacc acagtgctgt tgcccctggt cattttcttt     660
ggtctttgcc ttttatccct cctcttcatt ggtttaatgt atcgctacca acggtggaag     720
tccaagctct actccattgt ttgtgggaaa tcgacacctg aaaaagaggg ggagcttgaa     780
ggaactacta ctaagcccct ggccccaaac ccaagcttca gtcccactcc aggcttcacc     840
cccaccctgg gcttcagtcc cgtgcccagt tccaccttca cctccagctc cacctatacc     900
cccggtgact gtcccaactt tgcggctccc gcagagagg tggcaccacc ctatcagggg     960
gctgacccca tccttgcgac agccctcgcc tccgacccca tccccaaccc ccttcagaag    1020
tgggaggaca cgcgccacaa gccacagagc ctagacactg atgacccgc gacgctgtac    1080 gccgtggtgg agaacgtgcc cccgttgcgc tggaaggaat tcgtgcggcg cctagggctg    1140
```

```
agcgaccacg agatcgatcg gctggagctg cagaacgggc gctgcctgcg cgaggcgcaa    1200
tacagcatgc tggcgacctg gaggcggcgc acgccgcggc gcgaggccac gctggagctg    1260
ctgggacgcg tgctccgcga catggacctg ctgggctgcc tggaggacat cgaggaggcg    1320
ctttgcggcc ccgccgccct cccgcccgcg cccagtcttc tcagatga                 1368
```

<210> SEQ ID NO 2
<211> LENGTH: 455
<212> TYPE: PRT
<213> ORGANISM: Homo sapiens

<400> SEQUENCE: 2

```
Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                      45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335
```

```
Pro Leu Gln Lys Trp Glu Asp Ser Ala His Lys Pro Gln Ser Leu Asp
                340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
        370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455

<210> SEQ ID NO 3
<211> LENGTH: 1386
<212> TYPE: DNA
<213> ORGANISM: Homo sapiens

<400> SEQUENCE: 3
atggcgcccg tcgccgtctg ggccgcgctg ccgtcggac tggagctctg ggctgcggcg        60
cacgccttgc cgcccaggt ggcatttaca ccctacgccc cggagcccgg gagcacatgc       120
cggctcagag aatactatga ccagacagct cagatgtgct gcagcaaatg ctcgccgggc       180
caacatgcaa aagtcttctg taccaagacc tcggacaccg tgtgtgactc ctgtgaggac       240
agcacataca cccagctctg gaactgggtt ccgagtgct gagctgtgg ctcccgctgt         300 agctctgacc aggtggaaac tcaagcctgc actcgggaac agaaccgcat ctgcacctgc       360
aggcccggct ggtactgcgc gctgagcaag caggaggggt gccggctgtg cgcgccgctg       420
cgcaagtgcc gccgggcttc ggcgtggcc agaccaggaa ctgaaacatc agacgtggtg       480
tgcaagccct gtgccccggg gacgttctcc aacacgactt catccacgga tatttgcagg       540
ccccaccaga tctgtaacgt ggtggccatc cctgggaatg caagcatgga tgcagtctgc       600
acgtccacgt cccccacccg gagtatggcc ccaggggcag tacacttacc ccagccagtg       660
tccacacgat cccaacacac gcagccaact ccagaaccca gcactgctcc aagcaccctcc     720 ttcctgctcc caatgggccc cagcccccca gctgaaggga gcactggcga cttcgctctt       780
ccagttggac tgattgtggg tgtgacagcc ttgggtctac taataatagg agtggtgaac       840
tgtgtcatca tgacccaggt gaaaaagaag cccttgtgcc tgcagagaga agccaaggtg       900
cctcacttgc ctgccgataa ggcccggggt acacagggcc ccgagcagca gcacctgctg       960
atcacagcgc cgagctccag cagcagctcc ctggagagct cggccagtgc gttggacaga     1020
agggcgccca tcggaacca gccacaggca ccaggcgtgg aggccagtgg ggccggggag      1080
gcccgggcca gcaccgggag ctcagattct tcccctggtg ccatgggac ccaggtcaat      1140 gtcacctgca tcgtgaacgt ctgtagcagc tctgaccaca gctcacagtg ctcctcccaa     1200
gccagctcca caatgggaga cacagattcc agccctcgg agtccccgaa ggacgagcag     1260
gtccccttct ccaaggagga atgtgccttt cggtcacagc tggagacgcc agagaccctg     1320
ctggggagca ccgaagagaa gcccctgccc cttggagtgc ctgatgctgg gatgaagccc     1380
agttaa                                                                1386
```

<210> SEQ ID NO 4
<211> LENGTH: 461
<212> TYPE: PRT
<213> ORGANISM: Homo sapiens

<400> SEQUENCE: 4

```
Met Ala Pro Val Ala Val Trp Ala Ala Leu Ala Val Gly Leu Glu Leu
1               5                   10                  15

Trp Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
```

```
            370                 375                 380
Val Asn Val Cys Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
                420                 425                 430

Gln Leu Glu Thr Pro Glu Thr Leu Gly Ser Thr Glu Glu Lys Pro
                435                 440                 445

Leu Pro Leu Gly Val Pro Asp Ala Gly Met Lys Pro Ser
    450                 455                 460

<210> SEQ ID NO 5
<211> LENGTH: 1254
<212> TYPE: DNA
<213> ORGANISM: Homo sapiens

<400> SEQUENCE: 5
atgggcctct ccaccgtgcc tgacctgctg ctgccactgg tgctcctgga gctgttggtg      60
ggaatatacc cctcaggggt tattggactg gtccctcacc taggggacag ggagaagaga     120
gatagtgtgt gtccccaagg aaaatatatc caccctcaaa ataattcgat ttgctgtacc     180
aagtgccaca aggaaccta cttgtacaat gactgtccag gccgggggca ggatacggac     240
tgcagggagt gtgagagcgg ctccttcacc gcttcagaaa accacctcag acactgcctc     300
agctgctcca atgccgaaa ggaaatgggt caggtggaga tctcttcttg cacagtggac     360
cgggacaccg tgtgtggctg caggaagaac cagtaccggc attattggag tgaaaaacctt    420 ttccagtgct tcaattgcag cctctgcctc aatgggaccg tgcacctctc ctgccaggag     480
aaacagaaca ccgtgtgcac ctgccatgca ggtttctttc taagagaaaa cgagtgtgtc     540
tcctgtagta actgtaagaa aagcctggag tgcacgaagt tgtgcctacc ccagattgag     600
aatgttaagg gcactgagga ctcagtttgt gggaaatcga cacctgaaaa agaggggagg     660
cttgaaggaa ctactactaa gccccctggcc ccaaacccaa gcttcagtcc cactccaggc     720
ttcaccccca ccctgggctt cagtcccgtg cccagttcca ccttcacctc agctccacc      780 tatacccccg tgactgtcc caactttgcg gctccccgca gagaggtggc caccaccctat     840 caggggggctg accccatcct gcgacagcc ctcgcctccg accccatccc caaccccctt     900
cagaagtggg aggacagcgc ccacaagcca cagagcctag acactgatga ccccgcgacg     960
ctgtacgccg tggtggagaa cgtgcccccg ttgcgctgga aggaattcgt gcggcgccta    1020
gggctgagcg accacgagat cgatcggctg gagctgcaga acgggcgctg cctgcgcgag    1080
gcgcaataca gcatgctggc gacctggagg cggcgcacgc cgcggcgcga ggccacgctg    1140
gagctgctgg gacgcgtgct ccgcgacatg gacctgctgg gctgcctgga ggacatcgag    1200
gaggcgcttt gcggccccgc cgccctcccg cccgcgccca gtcttctcag atga          1254

<210> SEQ ID NO 6
<211> LENGTH: 417
<212> TYPE: PRT
<213> ORGANISM: Homo sapiens

<400> SEQUENCE: 6

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
```

-continued

```
                20                  25                  30
His Leu Gly Asp Arg Glu Lys Arg Asp Ser Val Cys Pro Gln Gly Lys
             35                  40                  45

Tyr Ile His Pro Gln Asn Asn Ser Ile Cys Cys Thr Lys Cys His Lys
 50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
                100                 105                 110

Glu Ile Ser Ser Cys Thr Val Asp Arg Asp Thr Val Cys Gly Cys Arg
                115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
                180                 185                 190

Lys Leu Cys Leu Pro Gln Ile Glu Asn Val Lys Gly Thr Glu Asp Ser
                195                 200                 205

Val Cys Gly Lys Ser Thr Pro Glu Lys Glu Gly Glu Leu Glu Gly Thr
210                 215                 220

Thr Thr Lys Pro Leu Ala Pro Asn Pro Ser Phe Ser Pro Thr Pro Gly
225                 230                 235                 240

Phe Thr Pro Thr Leu Gly Phe Ser Pro Val Pro Ser Ser Thr Phe Thr
                245                 250                 255

Ser Ser Ser Thr Tyr Thr Pro Gly Asp Cys Pro Asn Phe Ala Ala Pro
                260                 265                 270

Arg Arg Glu Val Ala Pro Pro Tyr Gln Gly Ala Asp Pro Ile Leu Ala
                275                 280                 285

Thr Ala Leu Ala Ser Asp Pro Ile Pro Asn Pro Leu Gln Lys Trp Glu
290                 295                 300

Asp Ser Ala His Lys Pro Gln Ser Leu Asp Thr Asp Asp Pro Ala Thr
305                 310                 315                 320

Leu Tyr Ala Val Val Glu Asn Val Pro Pro Leu Arg Trp Lys Glu Phe
                325                 330                 335

Val Arg Arg Leu Gly Leu Ser Asp His Glu Ile Asp Arg Leu Glu Leu
                340                 345                 350

Gln Asn Gly Arg Cys Leu Arg Glu Ala Gln Tyr Ser Met Leu Ala Thr
                355                 360                 365

Trp Arg Arg Arg Thr Pro Arg Arg Glu Ala Thr Leu Glu Leu Leu Gly
                370                 375                 380

Arg Val Leu Arg Asp Met Asp Leu Leu Gly Cys Leu Glu Asp Ile Glu
385                 390                 395                 400

Glu Ala Leu Cys Gly Pro Ala Ala Leu Pro Pro Ala Pro Ser Leu Leu
                405                 410                 415

Arg
```

<210> SEQ ID NO 7
<211> LENGTH: 1251

<210> SEQ ID NO 7
<211> LENGTH: 1251
<212> TYPE: DNA
<213> ORGANISM: Mus sp.

<400> SEQUENCE: 7

```
atgggtctcc ccaccgtgcc tggcctgctg ctgtcactgg tgctcctggc tctgctgatg      60
gggatacatc catcaggggt cactggacta gtcccttctc ttggtgaccg ggagaagagg     120
gatagcttgt gtccccaagg aaagtatgtc cattctaaga caattccat ctgctgcacc      180
aagtgccaca aggaaccta cttggtgagt gactgtccga gcccagggcg ggatacagtc     240
tgcagggagt gtgaaaaggg cacctttacg gcttcccaga attacctcag gcagtgtctc     300
agttgcaaga catgtcggaa agaaatgtcc caggtggaga tctctccttg ccaagctgac     360
aaggacacgg tgtgtggctg taaggagaac cagttccaac gctacctgag tgagacacac     420
ttccagtgcg tggactgcag cccctgcttc aacggcaccg tgacaatccc ctgtaaggag     480
actcagaaca ccgtgtgtaa ctgccatgca gggttctttc tgagagaaag tgagtgcgtc     540
ccttgcagcc actgcaagaa aaatgaggag tgtatgaagt tgtgcctacc tcctccgctt     600
gcaaatgtca caaacccca ggactcagtt tgtagggatc ccgtgcctgt caaagaggag     660
aaggctggaa agcccctaac tccagccccc tccccagcct tcagccccac ctccggcttc     720
aaccccactc tgggcttcag caccccaggc tttagttctc ctgtctccag tacccccatc     780
agccccatct tcggtcctag taactggcac ttcatgccac ctgtcagtga ggtagtccca     840
acccagggag ctgaccctct gctctacgaa tcactctgct ccgtgccagc ccccaccctct     900
gttcagaaat gggaagactc cgcccacccg caacgtcctg acaatgcaga ccttgcgatt     960
ctgtatgctg tggtggatgg cgtgcctcca gcgcgctgga aggagttcat gcgtttcatg    1020
gggctgagcg agcacgagat cgagaggctg gagatgcaga cgggcgctg cctgcgcgag    1080
gctcagtaca gcatgctgga agcctggcgg cgccgcacgc cgcgccacga ggacacgctg    1140
gaagtagtgg gcctcgtgct ttccaagatg aacctggctg ggtgcctgga gaatatcctc    1200
gaggctctga gaaatcccgc cccctcgtcc acgacccgcc tcccgcgata a             1251
```

<210> SEQ ID NO 8
<211> LENGTH: 416
<212> TYPE: PRT
<213> ORGANISM: Mus sp.

<400> SEQUENCE: 8

Met Gly Leu Pro Thr Val Pro Gly Leu Leu Leu Ser Leu Val Leu Leu
1               5                   10                  15

Ala Leu Leu Met Gly Ile His Pro Ser Gly Val Thr Gly Leu Val Pro
            20                  25                  30

Ser Leu Gly Asp Arg Glu Lys Arg Asp Ser Leu Cys Pro Gln Gly Lys
        35                  40                  45

Tyr Val His Ser Lys Asn Asn Ser Ile Cys Cys Thr Lys Cys His Lys
    50                  55                  60

Gly Thr Tyr Leu Val Ser Asp Cys Pro Ser Pro Gly Arg Asp Thr Val
65                  70                  75                  80

Cys Arg Glu Cys Glu Lys Gly Thr Phe Thr Ala Ser Gln Asn Tyr Leu
                85                  90                  95

Arg Gln Cys Leu Ser Cys Lys Thr Cys Arg Lys Glu Met Ser Gln Val
            100                 105                 110

Glu Ile Ser Pro Cys Gln Ala Asp Lys Asp Thr Val Cys Gly Cys Lys
        115                 120                 125

| | | | | | | | | | | | | |
|---|---|---|---|---|---|---|---|---|---|---|---|---|
|Glu|Asn|Gln|Phe|Gln|Arg|Tyr|Leu|Ser|Glu|Thr|His|Phe|Gln|Cys|Val|
| |130| | | | |135| | | | |140| | | | |

Glu Asn Gln Phe Gln Arg Tyr Leu Ser Glu Thr His Phe Gln Cys Val
    130                 135                 140

Asp Cys Ser Pro Cys Phe Asn Gly Thr Val Thr Ile Pro Cys Lys Glu
145                 150                 155                 160

Thr Gln Asn Thr Val Cys Asn Cys His Ala Gly Phe Phe Leu Arg Glu
            165                 170                 175

Ser Glu Cys Val Pro Cys Ser His Cys Lys Lys Asn Glu Glu Cys Met
            180                 185                 190

Lys Leu Cys Leu Pro Pro Leu Ala Asn Val Thr Asn Pro Gln Asp
            195                 200                 205

Ser Val Cys Arg Asp Pro Val Pro Val Lys Glu Lys Ala Gly Lys
    210                 215                 220

Pro Leu Thr Pro Ala Pro Ser Pro Ala Phe Ser Pro Thr Ser Gly Phe
225                 230                 235                 240

Asn Pro Thr Leu Gly Phe Ser Thr Pro Gly Phe Ser Ser Pro Val Ser
            245                 250                 255

Ser Thr Pro Ile Ser Pro Ile Phe Gly Pro Ser Asn Trp His Phe Met
            260                 265                 270

Pro Pro Val Ser Glu Val Pro Thr Gln Gly Ala Asp Pro Leu Leu
    275                 280                 285

Tyr Glu Ser Leu Cys Ser Val Pro Ala Pro Thr Ser Val Gln Lys Trp
    290                 295                 300

Glu Asp Ser Ala His Pro Gln Arg Pro Asp Asn Ala Asp Leu Ala Ile
305                 310                 315                 320

Leu Tyr Ala Val Val Asp Gly Val Pro Pro Ala Arg Trp Lys Glu Phe
            325                 330                 335

Met Arg Phe Met Gly Leu Ser Glu His Glu Ile Glu Arg Leu Glu Met
            340                 345                 350

Gln Asn Gly Arg Cys Leu Arg Glu Ala Gln Tyr Ser Met Leu Glu Ala
            355                 360                 365

Trp Arg Arg Arg Thr Pro Arg His Glu Asp Thr Leu Glu Val Val Gly
370                 375                 380

Leu Val Leu Ser Lys Met Asn Leu Ala Gly Cys Leu Glu Asn Ile Leu
385                 390                 395                 400

Glu Ala Leu Arg Asn Pro Ala Pro Ser Ser Thr Thr Arg Leu Pro Arg
            405                 410                 415

<210> SEQ ID NO 9
<211> LENGTH: 1308
<212> TYPE: DNA
<213> ORGANISM: Homo sapiens

<400> SEQUENCE: 9
atggcgcccg tcgccgtctg ggccgcgctg gccgtcggac tggagctctg ggctgcggcg      60
cacgccttgc cgcccaggt ggcatttaca ccctacgccc ggagcccgg gagcacatgc      120 cggctcagag aatactatga ccagacagct cagatgtgct gcagcaaatg ctcgccgggc      180
caacatgcaa aagtcttctg taccaagacc tcggacaccg tgtgtgactc ctgtgaggac      240
agcacataca cccagctctg gaactgggtt cccgagtgct gagctgtgg ctcccgctgt      300 agctctgacc aggtggaaac tcaagcctgc actcggaac agaaccgcat ctgcacctgc      360
aggcccggct ggtactgcgc gctgagcaag caggaggggt gccggctgtg cgcgccgctg      420
cgcaagtgcc gccgggcttt cggcgtggcc agaccaggaa ctgaaacatc agacgtggtg      480
tgcaagccct gtccccgggg acgttctcc aacacgactt catccacgga tatttgcagg      540

```
cccaccaga tctgtaacgt ggtggccatc cctgggaatg caagcatgga tgcagtctgc      600
acgtccacgt cccccacccg gagtatggcc cagggggcag tacacttacc ccagccagtg      660
tccacacgat cccaacacac gcagccaact ccagaaccca gcactgctcc aagcacctcc      720
ttcctgctcc caatgggccc cagccccca gctgaaggga gcactggcga cttcgctctt      780
ccagttgaga agcccttgtg cctgcagaga aagccaagg tgcctcactt gcctgccgat      840
aaggcccggg gtacacaggg ccccgagcag cagcacctgc tgatcacagc gccgagctcc      900
agcagcagct ccctggagag ctcggccagt gcgttggaca aagggcgcc cactcggaac      960 cagccacagg caccaggcgt ggaggccagt ggggccgggg aggcccgggc cagcaccggg     1020
agctcagatt cttcccctgg tggccatggg acccaggtca atgtcacctg catcgtgaac     1080
gtctgtagca gctctgacca cagctcacag tgctcctccc aagccagctc cacaatggga     1140
gacacagatt ccagcccctc ggagtccccg aaggacgagc aggtccccctt ctccaaggag     1200 gaatgtgcct ttcggtcaca gctggagacg ccagagaccc tgctggggag caccgaagag     1260
aagcccctgc cccttggagt gcctgatgct gggatgaagc ccagttaa                  1308
```

<210> SEQ ID NO 10
<211> LENGTH: 435
<212> TYPE: PRT
<213> ORGANISM: Homo sapiens

<400> SEQUENCE: 10

```
Met Ala Pro Val Ala Val Trp Ala Ala Leu Ala Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240
```

Phe Leu Leu Pro Met Gly Pro Ser Pro Pro Ala Glu Gly Ser Thr Gly
            245                 250                 255

Asp Phe Ala Leu Pro Val Glu Lys Pro Leu Cys Leu Gln Arg Glu Ala
        260                 265                 270

Lys Val Pro His Leu Pro Ala Asp Lys Ala Arg Gly Thr Gln Gly Pro
    275                 280                 285

Glu Gln Gln His Leu Leu Ile Thr Ala Pro Ser Ser Ser Ser Ser Ser
290                 295                 300

Leu Glu Ser Ser Ala Ser Ala Leu Asp Arg Arg Ala Pro Thr Arg Asn
305                 310                 315                 320

Gln Pro Gln Ala Pro Gly Val Glu Ala Ser Gly Ala Gly Glu Ala Arg
                325                 330                 335

Ala Ser Thr Gly Ser Ser Asp Ser Ser Pro Gly Gly His Gly Thr Gln
            340                 345                 350

Val Asn Val Thr Cys Ile Val Asn Val Cys Ser Ser Ser Asp His Ser
        355                 360                 365

Ser Gln Cys Ser Ser Gln Ala Ser Ser Thr Met Gly Asp Thr Asp Ser
    370                 375                 380

Ser Pro Ser Glu Ser Pro Lys Asp Glu Gln Val Pro Phe Ser Lys Glu
385                 390                 395                 400

Glu Cys Ala Phe Arg Ser Gln Leu Glu Thr Pro Glu Thr Leu Leu Gly
                405                 410                 415

Ser Thr Glu Glu Lys Pro Leu Pro Leu Gly Val Pro Asp Ala Gly Met
            420                 425                 430

Lys Pro Ser
    435

<210> SEQ ID NO 11
<211> LENGTH: 1347
<212> TYPE: DNA
<213> ORGANISM: Mus sp.

<400> SEQUENCE: 11
atggcgcccg ccgccctctg gtcgcgctg gtcttcgaac tgcagctgtg gccaccggg       60 cacacagtgc ccgcccaggt tgtcttgaca ccctacaaac cggaacctgg gtacgagtgc      120
cagatctcac aggaatacta tgacaggaag gctcagatgt gctgtgctaa gtgtcctcct      180
ggccaatatg tgaaacattt ctgcaacaag acctcggaca ccgtgtgtgc ggactgtgag      240
gcaagcatgt atacccaggt ctggaaccag tttcgtacat gtttgagctg cagttcttcc      300
tgtaccactg accaggtgga gatccgcgcc tgcactaaac agcagaaccg agtgtgtgct      360
tgcgaagctg gcaggtactg cgccttgaaa acccattctg cagctgtcg acagtgcatg      420 aggctgagca agtgcggccc tggcttcgga gtggccagtt caagagcccc aaatggaaat      480
gtgctatgca aggcctgtgc cccagggacg ttctctgaca ccacatcatc cactgatgtg      540
tgcaggcccc accgcatctg tagcatcctg gctattccg gaaatgcaag cacagatgca      600
gtctgtgcgc ccgagtcccc aactctaagt gccatcccaa ggacactcta cgtatctcag      660
ccagagccca agatccca accctggat caagagccag gcccagcca actccaagc          720 atccttacat cgttgggttc aacccccatt attgaacaaa gtaccaaggg tggcatctct      780
cttccaattg agaagccctc ctgcctacaa agagatgcca aggtgcctca tgtgcctgat      840
gagaaatccc aggatgcagt aggccttgag cagcagcacc tgttgaccac agcacccagt      900
tccagcagca gctccctaga gagctcagcc agcgctgggg accgaagggc gcccctggg      960

```
ggccatcccc aagcaagagt catggcggag gcccaagggt tcaggaggc ccgtgccagc   1020 tccaggattt cagattcttc ccacggaagc cacgggaccc acgtcaacgt cacctgcatc   1080
gtgaacgtct gtagcagctc tgaccacagt tctcagtgct cttcccaagc cagcgccaca   1140
gtgggagacc cagatgccaa gccctcagcg tccccaaagg atgagcaggt ccccttctct   1200
caggaggagt gtccgtctca gtccccgtgt gagactacag agacactgca gagccatgag   1260
aagcccttgc cccttggtgt gccggatatg ggcatgaagc ccagccaagc tggctggttt   1320
gatcagattg cagtcaaagt ggcctga                                       1347

<210> SEQ ID NO 12
<211> LENGTH: 448
<212> TYPE: PRT
<213> ORGANISM: Mus sp.

<400> SEQUENCE: 12

Met Ala Pro Ala Ala Leu Trp Val Ala Leu Val Phe Glu Leu Gln Leu
1               5                   10                  15

Trp Ala Thr Gly His Thr Val Pro Ala Gln Val Val Leu Thr Pro Tyr
            20                  25                  30

Lys Pro Glu Pro Gly Tyr Glu Cys Gln Ile Ser Gln Glu Tyr Tyr Asp
        35                  40                  45

Arg Lys Ala Gln Met Cys Cys Ala Lys Cys Pro Pro Gly Gln Tyr Val
    50                  55                  60

Lys His Phe Cys Asn Lys Thr Ser Asp Thr Val Cys Ala Asp Cys Glu
65                  70                  75                  80

Ala Ser Met Tyr Thr Gln Val Trp Asn Gln Phe Arg Thr Cys Leu Ser
                85                  90                  95

Cys Ser Ser Ser Cys Thr Thr Asp Gln Val Glu Ile Arg Ala Cys Thr
            100                 105                 110

Lys Gln Gln Asn Arg Val Cys Ala Cys Glu Ala Gly Arg Tyr Cys Ala
        115                 120                 125

Leu Lys Thr His Ser Gly Ser Cys Arg Gln Cys Met Arg Leu Ser Lys
    130                 135                 140

Cys Gly Pro Gly Phe Gly Val Ala Ser Ser Arg Ala Pro Asn Gly Asn
145                 150                 155                 160

Val Leu Cys Lys Ala Cys Ala Pro Gly Thr Phe Ser Asp Thr Thr Ser
                165                 170                 175

Ser Thr Asp Val Cys Arg Pro His Arg Ile Cys Ser Ile Leu Ala Ile
            180                 185                 190

Pro Gly Asn Ala Ser Thr Asp Ala Val Cys Ala Pro Glu Ser Pro Thr
        195                 200                 205

Leu Ser Ala Ile Pro Arg Thr Leu Tyr Val Ser Gln Pro Glu Pro Thr
    210                 215                 220

Arg Ser Gln Pro Leu Asp Gln Glu Pro Gly Pro Ser Gln Thr Pro Ser
225                 230                 235                 240

Ile Leu Thr Ser Leu Gly Ser Thr Pro Ile Ile Glu Gln Ser Thr Lys
                245                 250                 255

Gly Gly Ile Ser Leu Pro Ile Glu Lys Pro Ser Cys Leu Gln Arg Asp
            260                 265                 270

Ala Lys Val Pro His Val Pro Asp Glu Lys Ser Gln Asp Ala Val Gly
        275                 280                 285

Leu Glu Gln Gln His Leu Leu Thr Thr Ala Pro Ser Ser Ser Ser Ser
    290                 295                 300
```

```
Ser Leu Glu Ser Ser Ala Ser Ala Gly Asp Arg Arg Ala Pro Pro Gly
305                 310                 315                 320

Gly His Pro Gln Ala Arg Val Met Ala Glu Ala Gln Gly Phe Gln Glu
                325                 330                 335

Ala Arg Ala Ser Ser Arg Ile Ser Asp Ser Ser His Gly Ser His Gly
            340                 345                 350

Thr His Val Asn Val Thr Cys Ile Val Asn Val Cys Ser Ser Ser Asp
        355                 360                 365

His Ser Ser Gln Cys Ser Ser Gln Ala Ser Ala Thr Val Gly Asp Pro
    370                 375                 380

Asp Ala Lys Pro Ser Ala Ser Pro Lys Asp Glu Gln Val Pro Phe Ser
385                 390                 395                 400

Gln Glu Glu Cys Pro Ser Gln Ser Pro Cys Glu Thr Thr Glu Thr Leu
                405                 410                 415

Gln Ser His Glu Lys Pro Leu Pro Leu Gly Val Pro Asp Met Gly Met
            420                 425                 430

Lys Pro Ser Gln Ala Gly Trp Phe Asp Gln Ile Ala Val Lys Val Ala
        435                 440                 445

<210> SEQ ID NO 13
<211> LENGTH: 178
<212> TYPE: DNA
<213> ORGANISM: Homo sapiens

<400> SEQUENCE: 13
acatttgagt tgttttctg tagctgtctg agcttctctt ttctttctag gactgattgt      60
gggtgtgaca gccttgggtc tactaataat aggagtggtg aactgtgtca tcatgaccca    120
ggtgaaaagt aagagtccat ccttccttcc ttcatccact tgttcaggaa gcttttgt     178

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccacaatcag tcctag                                                    16

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
acaatcagtc ctag                                                      14

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
```

```
aatcagtcct ag                                                    12

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcagtcctag                                                       10

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccacaatcag tcct                                                  14

<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccacaatcag tc                                                    12

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccacaatcag                                                       10

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cacaatcagt ccta                                                  14

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cacaatcagt cc                                                    12
```

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
acaatcagtc ct                                                            12

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
caatcagtcc ta                                                            12

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cacaatcagt                                                               10

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
acaatcagtc                                                               10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
caatcagtcc                                                               10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aatcagtcct                                                               10

```
<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
atcagtccta                                                          10

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cagtcctaga aagaaa                                                   16

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtcctagaaa gaaa                                                     14

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cctagaaaga aa                                                       12

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tagaaagaaa                                                          10

<210> SEQ ID NO 34
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cagtcctaga aaga                                                     14
```

<210> SEQ ID NO 35
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cagtcctaga aa                                                              12

<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cagtcctaga                                                                 10

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agtcctagaa agaa                                                            14

<210> SEQ ID NO 38
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agtcctagaa ag                                                              12

<210> SEQ ID NO 39
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gtcctagaaa ga                                                              12

<210> SEQ ID NO 40
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcctagaaag aa                                                              12

<210> SEQ ID NO 41

```
<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
agtcctagaa                                                              10

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gtcctagaaa                                                              10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tcctagaaag                                                              10

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cctagaaaga                                                              10

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctagaaagaa                                                              10

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46 actttttcacc tgggtc                                                      16

<210> SEQ ID NO 47
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttttcacctg ggtc                                                    14

<210> SEQ ID NO 48
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttcacctggg tc                                                      12

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cacctgggtc                                                         10

<210> SEQ ID NO 50
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50 actttttcacc tggg                                                   14

<210> SEQ ID NO 51
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51 actttttcacc tg                                                     12

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
acttttcacc                                                         10

<210> SEQ ID NO 53
<211> LENGTH: 14
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 53
cttttcacct gggt                                                           14

<210> SEQ ID NO 54
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cttttcacct gg                                                             12

<210> SEQ ID NO 55
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ttttcacctg gg                                                             12

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tttcacctgg gt                                                             12

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cttttcacct                                                                10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ttttcacctg                                                                10

<210> SEQ ID NO 59
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 59
tttcacctgg                                                          10

<210> SEQ ID NO 60
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ttcacctggg                                                          10

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tcacctgggt                                                          10

<210> SEQ ID NO 62
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
agagcagaac cttact                                                   16

<210> SEQ ID NO 63
<211> LENGTH: 10
<212> TYPE: DNA
<213> ORGANISM: Artificial Sequence
<220> FEATURE:
<223> OTHER INFORMATION: Description of DNA/RNA hybrid: Synthetic
      oligonuculeotide
<220> FEATURE:
<223> OTHER INFORMATION: Description of Artificial Sequence: Synthetic
      oligonucleotide

<400> SEQUENCE: 63
gaacctuact                                                          10

<210> SEQ ID NO 64
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
agagcagaac                                                          10

<210> SEQ ID NO 65
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gagcagaacc                                                             10

<210> SEQ ID NO 66
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
agcagaacct                                                             10

<210> SEQ ID NO 67
<211> LENGTH: 10
<212> TYPE: DNA
<213> ORGANISM: Artificial Sequence
<220> FEATURE:
<223> OTHER INFORMATION: Description of DNA/RNA hybrid: Synthetic
      oligonculeotide
<220> FEATURE:
<223> OTHER INFORMATION: Description of Artificial Sequence: Synthetic
      oligonucleotide

<400> SEQUENCE: 67
gcagaaccut                                                             10

<210> SEQ ID NO 68
<211> LENGTH: 10
<212> TYPE: DNA
<213> ORGANISM: Artificial Sequence
<220> FEATURE:
<223> OTHER INFORMATION: Description of DNA/RNA hybrid: Synthetic
      oligonculeotide
<220> FEATURE:
<223> OTHER INFORMATION: Description of Artificial Sequence: Synthetic
      oligonucleotide

<400> SEQUENCE: 68
cagaacctua                                                             10

<210> SEQ ID NO 69
<211> LENGTH: 10
<212> TYPE: DNA
<213> ORGANISM: Artificial Sequence
<220> FEATURE:
<223> OTHER INFORMATION: Description of DNA/RNA hybrid: Synthetic
      oligonculeotide
<220> FEATURE:
<223> OTHER INFORMATION: Description of Artificial Sequence: Synthetic
      oligonucleotide

<400> SEQUENCE: 69
agaaccutac                                                             10

<210> SEQ ID NO 70
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 70
ccactcctat tattag                                                      16

<210> SEQ ID NO 71
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
caccactcct attatt                                                      16

<210> SEQ ID NO 72
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tggactctta cttttc                                                      16

<210> SEQ ID NO 73
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
aaggatggac tcttac                                                      16

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
actgggcttc atcccagcat c                                                21

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
caccatggcg cccgtcgccg tctgg                                            25

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 76
cgacttcgct cttccagttg agaagccctt gtgcctgcag          40

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ttaactgggc ttcatcccag catc          24

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctgcaggcac aagggcttct caactggaag agcgaagtcg          40

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ttaactgggc ttcatcccag c          21

<210> SEQ ID NO 80
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
cgatagaatt catggcgccc gtcgccgtct gg          32

<210> SEQ ID NO 81
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cctaactcga gttaactggg cttcatccca gc          32

<210> SEQ ID NO 82
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gactgagcgg ccgccaccat ggcgcccgtc gccgtctgg                                39

<210> SEQ ID NO 83
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ctaagcgcgg ccgcttaact gggcttcatc ccagcatc                                 38

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cgttctccaa cacgacttca                                                     20

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cttatcggca ggcaagtgag g                                                   21

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
actgaaacat cagacgtggt gtgc                                                24

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ccttatcggc aggcaagtga g                                                   21

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cctcatctga aagactggg cg                                        22

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gccaccatgg gcctctccac cgtgc                                    25

<210> SEQ ID NO 90
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gggcactgag gactcagttt gtgggaaatc gacacctg                      38

<210> SEQ ID NO 91
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
caggtgtcga tttcccacaa actgagtcct cagtgccc                      38

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
caccatgggc ctctccaccg tgc                                      23

<210> SEQ ID NO 93
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tctgagaaga ctgggcg                                             17

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cgataggatc catgggcctc tccaccgtgc                               30

<210> SEQ ID NO 95
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cctaactcga gtcatctgag aagactgggc g                                  31

<210> SEQ ID NO 96
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gactgagcgg ccgccaccat gggcctctcc accgtgc                            37

<210> SEQ ID NO 97
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ctaagcgcgg ccgctcatct gagaagactg ggcg                               34

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggtcaggcca ctttgactgc                                               20

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
caccgctgcc cctatggcg                                                19

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
caccgctgcc actatggcg                                                19

```
<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ggtcaggcca ctttgactgc aatc                                              24

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gccaccatgg cgcccgccgc cctctgg                                           27

<210> SEQ ID NO 103
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ggcatctctc ttccaattga agccctcc tgcctacaaa g                             41

<210> SEQ ID NO 104
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ctttgtaggc aggagggctt ctcaattgga agagagatgc c                           41

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ggccactttg actgcaatct g                                                 21

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
caccatggcg cccgccgccc tctgg                                             25
```

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tcaggccact ttgactgcaa tc                                              22

<210> SEQ ID NO 108
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cgatagaatt catggcgccc gccgccctct gg                                   32

<210> SEQ ID NO 109
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cctaactcga gtcaggccac tttgactgca atc                                  33

<210> SEQ ID NO 110
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gactgagcgg ccgccaccat ggcgcccgcc gccctctgg                            39

<210> SEQ ID NO 111
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ctaagcgcgg ccgctcaggc cactttgact gcaatc                               36

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gagccccaaa tggaaatgtg c                                               21

<210> SEQ ID NO 113

<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gctcaaggcc tactgcatcc                                              20

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggttatcgcg ggaggcgggt cg                                           22

<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gccaccatgg gtctccccac cgtgcc                                       26

<210> SEQ ID NO 116
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
cacaaacccc caggactcag tttgtaggga tcccgtgcct                        40

<210> SEQ ID NO 117
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
aggcacggga tccctacaaa ctgagtcctg ggggtttgtg                        40

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
caccatgggt ctccccaccg tgcc                                         24

<210> SEQ ID NO 119
<211> LENGTH: 20

-continued

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
tcgcgggagg cgggtcgtgg                                                  20

<210> SEQ ID NO 120
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 120
cgatagtcga catgggtctc cccaccgtgc c                                     31

<210> SEQ ID NO 121
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121
cctaagaatt cttatcgcgg gaggcgggtc g                                     31

<210> SEQ ID NO 122
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 122
gactgagcgg ccgccaccat gggtctcccc accgtgcc                              38

<210> SEQ ID NO 123
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 123
ctaagcgcgg ccgcttatcg cgggaggcgg gtcg                                  34

<210> SEQ ID NO 124
<211> LENGTH: 1347
<212> TYPE: DNA
<213> ORGANISM: Mus sp.

<400> SEQUENCE: 124
atggcgcccg ccgccctctg gtcgcgctg gtcttcgaac tgcagctgtg ggccaccggg       60
cacacagtgc cgcccaggt tgtcttgaca ccctacaaac cggaacctgg gtacgagtgc      120
cagatctcac aggaatacta tgacaggaag gctcagatgt gctgtgctaa gtgtcctcct     180
ggccaatatg tgaaacattt ctgcaacaag acctcggaca ccgtgtgtgc ggactgtgag     240
gcaagcatgt atacccaggt ctggaaccag tttcgtacat gtttgagctg cagttcttcc    300

```
tgtagcactg accaggtgga gacccgcgcc tgcactaaac agcagaaccg agtgtgtgct    360
tgcgaagctg gcaggtactg cgccttgaaa acccattctg gcagctgtcg acagtgcatg    420
aggctgagca agtgcggccc tggcttcgga gtggccagtt caagagcccc aaatggaaat    480
gtgctatgca aggcctgtgc cccagggacg ttctctgaca ccacatcatc cacagatgtg    540
tgcaggcccc accgcatctg tagcatcctg gctattcccg gaaatgcaag cacagatgca    600
gtctgtgcgc ccgagtcccc aactctaagt gccatcccaa ggacactcta cgtatctcag    660
ccagagccca caagatccca acccctggat caagagccag ggcccagcca aactccaagc    720
atccttacat cgttgggttc aacccccatt attgaacaaa gtaccaaggg tggcatctct    780
cttccaattg agaagccctc ctgcctacaa agagatgcca aggtgcctca tgtgcctgat    840
gagaaatccc aggatgcagt aggccttgag cagcagcacc tgttgactac agcacccagt    900
tccagcagca gctccctaga gagctcagcc agcgctgggg atcgaagggc gccccctggg    960
ggccatcccc aagcaagagt catggcggag gcccaagggt ctcaggaggc ccgcgccagc   1020
tccaggattt cagattcttc ccacggaagc cacgggaccc acgtcaacgt cacctgcatc   1080
gtgaacgtct gtagcagctc tgaccacagc tctcagtgct cttcccaagc cagcgccacg   1140
gtgggagacc cagatgccaa gccctcagcg tccccaaagg atgagcaggt ccccttctct   1200
caggaggagt gtccgtctca gtccccgtat gagactacag agacactgca gagccatgag   1260
aagcccttgc cccttggtgt gccagatatg ggcatgaagc ccagccaagc tggctggttt   1320
gatcagattg cagtcaaagt ggcctga                                       1347

<210> SEQ ID NO 125
<211> LENGTH: 1308
<212> TYPE: DNA
<213> ORGANISM: Homo sapiens

<400> SEQUENCE: 125
atggcgcccg tcgccgtctg gccgcgctg gccgtcggac tggagctctg ggctgcggcg    60
cacgccttgc ccgcccaggt ggcatttaca ccctacgccc cggagcccgg gagcacatgc   120
cggctcagag aatactatga ccagacagct cagatgtgct gcagcaaatg ctcgccgggc   180
caacatgcaa aagtcttctg taccaagacc tcggacaccg tgtgtgactc ctgtgaggac   240
agcacataca cccagctctg gaactgggtt cccgagtgct tgagctgtgg ctcccgctgt   300
agctctgacc aggtggaaac tcaagcctgc actcgggaac agaaccgcat ctgcacctgc   360
aggcccggct ggtactgcgc gctgagcaag caggaggggt gccggctgtg cgcgccgctg   420
cgcaagtgcc gccgggctt cggcgtggcc agaccaggaa ctgaaacatc agacgtggtg   480
tgcaagccct gtgccccggg gacgttctcc aacacgactt catccacgga tatttgcagg   540
ccccaccaga tctgtaacgt ggtggccatc cctgggaatg caagcatgga tgcagtctgc   600
acgtccacgt cccccacccg gagtatggcc ccaggggcag tacacttacc ccagccagtg   660
tccacacgat cccaacacac gcagccaact ccagaaccca gcactgctcc aagcaccctcc   720 ttcctgctcc caatgggccc cagccccca gctgaaggga gcactggcga cttcgctctt   780
ccagttgaga agcccttgtg cctgcagaga aagccaagg tgcctcactt gcctgccgat   840
aaggcccggg gtacacaggg ccccgagcag cagcacctgc tgatcacagc gccgagctcc   900
agcagcagct ccctgagag ctcgccagt gcgttggaca aagggcgcc cactcggaac   960 cagccacagg caccaggcgt ggaggccagt ggggccgggg aggcccgggc cagcaccggg   1020
```

-continued

```
agctcagatt cttccctgg tggccatggg acccgggtca atgtcacctg catcgtgaac      1080
gtctgtagca gctctgacca cagctcacag tgctcctccc aagccagctc cacaatggga      1140
gacacagatt ccagcccctc ggagtccccg aaggacgagc aggtcccctt ctccaaggag      1200
gaatgtgcct ttcggtcaca gctggagacg ccagagaccc tgctggggag caccgaagag      1260
aagcccctgc cccttggagt gcctgatgct gggatgaagc ccagttaa                   1308
```

<210> SEQ ID NO 126
<211> LENGTH: 144
<212> TYPE: DNA
<213> ORGANISM: Artificial Sequence
<220> FEATURE:
<223> OTHER INFORMATION: Description of Artificial Sequence: Synthetic
    nucleotide

<400> SEQUENCE: 126

```
aagggtcaag acaattctgc agatatccag cacagtggcg gccgctcgag tctagagggc        60
ccgcggttcg aaggtaagcc tatccctaac cctctcctcg gtctcgattc tacgcgtacc       120
ggtcatcatc accatcacca ttga                                              144
```